(12) United States Patent
Badkar et al.

(10) Patent No.: US 10,188,600 B2
(45) Date of Patent: Jan. 29, 2019

(54) STABLE LIQUID ANTIBODY FORMULATION

(75) Inventors: Advait Vijay Badkar, Chesterfield, MO (US); Leigh Kristen Bohack, Chesterfield, MO (US); Kevin Roger King, Chesterfield, MO (US); Alanta Lea Lary, Chesterfield, MO (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/119,784

(22) PCT Filed: Sep. 18, 2009

(86) PCT No.: PCT/IB2009/054111
§ 371 (c)(1),
(2), (4) Date: Mar. 18, 2011

(87) PCT Pub. No.: WO2010/032220
PCT Pub. Date: Mar. 25, 2010

(65) Prior Publication Data
US 2011/0171217 A1    Jul. 14, 2011

Related U.S. Application Data

(60) Provisional application No. 61/098,305, filed on Sep. 19, 2008.

(51) Int. Cl.
| A61K 39/395 | (2006.01) |
| A61K 9/00 | (2006.01) |
| A61K 31/198 | (2006.01) |
| A61K 47/18 | (2017.01) |
| A61K 47/26 | (2006.01) |

(52) U.S. Cl.
CPC .......... *A61K 9/0019* (2013.01); *A61K 31/198* (2013.01); *A61K 47/183* (2013.01); *A61K 47/26* (2013.01)

(58) Field of Classification Search
None
See application file for complete search history.

(56) References Cited

U.S. PATENT DOCUMENTS

2004/0228862 A1* 11/2004 Shelton et al. ............ 424/145.1

FOREIGN PATENT DOCUMENTS

| WO | 2004058184 | 7/2004 | |
| WO | WO 04058184 | 7/2004 | |
| WO | 2005019266 | 3/2005 | |
| WO | WO 05019266 | 3/2005 | ............ C07K 16/00 |
| WO | 2006096461 | 9/2006 | |
| WO | 2006096488 | 9/2006 | |
| WO | 2006096489 | 9/2006 | |
| WO | 2006096490 | 9/2006 | |
| WO | 2006096491 | 9/2006 | |
| WO | WO 06096461 | 9/2006 | |
| WO | WO 06096488 | 9/2006 | .......... A61K 39/395 |
| WO | WO 06096489 | 9/2006 | |
| WO | WO 06096490 | 9/2006 | |
| WO | WO 06096491 | 9/2006 | .......... A61K 39/395 |
| WO | 2006110883 | 10/2006 | |
| WO | WO 06110883 | 10/2006 | |

OTHER PUBLICATIONS

International Search Report for PCT/IB/2009/054111 dated Feb. 9, 2010.
International Search Report; PCT/IB2009/054111; dated Sep. 9, 2010; 10 pages.

* cited by examiner

*Primary Examiner* — Yunsoo Kim

(57) ABSTRACT

The present invention relates generally to the field of pharmaceutical formulations of antibodies. Specifically, the present invention relates to a stable liquid antibody formulation and its pharmaceutical preparation and use. This invention is exemplified by a liquid formulation of a humanized anti-NGF antibody.

13 Claims, 6 Drawing Sheets
Specification includes a Sequence Listing.

STABLE LIQUID ANTIBODY FORMULATION

This application is a national stage application under 35 U.S.C. 371 of PCT/IB2009/05411, filed on Sep. 18, 2009, which claims the benefit of U.S. Patent Application No. 61/098,305, filed on Sep. 19, 2008.

FIELD OF THE INVENTION

The present invention relates to the field of pharmaceutical formulations of antibodies. Specifically, the present invention relates to a stable liquid antibody formulation and its pharmaceutical preparation and use.

BACKGROUND OF THE INVENTION

Antibody preparations intended for therapeutic or prophylactic use require stabilizers to prevent loss of activity or structural integrity of the protein due to the effects of denaturation, oxidation or aggregation over a period of time during storage and transportation prior to use. These problems are exacerbated at the high concentrations of antibody often desired for therapeutic administration.

A major aim in the development of antibody formulations is to maintain antibody, solubility, stability and potency of its antigen binding. It is particularly desirable to avoid aggregates and particulates in solution which would require sterile filtration before use for intravenous or subcutaneous injection and limit route of administration. Antibody aggregates can cause pain and anaphylactoid side effects when the formulation containing them is intravenously injected.

Lyophilisation and freeze drying are alternatives to the liquid formulation of antibodies. Both processes have a propensity for inducing denaturation of the antibody and decreasing of its antigen-binding activity particularly upon reconstitution.

Salts, surfactants, pH and tonicity agents such as sugars can contribute to overcoming aggregation problems. Formulation of antibody preparations requires careful selection of these factors among others to avoid denaturation of the protein and loss of antigen-binding activity. Regarding a pH range of an antibody preparation, if an antibody formulation having a low pH value is intravenously injected pain or injection often occurs. Where an antibody formulation is used as an injection, it is desirable to have a pH value in an approximately neutral pH range, it is also advantageous to minimise surfactant levels to avoid bubbles in the formulation which are detrimental for injection into subjects.

A liquid formulation of monoclonal anti-CTLA4 antibody is known from WO2006/096491 (Pharmacia and Upjohn Company), and comprises 20 mg/ml antibody, 20 mM histidine buffer, 84 mg/ml trehelose, 0.2 mg/ml PS80 surfactant, 0.05 mg/ml EDTA pH 5.5.

There is a need for a stable liquid antibody formulation which stably supports high concentrations of bioactive antibody in solution and is suitable for parenteral administration, including intravenous intramuscular, intraperitoneal, intradermal or subcutaneous injection. It is further desirable that the formulation has minimised risk of bubble formation and anaphylactoid side effects.

Furthermore there is a need to provide such a stable liquid formulation for an anti-NGF antibody. NGF is known to play a central role in the development and maintenance of both peripheral and central neurons. In addition to its effects in the nervous system, increased NGF levels has been linked to a variety of inflammatory conditions including systemic lupus erythematosus, multiple sclerosis, psoriasis, arthritis, interstitital cystitis and asthma. NGF also has a demonstrated activity in a variety of pain conditions. It has been shown that the anti-NGF antibody E3 is useful in the treatment of acute and chronic pain conditions including, cancer pain, rheumatoid arthritis pain, osteoarthritis pain and post-surgical pain also (see for example WO2004/058184). There is a need for a stable liquid antibody preparation of an anti-NGF antibody to meet the medical need of patients suffering from inflammatory and pain conditions mediated by NGF.

BRIEF SUMMARY OF THE INVENTION

In one aspect, the present invention provides a liquid composition comprising; at least one antibody, at least one tonicity agent, at least one buffer, at least one chelating agent, at least one surfactant, wherein the pH of said composition is from 5.0 to 7.5.

In one aspect, the present invention provides a liquid composition comprising; at least one antibody, at least one tonicity agent, at least one buffer, at least one chelating agent, at least one surfactant, wherein the pH of said composition is from 5.8 to 6.8

The present invention also provides a liquid composition consisting of, or consisting essentially of; at least one antibody, at least one tonicity agent, at least one buffer, at least one chelating agent, at least one surfactant, wherein the pH of said composition is from 5.8 to 6.8.

The liquid composition according to the present invention provides the advantages that it stably supports high concentrations of bioactive antibody in solution and is suitable for parenteral administration, including intravenous, intramuscular, intraperitoneal, intradermal or subcutaneous injection. Also it has minimised risk of bubble formation and anaphylactoid side effects.

According to a preferred embodiment of the present invention the liquid composition can comprise at least one antibody. In some embodiments, more than one antibody may be present. At least one, at least two, at least three, at least four, at least five, or more, different antibodies can be present. Generally, the two or more different antibodies have complementary activities that do not adversely affect each other. The, or each, antibody can also be used in conjunction with other agents that serve to enhance and/or complement the effectiveness of the antibodies.

According to a preferred embodiment of the present invention the pH can be in the range 5.0 to 7.5, more preferably between about pH 7.5 and of any of about pH 5.1, 5.2, 5.3, 5.4 or 5.5. Further preferably the pH is in the range selected from between any one of pH 5.6, 5.7 or 5.8 and any one of about pH 7.5, 7.4, 7.3, 7.2, 7.1, 7.0, 6.9, 6.8, 6.7, 6.6, 6.5, 6.4, 6.3, 6.2, 6.1, 6.0, 5.9, 5.8 or 5.7.

In a preferred embodiment the pH can be in the range of between about pH 5.5 and any of about pH 6.0, 6.2, 6.5 or 6.8, alternatively the pH can be in the range of between about pH 5.8 and any of about pH 6.0, 6.2, 6.5 or 6.8.

More preferably the pH can be selected from pH values of any of about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4 or 7.5, most preferably the pH is pH 6.0+/−0.2. Values of pH in these ranges provides the liquid composition with enhanced protection from antibody aggregation and fragmentation and is close to physiological pH (about pH 7.2 to 7.4) for reduced risk of pain or anaphylactoid side effects on injection.

According to a further preferred embodiment of the present invention the tonicity agent preferably comprises a polyol, a saccharide, a carbohydrate, a salt, such as sodium chloride, or mixtures thereof. Preferably the polyol has a molecular weight that is less than about 600 kD (e.g., in the range from about 120 to about 400 kD), preferably selected from mannitol, trehalose, sorbitol, erythritol, isomalt, lactitol, maltitol, xylitol, glycerol, lactitol, propylene glycol, polyethylene glycol, inositol, or mixtures thereof. Preferably the saccharide or carbohydrate is selected from the group of monosaccharides, disaccharides and polysaccharides or mixtures thereof. Preferably the saccharide or carbohydrate is selected from the group consisting of fructose, glucose, mannose, sucrose, sorbose, xylose, lactose, maltose, sucrose, dextran, pullulan, dextrin, cyclodextrins, soluble starch, hydroxyethyl starch, water-soluble glucans, and mixtures thereof. Preferably the tonicity agent comprises a saccharide selected from the group of reducing sugar or non reducing sugar or mixtures thereof. Further preferably the tonicity agent comprises a saccharide which is a non-reducing sugar, preferably selected from the group consisting of sucrose, trehalose, and mixtures thereof. Most preferably the tonicity agent comprises trehalose, preferably trehalose dihydrate. According to the present invention the tonicity agent, particularly trehalose, preferably trehalose dihydrate, provides the liquid composition with enhanced antibody stability and resistance to aggregation, oxidation and fragmentation during refrigerated storage, e.g. 0 to 10° C., particularly 5 to 8° C., more particularly 5° C., or frozen storage and in cycles of freezing and thawing. Trehalose is particularly advantageous as the resulting antibody formulation does not suffer glycation.

The concentration of the tonicity agent in the liquid composition ranges from about 1 mg/ml to about 300 mg/ml, from about 1 mg/ml to about 200 mg/ml, or from about 1 mg/ml to about 100 mg/ml. Preferably the concentration of the tonicity agent in the liquid composition is about 60 mg/ml, about 65 mg/ml, about 70 mg/ml, about 75 mg/ml, about 80 mg/ml, about 81 mg/ml, about 82 mg/ml, about 83 mg/ml, about 84 mg/ml, about 85 mg/ml, about 86 mg/ml, about 87 mg/ml, about 88 mg/ml, about 89 mg/ml, about 90 mg/ml, about 91 mg/ml, about 92 mg/ml, about 93 mg/ml, about 94 mg/ml, about 95 mg/ml, about 96 mg/ml, about 97 mg/ml, about 98 mg/ml, about 99 mg/ml, about 100 mg/ml, about 105 mg/ml, about 110 mg/ml, about 120 mg/ml, or about 130 mg/ml. Most preferably the concentration of the tonicity agent in the liquid composition is about 84 mg/ml.

Where the tonicity agent comprises a salt, the concentration of the salt in the liquid composition ranges from about 1 mg/ml to about 20 mg/ml. Salts that are pharmaceutically acceptable and suitable for this invention include sodium chloride, sodium succinate, sodium sulfate, potassium chloride, magnesium chloride, magnesium sulfate, and calcium chloride. Preferred salts for this invention are sodium chloride and magnesium chloride, magnesium chloride may also improve the antibody stability by protecting the protein from deamidation. Preferably the salt in the liquid composition is selected from a range of concentrations of any of about 1 mg/ml, 2 mg/ml, 3 mg/ml, 4 mg/ml, 5 mg/ml, 6 mg/ml, 7 mg/ml, 8, mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml and 20 mg/ml.

According to a preferred embodiment of the present invention the surfactant is preferably selected from the group consisting of polysorbates, poloxamers, tritons, sodium dodecyl sulfate, sodium laurel sulfate, sodium octyl glycoside, lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine, myristamidopropyl-dimethylamine, palmidopropyl-dimethylamine, isostearamidopropyl-dimethylamine, sodium methyl cocoyl-taurate, disodium methyl oleyl-taurate, dihydroxypropyl PEG 5 linoleammonium chloride, polyethylene glycol, polypropylene glycol, and mixtures thereof. Further preferably the surfactant is selected from the group consisting of polysorbate 20, polysorbate 21, polysorbate 40, polysorbate 60, polysorbate 61, polysorbate 65, polysorbate 80, polysorbate 81, polysorbate 85, and mixtures thereof. More preferably the surfactant is selected from polysorbate 20, polysorbate 80, PEG3350, or mixtures thereof. Most preferably the surfactant is polysorbate 20. According to the present invention the surfactant, particularly polysorbate 20, provides the liquid composition with enhanced antibody stability and resistance to aggregation and fragmentation.

The concentration of the surfactant generally ranges from about 0.01 mg/ml to about 10 mg/ml, from about 0.01 mg/ml to about 5.0 mg/ml, from about 0.01 mg/ml to about 2.0 mg/ml, from about 0.01 mg/ml to about 1.5 mg/ml, from about 0.01 mg/ml to about 01.0 mg/ml, from about 0.01 mg/ml to about 0.5 mg/ml, from about 0.01 mg/ml to about 0.4 mg/ml, from about 0.01 mg/ml to about 0.3 mg/ml, from about 0.01 mg/ml to about 0.2 mg/ml, from about 0.01 mg/ml to about 0.15 mg/ml, from about 0.01 mg/ml to about 0.1 mg/ml, or from about 0.01 mg/ml, to about 0.05 mg/ml. Further preferably the concentration of the surfactant is about 0.5 mg/ml, about 0.05 mg/ml about 0.06 mg/ml about 0.07 mg/ml about 0.08 mg/ml about 0.09 mg/ml about 0.1 mg/ml about 0.11 mg/ml about 0.12 mg/ml about 0.13 mg/ml about 0.14 mg/ml about 0.15 mg/ml about 0.16 mg/ml about 0.17 mg/ml about 0.18 mg/ml about 0.19 mg/ml about 0.2 mg/ml. Most preferably the concentration of the surfactant is about 0.1 mg/ml. Embodiments with the concentration of the surfactant of about 0.1 mg/ml are highly preferred as this concentration permits maintenance of the stability of the antibody of the formulation in solution whilst also reducing the tendency for the formation of bubbles in the formulation during preparation of the formulation, handling of the formulation and preparation for parenteral administration and especially from stress related to shaking and agitation during preparation and also during shipping.

According to a preferred embodiment of the present invention the buffer can be selected from the group consisting of acetate, succinate, gluconate, citrate, histidine, acetic acid, phosphate, phosphoric acid, ascorbate, tartaric acid, maleic acid, glycine, lactate, lactic acid, ascorbic acid, imidazole, bicarbonate and carbonic acid, succinic acid, sodium benzoate, benzoic acid, gluconate, edetate, acetate, malate, imidazole, tris, phosphate, and mixtures thereof. Preferably the buffer is histidine, wherein the histidine can comprise either L-histidine or D-histidine, a solvated form of histidine, a hydrated form (e.g., monohydrate) of histidine, or an anhydrous form of histidine or a mixture thereof.

According to the present invention the buffer, particularly the preferred buffer histidine, provides the liquid composition with a pH close to physiological pH for reduced risk of pain or anaphylactoid side effects on injection and also provides enhanced antibody stability and resistance to aggregation, oxidation and fragmentation.

The concentration of the buffer can range from about 0.1 millimolar (mM) to about 100 mM. Preferably, the concentration of the buffer is from about 0.5 mM to about 50 mM, further preferably about 1 mM to about 30 mM, more preferably about 1 mM to about 18 mM, increasingly preferably about 1 mM to about 15 mM. Preferably, the concentration of the buffer is about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 30 mM, about 35 mM, about 40 mM, about 45 mM or about 50 mM. Most preferably the concentration of the buffer is about 10 mM.

According to a preferred embodiment of the present invention the chelating agent can be selected from the group consisting of, aminopolycarboxylic acids, hydroxyaminocarboxylic acids, N-substituted glycines, 2-(2-amino-2-oxoethyl) aminoethane sulfonic acid (BES), deferoxamine (DEF), citric acid, niacinamide, and desoxycholates and mixtures thereof. Further preferably the chelating agent is selected from the group consisting of ethylenediaminetetraacetic acid (EDTA), diethylenetriamine pentaacetic acid 5 (DTPA), nitrilotriacetic acid (NTA), N-2-acetamido-2-iminodiacetic acid (ADA), bis(aminoethyl)glycolether, N,N,N', N'-tetraacetic acid (EGTA), trans-diaminocyclohexane tetraacetic acid (DCTA), glutamic acid, and aspartic acid, N-hydroxyethyliminodiacetic acid (HIMDA), N,N-bis-hydroxyethylglycine (bicine) and N-(trishydroxymethylmethyl) 10 glycine (tricine), glycylglycine, sodium desoxycholate, ethylenediamine; propylenediamine; diethylenetriamine; triethylenetetraamine (trien), ethylenediaminetetraaceto EDTA; disodium EDTA, calcium EDTA oxalic acid, malate, citric acid, citric acid monohydrate, and trisodium citrate-dihydrate, 8-hydroxyquinolate, amino acids, histidine, cysteine, methionine, peptides, polypeptides, and proteins and mixtures thereof. Further preferably the chelating agent is selected from the group consisting of salts of EDTA including dipotassium edetate, disodium edetate, edetate calcium disodium, sodium edetate, trisodium edetate, and potassium edetate; and a suitable salt of deferoxamine (DEF) is deferoxamine mesylate (DFM), or mixtures thereof. Chelating agents used in the invention can be present, where possible, as the free acid or free base form or salt form of the compound, also as an anhydrous, solvated or hydrated form of the compound or corresponding salt.

Most preferably the chelating agent is either disodium EDTA, calcium EDTA, most preferably disodium EDTA.

Particularly preferable is disodium EDTA as it provides the liquid composition with an enhanced antibody stability and/or resistance to aggregation.

The concentration of chelating agent generally ranges from about 0.01 mg/ml to about 50 mg/ml, from about 1 mg/ml to about 10.0 mg/ml, from about 15 mg/ml to about 5.0 mg/ml, from about 0.01 mg/ml to about 1.0 mg/ml, or from about 0.03 mg/ml to about 0.5 mg/ml. Further preferably concentration of chelating agent generally ranges from about 0.01 mM to about 2.0 mM, from about 0.01 mM to about 1.5 mM, from about 0.01 mM to about 0.5 mM, from about 0.01 mM to about 0.4 mM, from about 0.01 mM to about 0.3 mM, from about 0.01 mM to about 0.2 mM, from about 0.01 mM to about 0.15 mM, from about 0.01 mM to about 0.1 mM, from about 0.01 mM to about 0.09 mM, from about 0.01 mM to about 0.08 mM, from about 0.01 mM to about 007 mM, from about 0.01 mM to about 0.06 mM, from about 0.01 mM to about 0.05 mM, from about 0.01 mM to about 0.04 mM, from about 0.01 mM to about 0.03 mM, from about 0.01 mM to about 0.02 mM or from about 0.05 mM to about 0.01 mM. Preferably the concentration of chelating agent can be about 0.01 mg/ml, 0.02 mg/ml, 0.03 mg/ml, about 0.04 mg/ml, about 0.05 mg/ml, about 0.06 mg/ml, about 0.07 mg/ml, about 0.10 mg/ml, about 0.20 mg/ml. Further preferably the concentration of chelating agent is about 0.045 mg/ml, about 0.046 mg/ml, about 0.047 mg/ml, about 0.048 mg/ml, about 0.049 mg/ml, about 0.05 mg/ml, about 0.051 mg/ml, about 0.052 mg/ml, about 0.053 mg/ml, about 0.054 mg/ml, about 0.055 mg/ml, or about 0.056 mg/ml. Most preferably, the concentration of chelating agent is about 0.05 mg/ml.

Chelating agents can lower the formation of reduced oxygen species, reduce acidic species (e.g., deamidation) formation, reduce antibody aggregation, and/or reduce antibody fragmentation, and/or reduce antibody oxidation in the compositions of the present invention. Such chelating agents can reduce or prevent degradation of an antibody that is formulated in comparison to the antibody without the protection of a chelating agent.

Unless stated otherwise, the concentrations listed herein are those concentrations at ambient conditions, [i.e., at 25° C. and atmospheric pressure].

According to a preferred embodiment of the present invention the liquid composition can further comprise an antioxidant agent. Preferably the antioxidant is selected from the group comprising, methionine, sodium thiosulfate, catalase, and platinum.

The concentration of antioxidant generally ranges from about 0.01 mg/ml to about 50 mg/ml, from about 0.01 mg/ml to about 10.0 mg/ml, from about 0.01 mg/ml to about 5.0 mg/ml, from about 0.01 mg/ml to about 1.0 mg/ml, or from about 0.01 mg/ml to about 0.02 mg/ml. Preferably the concentration of antioxidant can be about 0.01 mg/ml, 0.02 mg/ml, 0.03 mg/ml, about 0.04 mg/ml, about 0.05 mg/ml, about 0.06 mg/ml, about 0.07 mg/ml, 0.08 mg/ml, 0.09 mg/ml about 0.10 mg/ml, 0.11 mg/ml, 0.12 mg/ml, 0.13 mg/ml, about 0.14 mg/ml, about 0.15 mg/ml, about 0.16 mg/ml, about 0.17 mg/ml, 0.18 mg/ml, 0.19 mg/ml about 0.20 mg/ml, about 0.25 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml. Most preferably, the concentration of antioxidant is about 0.01 mg/ml.

According to a further preferred embodiment of the present invention the liquid composition can further comprise a preservative. Preferably the preservative agent is selected from Phenol, m-cresol, benzyl alcohol, benzalkonium chloride, benzalthonium chloride, phenoxyethanol and methyl paraben.

The concentration of preservative generally ranges from about 0.001 mg/ml to about 50 mg/ml, from about 0.005 mg/ml to about 15.0 mg/ml, from about 0.008 mg/ml to about 12.0 mg/ml or from about 0.01 mg/ml to about 10.0 mg/ml. Preferably the concentration of preservative can be about 0.1 mg/ml, 0.2 mg/ml, 0.3 mg/ml, about 0.4 mg/ml, about 0.5 mg/ml, about 0.6 mg/ml, about 0.7 mg/ml, 0.8 mg/ml, 0.9 mg/ml about 1.0 mg/ml, 2.0 mg/ml, 3.0 mg/ml, about 4.0 mg/ml, about 5.0 mg/ml, about 6.0 mg/ml, about 7.0 mg/ml, 8.0 mg/ml, 9.0 mg/ml about 9.1 mg/ml, about 9.2 mg/ml, 9.3 mg/ml, 9.4 mg/ml, 9.5 mg/ml, 9.6 mg/ml, 9.7 mg/ml, 9.8 mg/ml, 9.9 mg/ml, 10.0 mg/ml. Most preferably, the concentration of preservative is about 0.1 mg/ml or 9.0 mg/mL.

According to an aspect of the present invention the liquid formulation does not contain an antioxidant.

According to an aspect of the present invention the liquid formulation does not contain a preservative.

According to preferred embodiment of the present invention the present invention the concentration of antibody can range from about 0.1 to about 200 mg/ml. Preferably the concentration of antibody is about 0.5 mg/ml, about 1 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml, about 7 mg/ml, about 7.5 mg/ml, about 8 mg/ml, about 8.5 mg/ml, about 9 mg/ml, about 9.5 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 60 mg/ml, about 70 mg/ml, about 80 mg/ml, about 90 mg/ml, about 100 mg/ml or about 110 mg/ml. Most preferably the concentration of antibody is less than or equal to about 50 mg/ml and may be selected from the group comprising about 2 mg/ml, about 2.5 mg/ml, about 5 mg/ml, about 10 mg/ml, about 19 mg/ml, about 20 mg/ml, 22 mg/ml and about 50 mg/ml.

The antibody is preferably selected from the group of; monoclonal antibodies, polyclonal antibodies, antibody fragments (e.g., Fab, Fab', F(ab')2, Fv, Fc, ScFv etc.), chimeric antibodies, bispecific antibodies, heteroconjugate antibodies, single chain (ScFv), mutants thereof, fusion proteins comprising an antibody portion (e.g., a domain antibody), humanized antibodies, human antibodies, and any other modified configuration of the immunoglobulin molecule that comprises an antigen recognition site of the required specificity, including glycosylation variants of antibodies, amino acid sequence variants of antibodies, and covalently modified antibodies. The antibody may be murine, rat, human, or any other origin (including chimeric or humanized antibodies). In some embodiments, the antibody can be human but is more preferably humanized. Preferably the antibody is isolated, further preferably it is substantially pure. Where the antibody is an antibody fragment this preferably retains the functional characteristics of the original antibody i.e. the ligand binding and/or antagonist or agonist activity.

According to a preferred embodiment of the present invention the antibody heavy chain constant region may be from any type of constant region, such as IgG, IgM, IgD, IgA, and IgE; and any isotypes, such as IgG1, IgG2, IgG3, and IgG4. Preferably the antibody is an IgG2 antibody.

According to the present invention, the antibody can comprise the human heavy chain IgG2a constant region. In some embodiments the antibody comprises the human light chain kappa constant region. In some embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in Eur. J. Immunol. (1999) 29:2613-2624; PCT publication No. WO099/58572; and/or UK Patent Application No. 9809951.8. In still other embodiments, the antibody comprises a human heavy chain IgG2a constant region comprising the following mutations: A330P331 to S330S331 (amino acid numbering with reference to the wildtype IgG2a sequence), Eur. J. Immunol. (1999) 29:2613-2624.

According to a preferred embodiment of the present invention, the antibody is an anti-NGF antibody that binds NGF (such as human NGF) with a high affinity. In some embodiments, high affinity is (a) binding NGF with a $K_D$ of less than about 2 nM (such as any of about 1 nM, 800 pM, 600 pM, 400 pM, 200 pM, 100 pM, 90 pM, 80 pM, 70 pM, 60 pM, 50 pM, 40 pM, 30 pM, 20 pM, 10 pM, 5 pM or less), and/or a $k_{off}$ of slower than about $6\times10^{-5}$ $s^{-1}$; and/or (b) inhibiting, (reducing, and/or blocking) human NGF-dependent survival of mouse E13.5 trigeminal neurons with an IC50 (in the presence of about 15 pM of NGF) of any of about 200 pM, 150 pM, 100 pM, 80 pM, 60 pM, 40 pM, 20 pM, 10 pM, or less; and/or (c) inhibiting (reducing, and/or blocking) human NGF-dependent survival of mouse E13.5 trigeminal neurons with an IC50 (in the presence of about 1.5 pM of NGF) of any of about 50 pM, 40 pM, 30 pM, 10 pM, 20 pM, 10 pM, 5 pM, 2 pM, 1 pM, or less; and/or (d) inhibiting (reducing, and/or blocking) rat NGF-dependent survival of mouse E13.5 trigeminal neurons with an IC50 (in the presence of about 15 pM of NGF) of any of about 150 pM, 125 pM, 100 pM, 80 pM, 60 pM, 40 pM, 30 pM, 20 pM, 10 pM, 5 pM, or less; and/or (e) inhibiting (reducing, and/or blocking) rat NGF-dependent survival of mouse E13.5 trigeminal neurons with an IC50 (in the presence of about 1.5 pM of NGF) of any of about 30 pM, 25 pM, 20 pM, 15 pM, 10 pM, 5 pM, 4 pM, 3 pM, 2 pM, 1 pM, or less; and/or (f) and/or bind NGF with higher affinity than does the trkA receptor.

In another aspect, the antibodies (a) bind NGF (such as human NGF) with a $K_D$ of less than about 2 nM (such as any of about 1 nM, 800 pM, 600 pM, 400 pM, 200 pM, 100 pM, 90 pM, 80 pM, 70 pM, 60 pM, 50 pM, 40 pM, 30 pM, 20 pM, 10 pM, 5 pM or less), and/or a $k_{off}$ of slower than about $6\times10^{-5}$ $s^{-1}$; and/or (b) inhibit human NGF-dependent survival of mouse E13.5 trigeminal neurons with an IC50 (in the presence of about 15 pM of NGF) of any of about 200 pM, 150 pM, 100 pM, 80 pM, 60 pM, 40 pM, 20 pM, 10 pM, or less; and/or (c) inhibit human NGF-dependent survival of mouse E13.5 trigeminal neurons with an IC50 (in the presence of about 1.5 pM of NGF) of any of about 50 pM, 40 pM, 30 pM, 10 pM, 20 pM, 10 pM, 5 pM, 2 pM, 1 pM, or less; and/or bind NGF with higher affinity than does the trkA receptor. In some embodiments, the antibodies (a) bind NGF with a $K_D$ of less than about 2 nM; and/or (b) inhibit human NGF-dependent survival of mouse E13.5 trigeminal neurons with an IC50 of about 100 pM or less, wherein the IC50 is measured in the presence of about 15 pM NGF; and/or (c) inhibit human NGF-dependent survival of mouse E13.5 trigeminal neurons with an IC50 of about 10 pM or less, wherein the IC50 is measured in the presence of about 1.5 pM of NGF. In some embodiments, the antibodies (a) bind NGF with a $K_D$ of less than about 100 pM; and/or (b) inhibit human NGF-dependent survival of mouse E13.5 trigeminal neurons with an IC50 of about 20 pM or less, wherein the IC50 is measured in the presence of about 15 pM NGF; and/or (c) inhibit human NGF-dependent survival of mouse E13.5 trigeminal neurons with an IC50 of about 2 pM or less, wherein the IC50 is measured in the presence of about 1.5 pM of NGF.

The epitope (s) that can be bound by the antibody can be continuous or discontinuous. In one embodiment, the antibody binds essentially the same hNGF epitopes as an antibody selected from the group consisting of MAb 911, MAb 912, and MAb 938 as described in Hongo et al., Hybridoma, 19: 215-227 (2000), an antibody defined herein (such as antibody E3); and/or described in WO2005019266 (including antibodies 4D4, 14D10, 6G9, 7H2, 14F11 and 4G6) or WO2006131951 (including antibody Hu-αD11), WO09023540 or US20090041717, the entire content of which are herein incorporated by reference. In another embodiment, the antibody binds essentially the same hNGF epitope as MAb 911. In still another embodiment, the antibody binds essentially the same epitope as MAb 909. Hongo et al., supra. For example, the epitope may comprise one or more of residues K32, K34 and E35 within variable region 1 (amino acids 23-35) of hNGF; residues F79 and T81 within variable region 4 (amino acids 81-88) of hNGF; residues H84 and K88 within variable region 4; residue R103 between variable region 5 (amino acids 94-98) of hNGF and the C-terminus (amino acids 111-118) of hNGF; residue E11 within pre-variable region 1 (amino acids 10-23) of hNGF; Y52 between variable region 2 (amino acids 40-49) of hNGF and variable region 3 (amino acids 59-66) of hNGF; residues L112 and S113 within the C-terminus of hNGF; residues R59 and R69 within variable region 3 of hNGF; or residues V18, V20, and G23 within pre-variable region 1 of hNGF. In addition, an epitope can comprise one or more of the variable region 1, variable region 3, variable region 4, variable region 5, the N-terminus region, and/or the C-terminus of hNGF. In still another embodiment, the antibody significantly reduces the solvent accessibility of residue R103 of hNGF. It is understood that although the epitopes described above relate to human NGF, one of ordinary skill can align the structures of human NGF with the NGF of other species and identify likely counterparts to these epitopes.

In one aspect, the invention provides polypeptides (such as an antibody), which comprise a heavy chain variable region comprising SEQ ID NO: 9, wherein I34 is S, L, V A, or I; and N35 is substituted with N, T or S. For convenience herein, "substituted" or "is" in this context or reference to an amino acid refers to choices of amino acid (s) for a given position. As is clear, the substitution, or choice, may be the amino acid depicted in a SEQ ID or Figure. Residue numbers are determined readily from reference to the SEQ ID NO stated and follow the residue numbering of the antibody.

In another aspect, the invention provides polypeptides (such as an antibody) which comprise a heavy chain variable region comprising SEQ ID NO: 10, wherein M50 is M, I, G, Q, S, or L; A62 is A, or S; and L63 is L or V.

In another aspect, the invention provides polypeptides (such as an antibody) which comprises a heavy chain variable region comprising SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D 109 is D, N, or G; and wherein Y110 is Y, K, S, R or T.

In another aspect, the invention provides polypeptides (such as an antibody) which comprise a heavy chain variable region comprising SEQ ID NO: 11, wherein Y 100 is Y, L, or R; wherein Y101 is Y or W; wherein G103 is G, A, or S; wherein T104 is T or S; wherein S 105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the invention provides polypeptides (such as an antibody) which comprise a heavy chain variable region comprising SEQ ID NO: 11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S 105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the invention provides polypeptides (such as an antibody) which comprise a light chain variable region comprising SEQ ID NO: 12, wherein S26 is S or F; D28 is D, S, A, or Y; and H32 is H, N, or Q.

In another aspect, the invention provides polypeptides (such as an antibody) which comprise a light chain variable region comprising SEQ ID NO: 13, wherein I51 is I, T, V or A; and S56 is S or T.

In another aspect, the invention provides polypeptides (such as an antibody) which comprise a light chain variable region comprising SEQ ID NO: 14, wherein S91 is S or E; K92 is K, H, R, or S; and wherein Y96 is Y or R.

In another aspect, the invention provides polypeptides (such as an antibody) which comprise a light chain variable region comprising SEQ ID NO: 14, wherein S91 is S or E; K92 is any amino acid; T93 is any amino acid; and wherein Y96 is Y or R.

In one aspect, the invention provides polypeptides (such as an antibody), which comprise an amino acid sequence shown in SEQ ID NO: 9, wherein I34 is S, L, V A, or I; and N35 is N, T or S.

In another aspect, the invention provides polypeptides (such as an antibody) which comprise an amino acid sequence shown in SEQ ID NO: 10, wherein M50 is M, I, G, Q, S, or L; A62 is A, or S; and L63 is L or V.

In another aspect, the invention provides polypeptides (such as an antibody) which comprise an amino acid sequence shown in SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; and wherein Y110 is Y, K, S, R or T.

In another aspect, the invention provides polypeptides (such as an antibody) which comprise an amino acid sequence shown in SEQ ID NO: 11, wherein Y100 is Y, L, or R; wherein Y101 is Y or W; wherein G103 is G, A, or S; wherein T104 is T or S; wherein S 105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the invention provides polypeptides (such as an antibody) which comprise an amino acid sequence shown in SEQ ID NO: 11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the invention provides polypeptides (such as an antibody) which comprise an amino acid sequence shown in SEQ ID NO: 12, wherein S26 is S or F; D28 is D, S, A, or Y; and H32 is H, N, or Q.

In another aspect, the invention provides polypeptides (such as an antibody) which comprise an amino acid sequence shown in SEQ ID NO: 13, wherein I51 is I, T, V or A; and S56 is S or T.

In another aspect, the invention provides polypeptides (such as an antibody) which comprise an amino acid sequence shown in SEQ ID NO: 14, wherein S91 is S or E; K92 is K, H, R, or S; and wherein Y96 is Y or R.

In another aspect, the invention provides polypeptides (such as an antibody) which comprise an amino acid sequence shown in SEQ ID NO: 14, wherein S91 is S or E; K92 is any amino acid; T93 is any amino acid; and wherein Y96 is Y or R.

In another aspect, the invention provides polypeptides (such an antibodies, including humanized antibodies) which comprise a heavy chain variable region comprising the CDR1 region of SEQ ID NO: 9, wherein I34 is S, L, V A, or I; and N35 is N, T or S; the CDR2 region of SEQ ID NO: 10, wherein M50 is M, I, G, Q, S, or L; A62 is A, or S; and L63 is L or V; and the CDR3 region of SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; wherein Y110 is Y, K, S, R or T. In some embodiments, the heavy chain variable region comprises the CDR3 region of SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; wherein Y110 is any amino acid. In other embodiments, the heavy chain variable region comprises the CDR3 region of SEQ ID NO: 11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In some embodiments, the polypeptide (such as an antibody) further comprises an antibody light chain variable region.

In another aspect, the invention provides polypeptides (such as an antibody) which comprise a light chain variable region comprising the CDR1 region of SEQ ID NO: 12, wherein S26 is S or F; D28 is D, S, A, or Y; and H32 is H, N, or Q; the CDR2 region of SEQ ID NO: 13, wherein I51 is I, T, V or A; and S56 is S or T; and the CDR3 region of SEQ ID NO: 14, wherein S91 is S or E; K92 is K, H, R, or S; and wherein Y96 is Y or R. In some embodiments, the light chain variable region comprises the CDR3 region of SEQ ID NO: 14, wherein S91 is S or E; K92 is any amino acid; T93 is any amino acid; and wherein Y96 is Y or R. In some embodiments, the polypeptide (such as an antibody) further comprises an antibody heavy chain.

In another aspect, the invention provides polypeptides (such as an antibody) which comprise (a) a heavy chain variable region comprising the CDR1 region of SEQ ID NO: 9, wherein I34 is S, L, V A, or I; and N35 is N, T or S; the CDR2 region of SEQ ID NO: 10, wherein M50 is M, I, G, Q, S, or L; A62 is A, or S; and L63 is L or V; and the CDR3 region of SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; wherein Y110 is Y, K, S, R or T; and (b) a light chain variable region comprising the CDR1 region of SEQ ID NO: 12, wherein S26 is S or F; D28 is D, S, A, or Y; and H32 is H, N, or Q; the CDR2 region of SEQ ID NO: 13, wherein I51 is I, T, V or A; and S56 is S or T; and the CDR3 region of SEQ ID NO: 14, wherein S91 is S or E; K92 is K, H, R, or S; and wherein Y96 is Y or R. In some embodiments, the light chain variable region comprises the CDR3 region of SEQ ID NO: 14, wherein S91 is S or E; K92 is any amino acid; T93 is any amino acid; and wherein Y96 is Y or R. In some embodiments, the heavy chain variable region comprises the CDR3 region of SEQ ID NO: 11, wherein Y100 is Y, L, or R; wherein Y101 is Y or W; wherein G103 is G, A, or S; wherein T104 is T or S; wherein S 105 is S, A, or T; wherein Y106 is Y, R, T, or M; wherein Y107 is Y or F; wherein F108 is F or W; wherein D109 is S, A, C, G, D, N, T, or G; wherein Y110 is any amino acid. In other embodiments, the heavy chain variable region comprises the CDR3 region of SEQ ID NO: 11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In some embodiments, the polypeptide further comprises an antibody light chain.

In another aspect, the invention provides polypeptides (such an antibody, including a humanized antibody) which comprise an amino acid sequence shown in SEQ ID NO: 9, wherein I34 is S, L, V A, or I; and N35 is N, T or S; an amino acid sequence shown in SEQ ID NO: 10, wherein M50 is M, I, G, Q, S, or L; A62 is A, or S; and L63 is L or V; and an amino acid sequence shown in SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; wherein Y110 is Y, K, S, R or T. In some embodiments, the polypeptide comprises an amino acid sequence shown in SEQ ID NO: 11, wherein Y100 is Y, L, or R; and wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In other embodiments, the polypeptide comprises an amino acid sequence shown in SEQ ID NO: 11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In some embodiments, the polypeptide (such as an antibody) further comprises an antibody light chain variable region.

In another aspect, the invention provides polypeptides (such as an antibody) which comprise an amino acid sequence shown in SEQ ID NO: 12, wherein S26 is S or F; D28 is D, S, A, or Y; and H32 is H, N, or Q; an amino acid sequence shown in SEQ ID NO: 13, wherein I51 is I, T, V or A; and S56 is S or T; and an amino acid sequence shown in SEQ ID NO: 14, wherein S91 is S or E; K92 is K, H, R, or S; and wherein Y96 is Y or R.

According to a further preferred embodiment of the present invention the antibody can be an anti-NGF antibody comprising a heavy chain variable region comprising:
(a) a CDR1 region shown in SEQ ID NO: 3;
(b) a CDR2 region shown in SEQ ID NO:4; and
(c) a CDR3 region shown in SEQ ID NO:5, 11, 56, 58, 60, 62, 64.

According to a further preferred embodiment of the present invention the antibody can be anti-NGF antibody comprising a light chain variable region comprising:

(a) a CDR1 region shown in SEQ ID NO: 6;
(b) a CDR2 region shown in SEQ ID NO:7; and
(c) a CDR3 region shown in SEQ ID NO:8, 14, 55, 57, 59, 61 or 63.

According to a preferred embodiment of the present invention the antibody can be an anti-NGF antibody comprising a heavy chain variable region comprising:
(a) a CDR1 region shown in SEQ ID NO: 3;
(b) a CDR2 region shown in SEQ ID NO:4; and
(c) a CDR3 region shown in SEQ ID NO:5.

According to the present invention the antibody can be anti-NGF antibody comprising a light chain variable region comprising:
(a) a CDR1 region shown in SEQ ID NO: 6;
(b) a CDR2 region shown in SEQ ID NO:7; and
(c) a CDR3 region shown in SEQ ID NO:8.

The anti-NGF antibody may further comprise a heavy chain variable region comprising:
(a) a CDR1 region shown in SEQ ID NO: 3;
(b) a CDR2 region shown in SEQ ID NO:4; and
(c) a CDR3 region shown in SEQ ID NO:5.

The anti-NGF antibody may comprise a heavy chain variable region comprising an amino acid sequence of any of at least about 80%, 85%, 90%, 91%, 92%, 93%, 94%, 95%, 96%, 97%, 98% or 99% identical to the amino acid sequence of SEQ ID No. 1 and/or a light chain variable region comprising an amino acid sequence of any of at least about 80%, 85%, 90%, 91%, 92%, 93%, 94%, 95%, 96%, 97%, 98% or 99% identical to the amino acid sequence of SEQ ID No. 2, wherein the antibody binds specifically to NGF.

The heavy chain variable region and/or light chain variable region of a humanised anti-NGF antibody may comprise one or more respective framework mutations. In one aspect the framework mutation may replace a human framework residue with the complementary mouse framework residue. The mutation may comprise the substitution V71K in the heavy chain variable region.

The anti-NGF antibody may comprise a heavy chain variable region comprising the amino acid sequence of SEQ ID NO: 1 and/or may comprise a light chain variable region comprising the amino acid sequence of SEQ ID NO: 2.

The anti-NGF antibody may be an antibody comprising the amino acid sequences shown in SEQ ID NOS: 1 and 2.

The anti-NGF antibody may comprise a heavy chain region comprising an amino acid sequence of any of at least about 80%, 85%, 90%, 91%, 92%, 93%, 94%, 95%, 96%, 97%, 98% or 99% identical to the amino acid sequence of SEQ ID No. 16 and/or a light chain region comprising an amino acid sequence of any of at least about 80%, 85%, 90%, 91%, 92%, 93%, 94%, 95%, 96%, 97%, 98% or 99% identical to the amino acid sequence of SEQ ID No. 17, wherein the antibody binds specifically to NGF.

The anti-NGF antibody may comprise a heavy chain region comprising the amino acid sequence of SEQ ID NO: 16 and/or may comprise a light chain region comprising the amino acid sequence of SEQ ID NO: 17.

The anti-NGF antibody may be an antibody comprising the amino acid sequences shown in SEQ ID NOS: 16 and 17.

The anti-NGF antibody may compete for NGF binding with an anti-NGF antibody as defined herein. The anti-NGF antibody may compete for NGF binding with an antibody comprising a heavy chain variable region comprising the amino acid sequence of SEQ ID NO: 1 and/or a light chain variable region comprising the amino acid sequence of SEQ ID NO: 2.

The anti-NGF antibody may be a humanized and affinity matured antibody, E3, which specifically binds human and rodent NGF. Antibody E3 is described in WO2004/058184, the content of which is hereby incorporated by reference in its entirety. The amino acid sequences of the heavy chain and light chain variable regions of E3 are shown in SEQ ID Nos. 1 and 2 (FIGS. 1A and 1B of WO2004/058184), respectively. The CDR portions of antibody E3 (including Chothia and Kabat CDRs) are diagrammatically depicted in FIGS. 1A and 1B of WO2004/058184. The amino acid sequences of E3 heavy and light chains, and of the individual extended CDRs are also shown below (See, "antibody sequences", below). Antibody E3 is highly potent in sequestering NGF and preventing interaction with its receptor. E3 and its murine precursor antibody 911 have been shown to be an effective analgesic in non-clinical animal models of pathological pain including arthritis, cancer pain and post surgical pain.

The anti-NGF antibody may also comprise a fragment or a region of the antibody E3 (interchangeably termed "E3" herein). In one embodiment, the fragment is a light chain of the antibody E3 as shown in FIG. 1B of WO2004/058184 and SEQ ID No. 17 herein. In another embodiment, the fragment is a heavy chain of the antibody E3 as shown in FIG. 1A of WO2004/058184 and SEQ ID No. 16 herein. In yet another embodiment, the fragment contains one or more variable regions from a light chain and/or a heavy chain of the antibody E3. In yet another embodiment, the fragment contains one or more CDRs from a light chain and/or a heavy chain of the antibody E3 as shown in FIGS. 1A and 1B of WO2004/058184 and SEQ ID Nos. 17 and 16, respectively, herein.

In another aspect, the antibody comprises a light chain that is encoded by a polynucleotide that is produced by a host cell with a deposit number of ATCC No. PTA-4893 or ATCC No. PTA-4894. In another aspect, the antibody comprises a heavy chain that is encoded by a polynucleotide that is produced by a host cell with a deposit number of ATCC No. PTA-4895. In another aspect, the antibody comprises (a) a light chain that is encoded by a polynucleotide that is produced by a host cell with a deposit number of ATCC No. PTA-4894 or ATCC No. PTA-4893; and (b) a heavy chain that is encoded by a polynucleotide that is produced by a host cell with a deposit number of ATCC No. PTA-4895 (for convenience herein, the polynucleotide(s) produced by a deposited host cell are referred to as having a deposit number of ATCC NOs PTA-4894, PTA-4893 and PTA-4895). In another aspect, the antibody comprises a light chain variable region of a light chain that is encoded by a polynucleotide that is produced by a host cell with a deposit number of ATCC No. PTA-4894 or ATCC No. PTA-4893. In another aspect, the antibody comprises a heavy chain variable region of a heavy chain that that is encoded by a polynucleotide that is produced by a host cell with a deposit number of ATCC No. PTA-4895. In another aspect, the antibody comprises (a) a light chain variable region of a light chain that is encoded by a polynucleotide that is produced by a host cell with a deposit number of ATCC No. PTA-4894 or ATCC No. PTA-4893, and (b) a heavy chain variable region of a heavy chain that that is encoded by a polynucleotide that is produced by a host cell with a deposit number of ATCC No. PTA-4895. In still another aspect, the antibody comprises one or more CDR(s) encoded by (a) a polynucleotide that is produced by a host cell with a deposit number of ATCC No. PTA-4894; and/or (b) a heavy chain that is encoded by a polynucleotide that is produced by a host cell with a deposit number of ATCC No. PTA-4895.

In another aspect, the antibody comprises any one or more of the following: a) one or more CDR(s) of antibody E3 shown in SEQ ID Nos. 1-8 or SEQ ID Nos. 3-8 (FIGS. 1A and 1B of WO2004/058184); b) CDR H3 from the heavy chain of antibody E3 shown in SEQ ID No. 1 and 5 (FIG. 1A of WO2004/058184); c) CDR L3 from the light chain of antibody E3 shown in SEQ ID No. 2 and 8 (FIG. 1B of WO2004/058184); d) three CDRs from the light chain of antibody E3 shown in SEQ ID No. 2, 6-8 (FIG. 1B of WO2004/058184); e) three CDRs from the heavy chain of antibody E3 shown in SEQ ID Nos. 1, 3-5 (FIG. 1A of WO2004/058184); and f) three CDRs from the light chain and three CDRs from the heavy chain, of antibody E3 shown in SEQ ID Nos. 1-8 (FIGS. 1A and 1B of WO2004/058184). In another aspect, the antibody may comprise any one or more of the following: a) one or more (one, two, three, four, five, or six) CDR(s) derived from antibody E3 shown in SEQ ID Nos. 1-8 (FIGS. 1A and 1B of WO2004/058184); b) a CDR derived from CDR H3 from the heavy chain of antibody E3 shown in SEQ ID Nos. 1 and 5 (FIG. 1A of WO2004/058184); and/or c) a CDR derived from CDR L3 from the light chain of antibody E3 shown in SEQ ID Nos. 2 and 8 (FIG. 1B of WO2004/058184). In some embodiments, the CDRs may be Kabat CDRs, Chothia CDRs, or a combination of Kabat and Chothia CDRs (termed "extended" or "combined" CDRs herein). In some embodiments, the polypeptides comprise any of the CDR configurations (including combinations, variants, etc.) described herein.

In another embodiment the antibody may comprise:
(a) a heavy chain variable region comprising:
(i) a CDR1 region of SEQ ID NO: 30;
(ii) a CDR2 region comprising the sequence of SEQ ID NO: 31;
(iii) a CDR3 region selected from the group consisting of SEQ ID NO: 11, 56, 58, 60, 62 and 64; and
(b) a light chain variable region comprising:
(i) a CDR1 region of SEQ ID NO: 18;
(ii) a CDR2 region of SEQ ID NO: 19;
(iii) a CDR3 region selected from the group consisting of SEQ ID NO: 14, 55, 57, 59, 61 and 63.

In some embodiments of the present invention the C-terminal lysine of the heavy chain of any of the anti-NGF antibodies described herein is deleted. In various cases the heavy and/or light chain of the anti-NGF antibodies described herein may optionally include a signal sequence.

In another embodiment, the antibody may be selected from an anti-NGF antibody known in the art, such as antibodies described in WO2005019266 (including antibodies 4D4, 14D10, 6G9, 7H2, 14F11 and 4G6), WO2006131951 (including antibody Hu-αD11), WO09023540 or US20090041417. The antibody may bind to the same epitope as an anti-NGF antibody known in the art, such as Mab911, MAb 912, and MAb 938 as described in Hongo et al., Hybridoma, 19: 215-227 (2000), and antibodies described in WO2005019266 (including antibodies 4D4, 14D10, 6G9, 7H2, 14F11 and 4G6), WO2006131951 (including antibody Hu-αD11), WO09023540 or US20090041417 and/or may compete for binding to NGF with such an antibody.

According to a further aspect of the present invention there is provided a liquid composition comprising or consisting of;
about 0.5 mg/ml to about 50 mg/ml of at least one antibody,
about 1.0 mM to about 15 mM histidine buffer,
about 1 mg/ml to about 100 mg/ml trehalose dihydrate,
about 0.01 to about 0.15 mg/ml PS20,
about 0.01 to about 0.1 mg/ml. disodium EDTA,
wherein said composition is of a pH selected from the range of between about pH 5.5 and any of about pH 6.0, 6.2, 6.5 or 6.8, or alternatively from the range of between about pH 5.8 and any of about pH 6.0, 6.2, 6.5 or 6.8.

According to a further aspect of the present invention there is provided a liquid composition comprising or consisting of;
any of about 2.5 mg/ml, 5 mg/ml, 10 mg/ml, 20 mg/ml, 22 mg/ml or about 50 mg/ml of at least one antibody,
about 1.0 mM to about 15 mM histidine buffer,
about 1 mg/ml to about 100 mg/ml trehalose dihydrate,
about 0.01 to about 0.15 mg/ml PS20,
about 0.01 to about 0.1 mg/ml. disodium EDTA,
wherein said composition is of a pH selected from the range of between about pH 5.5 and any of about pH 6.0, 6.2, 6.5 or 6.8, or alternatively from the range of between about pH 5.8 and any of about pH 6.0, 6.2, 6.5 or 6.8.

According to a preferred embodiment the liquid composition comprises or consists of;
any of about 2.5 mg/ml, 5 mg/ml, 10 mg/ml, 20 mg/ml, 22 mg/ml or about 50 mg/ml of at least one antibody,
about 10 mM histidine buffer,
about 84 mg/ml trehalose dihydrate,
about 0.1 mg/ml PS20,
about 0.05 mg/ml. disodium EDTA,
wherein said composition is of a pH selected from the range of between about pH 5.5 and any of about pH 6.0, 6.2, 6.5 or 6.8, or alternatively from the range of between about pH 5.8 and any of about pH 6.0, 6.2, 6.5 or 6.8, preferably is of a pH from 5.8 to 6.5, and wherein said antibody comprises a variable heavy chain sequence of SEQ ID NO. 1 and a variable light chain sequence of SEQ ID NO. 2.

According to a preferred embodiment the liquid composition comprises or consists of;
any of about 2.5 mg/ml, 5 mg/ml, 10 mg/ml, 20 mg/ml, 22 mg/ml or about 50 mg/ml of at least one antibody,
about 10 mM histidine buffer,
about 84 mg/ml trehalose dihydrate,
about 0.1 mg/ml PS20,
about 0.05 mg/ml. disodium EDTA,
wherein said composition is of pH 6.0, +/−0.2 and wherein said antibody comprises a variable heavy chain sequence of SEQ ID NO. 1 and a variable light chain sequence of SEQ ID NO. 2. In a preferred embodiment the dose volume used is 1 ml.

In one aspect there is provided a liquid composition which is not lyophilized and has not been subjected to lyophilization.

According to a further aspect of the present invention there is provided a liquid composition of the invention wherein the composition is resistant to aggregation of the antibody after multiple freeze thaw cycles.

Preferably the antibody is resistant to aggregation during at least one cycle of freezing and thawing of the composition, further preferably wherein the antibody is resistant to aggregation during multiple freeze thaw cycles, preferably during at least 2, 3, 4, 5, 6, 7, 8, 9, 10, 11, 12, 13, 14 or 15 cycles of freeze thawing. Most preferably the antibody is resistant to aggregation during at least fifteen cycles of freezing and thawing of the liquid composition, further preferably four or fifteen cycles.

Further preferably the antibody demonstrates less than about 10% aggregation increase after the multiple freeze thaw cycles of the liquid composition in comparison to the same composition, or an equivalent sample of identical or about identical composition, prior to freeze thawing, more preferably less than or about, 9, 8, 7, 6, 5, 4, 3, 2, 1, 0.5 or 0% aggregation increase after the multiple freeze thaw cycles of the liquid composition in comparison to the same composition, or an equivalent sample of identical or about identical composition, prior to freeze thawing.

According to a further aspect of the present invention there is provided a liquid composition of the invention wherein the composition can be stored for a period of at least about 26 or 52 weeks at a temperature of any of about 5, 25 or 40° C. and wherein there is less than about 35% further preferably less than about 10% increase in aggregation of the antibody of the composition. Preferably the concentration of the antibody is either about 10 mg/ml or about 50 mg/ml.

Preferably there is less than about 35% further preferably less than about 10% increase in aggregation of the antibody of the liquid formulation when stored for a period of any of about 2, 4, 8, 9, 13, 26 or 52 weeks at a temperature of any of about 5, 25 or 40° C. in comparison to the same composition, or an equivalent sample of identical or about identical composition, prior to the period of storage. Preferably the concentration of the antibody is either about 10 mg/ml or about 50 mg/ml.

Further preferably the antibody of the liquid composition demonstrates less than about 35% further preferably less than about 10% aggregation increase, further preferably less than any of about 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, more preferably less than about 8, 7, 6, 5, 4, 3, 2, 1, or 0.5% or equal to about 0% aggregation increase after the period of storage of 2, 4, 8, 9, 13, 26 or 52 weeks at a temperature of any of about 5, 25 or 40° C.; most preferably less than about 20% at 40° C. for 52 weeks, or less than about 10% at 40° C. for 26 weeks, in comparison to the same composition, or an equivalent sample of identical or about identical composition, prior to the period of storage. Preferably the concentration of the antibody is either about 10 mg/ml or about 50 mg/ml.

According to a further aspect of the present invention there is provided a liquid composition of the invention wherein the composition can be stored for a period of at least about 26 or 52 weeks at a temperature any of about 5, 25 or 40° C. and wherein there is less than about 35% further preferably less than about 10% increase in oxidation of the antibody of the composition in comparison to the same composition, or an equivalent sample of identical or about identical composition, prior to the period of storage. Preferably the concentration of the antibody is either about 10 mg/ml or about 50 mg/ml.

Preferably the antibody of the liquid composition demonstrates less than about 35% further preferably less than about 10% oxidation increase, further preferably less than any of about 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, more preferably less than about 8, 7, 6, 5, 4, 3, 2, 1 or 0.5% or equal to about 0% oxidation increase after the period of storage of any of about 2, 4, 8, 9, 13, 26 or 52 weeks at a temperature of any of about 5, 25 or 40° C., most preferably less than about 31% or 30% for 52 weeks, or less than about 11% or 10% at 40° C. for 26 weeks, in comparison to the same composition, or an equivalent sample of identical or about identical composition, prior to the period of storage. Preferably the concentration of the antibody is either about 10 mg/ml or about 50 mg/ml.

According to a further aspect of the present invention there is provided a liquid composition of the invention wherein the composition can be stored for a period of at least about 26 or 52 weeks at a temperature of any of about 5, 25 or 40° C. and wherein there is less than 30% decrease in activity of the antibody of the composition.

Preferably there is less than about 30% decrease in activity of the antibody of the liquid formulation, further preferably less than about 25%, further preferably 20% more preferably less than about 19, 18, 17, 16, 15, 14, 13, 12, 11, 10, 9, 8, 7, 6, 5, 4, 3, 2, 1, 0.5 or 0% decrease in activity of the antibody of the formulation when stored for a period of any of at least about 2, 4, 8, 13, or 26 weeks at a temperature of any of about 5, 25 or 40° C. in comparison to the same composition, or an equivalent sample of identical or about identical composition, prior to the period of storage. Preferably the concentration of the antibody is either about 10 mg/ml or about 50 mg/ml.

According to a further aspect of the present invention there is provided a liquid composition of the invention wherein the composition can be stored for a period of at least about 26 weeks at a temperature any of about 5, 25 or 40° C. and wherein there is less than about 15% increase in fragmentation of the antibody of the composition in comparison to the same composition, or an equivalent sample of identical or about identical composition, prior to the period of storage, preferably wherein the concentration of the antibody is either about 10 mg/ml or about 50 mg/ml. Preferably the antibody of the liquid composition demonstrates less than about 15% further preferably further preferably less than any of about 14%, 13%, 12%, 11%, 10%, 9%, 8%, 7%, 6%, 5%, 4%, 3%, 2%, 1% or 0.5% or equal to about 0% fragmentation increase after the period of storage of any of about 2, 4, 8, 9, 13 or 26 weeks at a temperature of any of about 5, 25 or 40° C., most preferably less than about 14% at about 40° C. for about 26 weeks, in comparison to the same composition, or an equivalent sample of identical or about identical composition, prior to the period of storage. Preferably the concentration of the antibody is either about 10 mg/ml or about 50 mg/ml.

According to a further aspect of the present invention there is provided a liquid composition of the invention wherein the composition can stored for a period of at least about 52 weeks at a temperature of between 2 to 8° C., preferably 5° C. wherein there is less than 20% decrease in activity of the antibody of the composition. Preferably the concentration of antibody is any of about 2.5, 5, 10, 20 or 50 mg/ml.

Preferably there is less than about 15%, further preferably less than about 10% decrease in activity of the antibody of the liquid formulation when stored for a period of any of at least about 2, 4, 8, 13, 26 or 52 weeks, further preferably any of at least about 2, 3, 6, 9, 12, 18 or 24 months at a temperature of about 2 to 8° C., preferably 5° C. in comparison to the same composition, an equivalent sample of identical or about identical composition, prior to the period of storage. Preferably the concentration of antibody is any of about 2.5, 5, 10, 20 or 50 mg/ml.

Further preferably the antibody of the liquid composition demonstrates less than about 15% aggregation increase, further preferably less than about 10%, more preferably less than about 9, 8, 7, 6, 5, 4, 3, 2, 1, 0.5 or 0% activity decrease after the period of storage in comparison to the same composition, or an equivalent sample of identical or about identical composition, prior to the period of storage.

According to a further aspect of the present invention there is provided a liquid composition of the invention wherein the composition can stored for a period of at least about 52 weeks or at least 24 months at a temperature of between 2 to 8° C., preferably 5° C. wherein there is less than 20% increase in aggregation of the antibody of the composition. Preferably the concentration of antibody is any of about 2.5, 5, 10, 20 or 50 mg/ml.

Preferably there is less than about 15%, further preferably less than any of about 14, 13, 12, 11, 10, 9, 8, 7, 6, 5, 4, 3, 2, 1, 0.5% or equal to 0% increase in aggregation of the antibody of the liquid formulation when stored for a period of any of at least about 2, 4, 8, 13, 26 or 52 weeks, further preferably for any of at least about 2, 3, 6, 9, 12, 18 or 24 months at a temperature of about 2 to 8° C., preferably 5° C. in comparison to the same composition, an equivalent sample of identical or about identical composition, prior to the period of storage. Preferably the concentration of antibody is any of about 2.5, 5, 10, 20 or 50 mg/ml.

According to a further aspect of the present invention there is provided a liquid composition of the invention wherein the composition can stored for a period of at least about 52 weeks or at least 24 months at a temperature of between 2 to 8° C., preferably 5° C. wherein there is less than 20% increase in oxidation of the antibody of the composition. Preferably the concentration of antibody is any of about 2.5, 5, 10, 20 or 50 mg/ml.

Preferably there is less than about 15%, further preferably less than any of about 14, 13, 12, 11, 10, 9, 8, 7, 6, 5, 4, 3, 2, 1, 0.5% or equal to 0% increase in oxidation of the antibody of the liquid formulation when stored for a period of any of at least about 2, 4, 8, 13, 26 or 52 weeks, further preferably for any of at least about 2, 3, 6, 9, 12, 18 or 24 months at a temperature of about 2 to 8° C., preferably 5° C. in comparison to the same composition, an equivalent sample of identical or about identical composition, prior to the period of storage. Preferably the concentration of antibody is any of about 2.5, 5, 10, 20 or 50 mg/ml.

According to a further aspect of the present invention there is provided a liquid composition of the invention wherein the composition can stored for a period of at least about 52 weeks or at least 24 months at a temperature of between 2 to 8° C., preferably 5° C. wherein there is less than 20% increase in fragmentation of the antibody of the composition. Preferably the concentration of antibody is any of about 2.5, 5, 10, 20 or 50 mg/ml.

Preferably there is less than about 15%, further preferably less than any of about 14, 13, 12, 11, 10, 9, 8, 7, 6, 5, 4, 3, 2, 1, 0.5% or equal to 0% increase in fragmentation of the antibody of the liquid formulation when stored for a period of any of at least about 2, 4, 8, 13, 26 or 52 weeks, further preferably for any of at least about 2, 3, 6, 9, 12, 18 or 24 months at a temperature of about 2 to 8° C., preferably 5° C. in comparison to the same composition, an equivalent sample of identical or about identical composition, prior to the period of storage. Preferably the concentration of antibody is any of about 2.5, 5, 10, 20 or 50 mg/ml.

According to a further preferred aspect of the present invention there is provided a liquid composition, according to any foregoing aspect or embodiment, for the manufacture of a medicament for treatment of pain in a mammal.

Preferably the pain is selected from one or more of acute pain, chronic pain, neuropathic, inflammatory, nociceptive, mixed aetiology pain, hyperalgesia, allodynia, visceral pain, somatic pain and back pain.

According to a yet further embodiment of the invention there is provided a liquid composition, according to any foregoing aspect or embodiment, for the manufacture of a medicament for treatment of pain and/or lower urinary tract symptoms (LUTs) associated with interstitial cystitis and/or painful bladder syndrome and/or bladder pain syndrome, According to a yet further embodiment of the invention there is provided a liquid composition, according to any foregoing aspect or embodiment, for the manufacture of a medicament for treatment of pain and/or chronic prostatitis and/or chronic pelvic pain syndrome. According to another aspect there is provided a liquid composition, according to any foregoing aspect or embodiment, for the manufacture of a medicament for treatment of pain and/or other symptoms associated with endometriosis and or uterine fibroids.

Preferably the mammal is selected from rodents (such as mice, rats and rabbits, pets (such as cats, dogs and horses), farm animals (such as cows, sheep, pigs and goats), sport animals and/or pets (such as cats, dogs and horses), primates, more preferably a human.

According to a preferred embodiment the liquid composition can be administered directly into the blood stream, into muscle, into tissue, into fat, or into an internal organ. Suitable means for parenteral administration include intravenous, intraarterial, intraperitoneal, intrathecal, intraventricular, intraurethral, intrasternal, intracranial, intramuscular, intra-ossial, intradermal and subcutaneous. Suitable devices for parenteral administration include needle (including microneedle, microprojections, soluble needles and other micropore formation techniques) injectors, needle-free injectors and infusion techniques.

In some embodiments the administration pattern of the medicament comprises administration of a dose of the medicament once every week, once every two weeks, once every three weeks, once every four weeks, once every five weeks, once every six weeks, once every seven weeks, once every eight weeks, once every nine weeks, once every ten weeks, once every fifteen weeks, once every twenty weeks, once every twenty five weeks, or once every twenty six weeks. In some embodiments, the anti-NGF antagonist antibody is administered once every month, once every two months, once every three months, once every four months, once every five months, or once every six months. Most preferably the administration pattern of the medicament comprises administration of a dose of the medicament once every eight weeks.

In some embodiments the volume of a dose is less than or equal to about 20 ml, about 15 ml, about 10 ml, about 5 ml, about 2.5 ml, about 1.5 ml, about 1.0 ml, about 0.75 ml, about 0.5 ml, about 0.25 ml or about 0.01 ml.

In some embodiments the volume of a dose is about 20 ml, about 19 ml, about 18 ml, about 17 ml, about 16 ml, about 15 ml, about 14 ml, about 13 ml, about 12 ml, about 11 ml, about 10 ml, about 9 ml, about 8 ml, about 7 ml, about 6 ml, about 5 ml, about 4 ml, about 3 ml, about 2 ml or about 1 ml. Alternatively about 20.5 ml, about 19.5 ml, about 18.5 ml, about 17.5 ml, about 16.5 ml, about 15.5 ml, about 14.5 ml, about 13.5 ml, about 12.5 ml, about 11.5 ml, about 10.5 ml, about 9.5 ml, about 8.5 ml, about 7.5 ml, about 6.5 ml, about 5.5 ml, about 4.5 ml, about 3.5 ml, about 2.5 ml, about 1.5 ml, or about 0.5. Alternatively about 900 microliters, about 800 microliters, about 700 microliters, about 600 microliters, about 500 microliters, about 400 microliters, about 300 microliters, about 200 microliters, or about 100 microliters, alternatively about 950 microliters, about 850 microliters, about 750 microliters, about 650 microliters, about 550 microliters, about 450 microliters, about 350 microliters, about 250 microliters, about 150 microliters, or about 50 microliters. Most preferably the volume of the dose is less than or equal to about 2.5 ml.

According to preferred embodiment the concentration of antibody can range from about 0.1 to about 200 mg/ml. Preferably the concentration of antibody is about 0.5 mg/ml, about 1 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml, about 7 mg/ml, about 7.5 mg/ml, about 8 mg/ml, about 8.5 mg/ml, about 9 mg/ml, about 9.5 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 60 mg/ml, about 70 mg/ml, about 80 mg/ml, about 90 mg/ml, about 100 mg/ml or about 110 mg/ml. Most preferably the concentration of antibody is less than or equal to 50 mg/ml and may be selected from the group comprising about 2 mg/ml, about 2.5 mg/ml, about 5 mg/ml, about 10 mg/ml, about 19 mg/ml, about 20 mg/ml, about 22 mg.ml and about 50 mg/ml.

According to a preferred embodiment the dose contains less than or equal to about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 70 mg, about 80 mg, about 90 mg, about 100 mg, or about 110 mg of antibody. Most preferable the dose contains less than or equal to about 50 mg of antibody.

According to a preferred embodiment the dose contains an amount of antibody that is about 1 µg/kg, about 10 µg/kg, about 20 µg/kg, about 25 µg/kg, about 50 µg/kg, about 100 µg/kg, about 200 µg/kg, about 250 µg/kg, about 500 µg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, or about 11 mg/kg (of mass of the mammal to which the dose it to be administered). Most preferably the dose contains about 20 µg/kg, about 25 µg/kg, about 50 µg/kg, about 100 µg/kg, about 200 µg/kg, about 250 µg/kg, 1 mg/kg or about 2 mg/kg.

Dosage regimens may depend on the pattern of pharmacokinetic decay that the practitioner wishes to achieve. For example, in some embodiments, dosing from one-four times a week is contemplated. Even less frequent dosing may be used. In some embodiments, the dose is administered once every 2 weeks, every 3 weeks, every 4 weeks, every 5 weeks, every 6 weeks, every 7 weeks, every 8 weeks, every 9 weeks, every 10 weeks, every 15 weeks, every 20 weeks, every 25 weeks, or longer. In some embodiments, the dose is administered once every 1 month, every 2 months, every 3 months, every 4 months, every 5 months, every 6 months, or longer. Most preferably the dose is administered once every eight weeks. The progress of this therapy is easily monitored by conventional techniques and assays. The dosing regimen can vary over time.

For the purpose of the present invention, the appropriate dosage of the medicament will depend on the antibody employed, the type and severity of the pain to be treated, whether the agent is administered for preventative or therapeutic purposes, previous therapy, the patient's clinical history and response to the agent, and the discretion of the attending physician. Typically the clinician will administer the medicament, until a dosage is reached that achieves the desired result. Dosages may be determined empirically for example individuals are given incremental dosages to assess efficacy of the medicament, an indicator of pain may be followed, such as a change in a pain numerical rating scale (NRS).

Dose and/or frequency can vary over course of treatment. Empirical considerations, such as the antibody half-life, generally will contribute to the determination of the dosage. Frequency of administration may be determined and adjusted over the course of therapy, and is generally, but not necessarily, based on treatment and/or suppression and/or amelioration and/or delay of pain. In some individuals, more than one dose may be required. Frequency of administration may be determined and adjusted over the course of therapy. For repeated administrations over several days or longer, depending on the pain and its severity, the treatment is sustained until a desired suppression of symptoms occurs or until sufficient therapeutic levels are achieved to reduce pain.

Administration of medicament comprising the liquid composition can be continuous or intermittent, depending, for example, upon the recipient's physiological condition, whether the purpose of the administration is therapeutic or prophylactic, and other factors known to skilled practitioners. The administration of the medicament comprising the liquid composition may be essentially continuous over a preselected period of time or may be in a series of spaced dose, e.g., either before, during, or after developing pain.

Preferably the administration of the dose is a parenteral administration preferably selected from intravenous, intraarterial, intraperitoneal, intrathecal, intraventricular, intraurethral, intrasternal, intracranial, intramuscular, intra-ossial, intradermal and subcutaneous. Preferably the medicament is in a unit dosage sterile liquid form for parenteral administration.

Treatment efficacy can be assessed by monitoring pain relief. Pain relief may be characterized by time course of relief. Accordingly, in some embodiments, relief is observed within about 24 hours after administration. In other embodiments, relief is observed within about 36, 48, 60, 72 hours or 4 days after administration. In some embodiments, frequency and/or intensity of pain is diminished, and/or quality of life of those suffering pain is increased. In some embodiments, pain relief is provided for duration of at least about 7 days, at least about 14 days, at least about 21 days, at least about 28 days, at least about 35 days, at least about 42 days, at least about 49 days, at least about 56 days, at least about 63 days, at least about 70 days, at least about 77 days, at least about 84 days, at least about 180 days, or longer after a single dose of the medicament.

Combinations

The liquid composition, according to any aspect or embodiment may be usefully combined with another pharmacologically active compound, or with two or more other pharmacologically active compounds, particularly in the treatment of pain in a mammal and may be administered simultaneously, sequentially or separately in combination with one or more agents selected from:

(i) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(ii) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, or a pharmaceutically acceptable salt thereof;

(iii) a barbiturate sedative, e.g. amobarbital, aprobarbital, butabarbital, butabital, mephobarbital, metharbital, methohexital, pentobarbital, phenobartital, secobarbital, talbutal, theamylal or thiopental or a pharmaceutically acceptable salt thereof;

(iv) a benzodiazepine having a sedative action, e.g. chlordiazepoxide, clorazepate, diazepam, flurazepam, lorazepam, oxazepam, temazepam or triazolam or a pharmaceutically acceptable salt thereof;

(v) an $H_1$ antagonist having a sedative action, e.g. diphenhydramine, pyrilamine, promethazine, chlorpheniramine or chlorcyclizine or a pharmaceutically acceptable salt thereof;

(vi) a sedative such as glutethimide, meprobamate, methaqualone or dichloralphenazone or a pharmaceutically acceptable salt thereof;

(vii) a skeletal muscle relaxant, e.g. baclofen, carisoprodol, chlorzoxazone, cyclobenzaprine, methocarbamol or orphrenadine or a pharmaceutically acceptable salt thereof;

(viii) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinone or cis-4-(phosphonomethyl)-2-piperidinecarboxylic acid or a pharmaceutically acceptable salt thereof;

(ix) an alpha-adrenergic, e.g. doxazosin, tamsulosin, clonidine or 4-amino-6,7-dimethoxy-2-(5-methanesulfonamido-1,2,3,4-tetrahydroisoquinol-2-yl)-5-(2-pyridyl)quinazoline;

(x) a tricyclic antidepressant, e.g. desipramine, imipramine, amytriptiline or nortritiline;

(xi) an anticonvulsant, e.g. carbamazepine or valproate;

(xii) a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant or 3-[[2-methoxy-5-(trifluoromethoxy)phenyl]methylamino]-2-phenyl-piperidine (2S,3S);

(xiii) a muscarinic antagonist, e.g oxybutin, tolterodine, propiverine, tropsium chloride or darifenacin;

(xiv) a COX-2 inhibitor, e.g. celecoxib, rofecoxib or valdecoxib;

(xv) a non-selective COX inhibitor (preferably with GI protection), e.g. nitroflurbiprofen (HCT-1026);

(xvi) a coal-tar analgesic, in particular paracetamol;

(xvii) a neuroleptic such as droperidol;

(xviii) a vanilloid receptor agonist (e.g. resinferatoxin) or antagonist (e.g. capsazepine);

(xix) a beta-adrenergic such as propranolol;

(xx) a local anaesthetic, such as mexiletine;

(xxi) a corticosteriod, such as dexamethasone (xxii) a serotonin receptor agonist or antagonist;

(xxiii) a cholinergic (nicotinic) analgesic;

(xxiv) Tramadol (trade mark);

(xxv) a PDEV inhibitor, such as sildenafil, vardenafil or taladafil;

(xxvi) an alpha-2-delta ligand such as gabapentin or pregabalin; and (xxvii) a canabinoid.

DEFINITIONS

Figure 1:
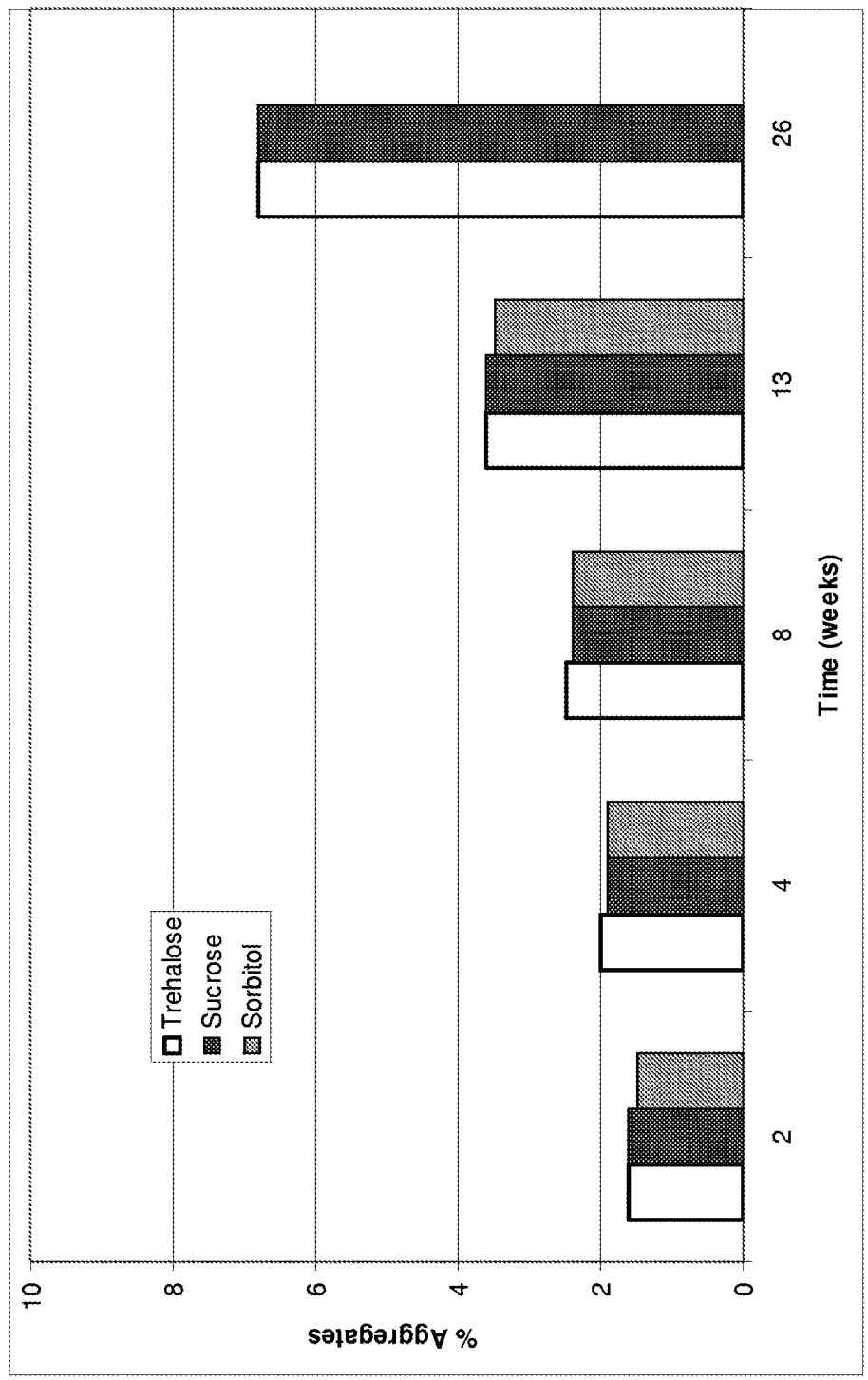
FIG. 1 Summary of % Aggregation (via SEC) Data from 50 mg/mL anti-NGF antibody: Tonicity Agent Screening Study at 40° C.

As used herein, the terms "formulation" or "composition" as they relate to an antibody are meant to describe the antibody in combination with a pharmaceutically acceptable excipient comprising at least one tonicity agent, at least one buffer, at least one chelating agent, at least one surfactant, wherein the pH is as defined.

The term "pharmaceutical composition" refers to preparations which are in such form as to permit the biological activity of the active ingredients to be effective.

"Pharmaceutically acceptable excipients" (vehicles, additives) are those, which can safely be administered to a subject to provide an effective dose of the active ingredient employed. The term "excipient" or "carrier" as used herein refers to an inert substance, which is commonly used as a diluent, vehicle, preservative, binder or stabilizing agent for drugs. As used herein, the term "diluent" refers to a pharmaceutically acceptable (safe and non-toxic for administration to a human) solvent and is useful for the preparation of the liquid formulations herein. Exemplary diluents include, but are not limited to, sterile water and bacteriostatic water for injection (BWFI).

As used herein, the term "antibody" refers to an intact antibody or an antigen-binding portion that competes with the intact antibody for specific binding. See generally, Fundamental Immunology, Ch. 7 (Paul, W., ed., 2nd ed. Raven Press, N.Y. (1989). Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies, diabodies and polypeptides that contain at least a portion of an antibody that is sufficient to confer specific antigen binding to the polypeptide. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342:878-883 (1989). As used herein, the term "polypeptide" encompasses native or artificial proteins, protein fragments and polypeptide analogs of a protein sequence. A polypeptide may be monomeric or polymeric.

As used herein, an Fd fragment means an antibody fragment that consists of the $V_H$ and CH1 domains; an Fv fragment consists of the $V_L$ and VH domains of a single arm of an antibody; and a dAb fragment (Ward et al., Nature 341:544-546 (1989)) consists of a $V_H$ domain.

The term "or an antigen-binding portion thereof" when used with the term "antibody" refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

As used herein, the term "monoclonal antibody" refers to a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

A single chain antibody (scFc) is an antibody in which VL and VH regions are paired to form a monovalent molecule via a synthetic linker that enables them to be made as a single protein chain (Bird et al Science, 242: 423-426 (1988) and Huston et al., Proc. Natl. Acad. Sci. USA, 85:5879-5883 (1988)).

Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

As used herein, the terms "E3", "3E", and "antibody E3" are used interchangeably to refer to an antibody comprising the amino acid sequence of the heavy chain and light chain variable regions shown in SEQ ID NO:1 and SEQ ID NO:2 (FIGS. 1A and 1B of WO2004/058184), respectively. The generation and characterization of E3 is described in the Examples of WO2004/058184, the entire content of which is herein incorporated by reference. In some embodiments, the term "E3" refers to immunoglobulin encoded by (a) a polynucleotide encoding E3 light chain that has a deposit number of ATCC No. PTA-4893 or ATCC No. PTA-4894, and (b) a polynucleotide encoding E3 heavy chain that has a deposit number of ATCC No. PTA-4895.

As used herein, the terms "isolated antibody" or "purified antibody" refers to an antibody that by virtue of its origin or source of derivation has one to four of the following: (1) is not associated with naturally associated components that accompany it in its native state, (2) is free of other proteins from the same species, (3) is expressed by a cell from a different species, or (4) does not occur in nature.

An antibody is "substantially pure," "substantially homogeneous," or "substantially purified" when at least about 60 to 75% of a sample exhibits a single species of antibody. A substantially pure antibody can typically comprise about 50%, 60%, 70%, 80% or 90% w/w of an antibody sample, more usually about 95%, and preferably will be over 99% pure. Antibody purity or homogeneity may tested by a number of means well known in the art, such as polyacrylamide gel electrophoresis or HPLC.

As used herein, the term "human antibody" is intended to include antibodies having variable and constant regions derived from human germline immunoglobulin sequences. This definition of a human antibody includes antibodies comprising at least one human heavy chain polypeptide or at least one human light chain polypeptide. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987). Other references describe rodent CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986). Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160.

As used herein, the term "recombinant antibody" is intended to include all antibodies that are prepared, expressed, created or isolated by recombinant means, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes or antibodies prepared, such recombinant human antibodies can be subjected to in vitro mutagenesis.

As used herein, the terms "is capable of specifically binding", "specifically binds", or "preferentially binds" refers to when an antibody binds to an antigen with a dissociation constant that is ≤1 µM, preferably ≤1 nM and most preferably ≤10 pM. An epitope that "specifically binds", or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody"specifically binds" or "preferentially binds" to a target if it binds with greater affinity, avidity, more readily, and/or with greater duration than it binds to other substances. For example, an antibody that specifically or preferentially binds to an NGF epitope is an antibody that binds this epitope with greater affinity, avidity, more readily, and/or with greater duration than it binds to other NGF epitopes or non-NGF epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein, the term "nerve growth factor" and "NGF" refers to nerve growth factor and variants thereof that retain at least part of the biological activity of NGF. As used herein, NGF includes all mammalian species of native sequence NGF, including human, canine, feline, equine, or bovine.

"NGF receptor" refers to a polypeptide that is bound by or activated by NGF. NGF receptors include the TrkA receptor and the p75 receptor of any mammalian species, including, but are not limited to, human, canine, feline, equine, primate, or bovine.

As used herein, an "anti-NGF antibody" (interchangeably termed "anti-NGF antagonist antibody") refers to an antibody which is able to bind to NGF and inhibit, block, antagonize, suppress or reduce NGF biological activity and/or downstream pathway(s) mediated by NGF signaling. In some embodiments the term "anti-NGF antagonist antibody" encompass all the previously identified terms, titles, and functional states and characteristics whereby the NGF itself, an NGF biological activity (including but not limited to its ability to ability to mediate any aspect of post-surgical pain), or the consequences of the biological activity, are substantially nullified, decreased, or neutralized in any meaningful degree. In some embodiments, an anti-NGF antagonist antibody binds NGF and prevent NGF dimerization and/or binding to an NGF receptor (such as p75 and/or trkA). In other embodiments, an anti-NGF antibody binds NGF and prevents trkA receptor dimerization and/or trkA autophosphorylation. Examples of anti-NGF antagonist antibodies are provided herein.

The term "identity" refers to the percent "identity" of two amino acid sequences or of two nucleic acid sequences. The percent identity is generally determined by aligning the sequences for optimal comparison purposes (e.g. gaps can be introduced in the first sequence for best alignment with the second sequence) and comparing the amino acid residues or nucleotides at corresponding positions. The "best alignment" is an alignment of two sequences that results in the highest percent identity. The percent identity is determined by comparing the number of identical amino acid residues or nucleotides within the sequences (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al (1990) J. Mol. Biol. 215:403-410 have incorporated such an algorithm. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search that detects distant relationships between molecules (Id.) When utilizing BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilized for the comparison of sequences is the algorithm of Myers and Miller, CABIOS (1989). The ALIGN program (version 2.0) which is part of the GCG sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

A "therapeutically effective amount" refers to an amount effective, at dosages and for periods of time necessary, to achieve the desired therapeutic result, which in the context of anti-NGF antibodies includes treatment or prophylactic prevention of the targeted pathologic condition for example inflammation or pain. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Likewise, a therapeutically effective amount of the antibody or antibody portion may vary according to factors such as the disease state, age, sex, and weight of the individual, the ability of the antibody or antibody portion to elicit a desired response in the individual, and the desired route of administration of the antibody formulation. A therapeutically effective amount is also one in which any toxic or detrimental effects of the antibody or antibody portion are outweighed by the therapeutically beneficial effects.

As used herein, the term "treatment" refers to both therapeutic treatment and prophylactic or preventative measures, wherein the object is to prevent or slow down (lessen) the targeted pathologic condition for example pain. Those in need of treatment include those already with the condition as well as those prone to have the condition or those in whom the condition is to be prevented. As used herein, "treatment" is an approach for obtaining beneficial or desired clinical results including, but not limited to, one or more of the following: including lessening severity, alleviation of one or more symptoms associated with pain, including any aspect of pain, (such as shortening duration of pain, reduction of pain sensitivity or sensation).

An "effective amount" of drug, compound, or pharmaceutical composition is an amount sufficient to effect beneficial or desired results including clinical results such as alleviation or reduction of the targeted pathologic condition for example pain sensation. An effective amount can be administered in one or more administrations. For purposes of this invention, an effective amount of drug, compound, or pharmaceutical composition is an amount sufficient to treat, ameliorate, reduce the intensity of the targeted pathologic condition for example inflammation or pain. In some embodiments, the "effective amount" may reduce pain at rest (resting pain) or mechanically-induced pain (including pain following movement), or both, and it may be administered before, during or after painful stimulus. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

"Pain" as used herein refers to pain of any etiology, including acute and chronic pain, and any pain with an inflammatory component. As used herein, "pain" includes nociception and the sensation of pain, and pain can be assessed objectively and subjectively, using pain scores and other methods well-known in the art. The pain can be primary or secondary pain, as is well-known in the art.

As used herein, the term "subject" for purposes of treatment includes any subject, and preferably is a subject who is in need of the treatment of the targeted pathologic condition for example inflammation or pain. For purposes of prevention, the subject is any subject, and preferably is a subject that is at risk for, or is predisposed to, developing the targeted pathologic condition for example inflammation or pain. The term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

When introducing elements of the present invention or the preferred embodiment(s) thereof, the articles "a", "an", "the" and "said" are intended to mean that there are one or more of the elements. The terms "comprising", "comprise", "comprises", "including" and "having" are intended to be inclusive and mean that there may be additional elements other than the listed elements.

As used herein, the term "polynucleotide" or "nucleic acid", used interchangeably herein, means a polymeric form of nucleotides either ribonucleotides or deoxynucleotides or a modified form of either type of nucleotide and may be single and double stranded forms. A "polynucleotide" or a "nucleic acid" sequence encompasses its complement unless otherwise specified. As used herein, the term "isolated polynucleotide" or "isolated nucleic acid" means a polynucleotide of genomic, cDNA, or synthetic origin or some combination thereof, which by virtue of its origin or source of derivation, the isolated polynucleotide has one to three of the following: (1) is not associated with all or a portion of a polynucleotide with which the "isolated polynucleotide" is found in nature, (2) is operably linked to a polynucleotide to which it is not linked in nature, or (3) does not occur in nature as part of a larger sequence.

As used herein, the term "chelating agent" is an excipient that can form at least one bond (e.g., covalent, ionic, or otherwise) to a metal ion. A chelating agent is typically a multidentate ligand that can be used in liquid compositions as a stabilizer to complex with species, which might otherwise promote instability.

As used herein, the term "buffer" refers to an added composition that allows a liquid antibody formulation to resist changes in pH, typically by action of its acid-base conjugate components. When a concentration of a buffer is referred to, it is intended that the recited concentration represent the molar concentration of the free acid or free base form of the buffer.

As used herein, the terms 'tonicity agent" or "tonicifier" refers to an excipient that can adjust the osmotic pressure of a liquid antibody formulation. In certain embodiments, the tonicity agent can adjust the osmotic pressure of a liquid antibody formulation to isotonic so that the antibody formulation is physiologically compatible with the cells of the body tissue of the subject. In still other embodiments, the "tonicity agent" may contribute to an improvement in stability of antibodies described herein. An "isotonic" formulation is one that has essentially the same osmotic pressure as human blood. Isotonic formulations generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood, Isotonicity can be measured using a vapor pressure or ice-freezing type osmometer, for example. The tonicity agent can be in an enantiomeric (e.g., L- or D-enantiomer) or racemic form; isomers such as alpha or beta, including alpha, alpha; or beta, beta; or alpha, beta; or beta, alpha; a free acid or free base form; a hydrated form (e.g., monohydrate), or an anhydrous form.

As used herein, the term "polyol" refers an excipient with multiple hydroxyl groups, and includes sugars (reducing and nonreducing sugars), sugar alcohols and sugar acids.

As used herein, the term "surfactant" refers to an excipient that can alter the surface tension of a liquid antibody formulation. In certain embodiments, the surfactant reduces the surface tension of a liquid antibody formulation. In still other embodiments, the "surfactant" may contribute to an improvement in stability of any of the antibody in the formulation. The surfactant may reduce aggregation of the formulated antibody and/or minimize the formation of particulates in the formulation and/or reduces adsorption. The surfactant may also improve stability of the antibody during and after a freeze/thaw cycle.

As used herein, the term "saccharide" refers to a class of molecules that are derivatives of polyhydric alcohols. Saccharides are commonly referred to as carbohydrates and may contain different amounts of sugar (saccharide) units, e.g., monosaccharides, disaccharides and polysaccharides.

As used herein, the term "reducing sugar" is one which contains a hemiacetal group that can reduce metal ions or react covalently with lysine and other amino groups in proteins and a "nonreducing sugar" is one which does not have these properties of a reducing sugar.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$K_{off}$", as used herein, is intended to refer to the off rate constant for dissociation of an antibody from the antibody/antigen complex.

The term "Kd", as used herein, is intended to refer to the dissociation constant of an antibody-antigen interaction. One way of determining the Kd or binding affinity of antibodies to NGF is by measuring binding affinity of monofunctional Fab fragments of the antibody. To obtain monofunctional Fab fragments, an antibody (for example, IgG) can be cleaved with papain or expressed recombinantly. The affinity of an anti-NGF Fab fragment of an antibody can be determined by surface plasmon resonance (BIAcore3000™ surface plasmon resonance (SPR) system, BIAcore, INC, Piscaway N.J.). CM5 chips can be activated with N-ethyl-N'-(3-dimethylaminopropyl)-carbodiimide hydrochloride (EDC) and N-hydroxysuccinimide (NHS) according to the supplier's instructions. Human NGF (or any other NGF) can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated $K_D$) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates (kon) and dissociation rates (koff) are obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any NGF, including human NGF, NGF of another vertebrate (in some embodiments, mammalian) (such as mouse NGF, rat NGF, primate NGF), as well as for use with other neurotrophins, such as the related neurotrophins NT3, NT4/5, and/or BDNF.

Anti-NGF antagonist antibodies for use in the invention can be identified or characterized using methods known in the art, whereby reduction, amelioration, or neutralization of an NGF biological activity is detected and/or measured. Methods described in PCT WO 04/065560 can be used. Another method, for example, a kinase receptor activation (KIRA) assay described in U.S. Pat. Nos. 5,766,863 and 5,891,650, can be used to identify anti-NGF agents.

Anti-NGF antagonist antibodies can also be identified by incubating a candidate agent, for example an antibody or anti-NGF antibody, with NGF and monitoring any one or more of the following characteristics: (a) binding to NGF and inhibiting NGF biological activity or downstream pathways mediated by NGF signaling function; (b) inhibiting, blocking or decreasing NGF receptor activation (including TrkA dimerization and/or autophosphorylation); (c) increasing clearance of NGF; (d) treating or preventing pain; (e) inhibiting (reducing) NGF synthesis, production or release. The ability of an anti-NGF antagonist antibody to block or neutralize a biological activity of NGF can also be assessed by monitoring the ability of the candidate agent to inhibit NGF mediated survival in the embryonic rat dorsal root ganglia survival bioassay as described in Hongo et al., Hybridoma 19:215-227 (2000).

"Reducing incidence" of pain means any of reducing severity (which can include reducing need for and/or amount of (e.g., exposure to) other drugs and/or therapies generally used for this conditions, including, for example, opiates), duration, and/or frequency (including, for example, delaying or increasing time to post-surgical pain in an individual). As is understood by those skilled in the art, individuals may vary in terms of their response to treatment, and, as such, for example, a "method of reducing incidence of rheumatoid arthritis pain or osteoarthritis pain in an individual" reflects administering the anti-NGF antagonist antibody based on a reasonable expectation that such administration may likely cause such a reduction in incidence in that particular individual.

"Ameliorating" a pain or one or more symptoms of a pain (such as rheumatoid arthritis pain or osteoarthritis pain) means a lessening or improvement of one or more symptoms of a pain as compared to not administering an anti-NGF antagonist antibody. "Ameliorating" also includes shortening or reduction in duration of a symptom.

"Palliating" a pain or one or more symptoms of a pain (such as rheumatoid arthritis pain or osteoarthritis pain) means lessening the extent of one or more undesirable clinical manifestations of post-surgical pain in an individual or population of individuals treated with an anti-NGF antagonist antibody in accordance with the invention.

As used therein, "delaying" the development of pain means to defer, hinder, slow, retard, stabilize, and/or postpone progression of pain, (such as post-surgical pain, rheumatoid arthritis pain, or osteoarthritis pain). This delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom is a method that reduces probability of developing the symptom in a given time frame and/or reduces. extent of the symptoms in a given time frame, when compared to not using the method. Such comparisons are typically based on clinical studies, using a statistically significant number of subjects.

"Pain" is taken to mean an unpleasant sensory and emotional experience associated with actual or potential tissue damage or described in terms of such damage. Pain can be divided into a number of different areas because of differing pathophysiology, these include nociceptive, inflammatory, neuropathic pain etc. It should be noted that some types of pain have multiple aetiologies and thus can be classified in more than one area, e.g. Back pain, Cancer pain have both nociceptive and neuropathic components.

"Chronic pain" as used herein is taken to mean pain associated with a chronic disorder, i.e. trauma, malignancy, disease, infection or pain that persists beyond resolution of such an underlying disorder, or healing of an injury, and that is often more intense than the underlying process or disorder would predict. Chronic pain may also be a "mixed aetiology pain" for example involving both nociceptive and/or neuropathic pain and/or inflammatory pain and/or cancer pain. As a consequence chronic pain is often unpredictable in response to analgesia. "Dual mechanism pain" is taken to mean pain that is amplified and maintained by both peripheral and central sensitization.

"Inflammatory pain" is taken to mean pain in response to tissue injury and the resulting inflammatory process. Inflammatory pain may originate in injured tissue that undergoes a reactive inflammatory process which may also affect neuronal function. Inflammatory pain may involve the binding of biochemical mediators ($PGE_2$, bradykinin, cytokines, and neuropeptides), to receptors on pain-transmitting neurons and alteration of their function, increasing their excitability and thus increasing pain sensation. Included in the term inflammatory pain are chronic and acute pain.

"Mixed aetiology pain" is taken to mean pain that contains both inflammatory and/or neuropathic and/or nociceptive components. "Dual mechanism pain" is taken to mean pain that is amplified and maintained by both peripheral and central sensitization.

"Neuropathic pain" is taken to mean pain produced by damage to or dysfunction of neurons in the peripheral or central nervous system.

"Acute pain" and "acute inflammatory pain" is taken to mean the normal, predictable, appropriate physiological response to a noxious chemical, thermal or mechanical stimulus or to a disease process that threatens or produces tissue injury which leads to the acute inflammation and acute inflammatory pain response, such acute pain often involves a nociceptive pain component. In general, the intensity of the acute pain is proportional to the intensity of the stimulus and persists as long as the stimulus persists, or until healing of tissue injury. Acute inflammatory pain is generally associated with injury, invasive procedures, trauma, infection, immune reaction, allergy, hypersensitivity and disease.

"Nociceptive pain" is taken to mean pain that is transmitted by nociceptors caused by noxious stimuli signalling tissue injury or impending tissue injury. Nociceptive pain involves transmission of pain signals via afferent neurons to the dorsal horn of the spinal cord, second order neurons transmit the signals to higher centres. Nociceptive pain normally resolves once the condition that precipitated it is resolved, also characteristic of acute pain.

"Hyperalgesia" is an extreme sensitivity to pain, often caused by damage to nociceptors in the body's soft tissues. It can be experienced in focal form is typically associated with injury, and is divided into two subtypes: (1) Primary hyperalgesia i.e. pain sensitivity that occurs directly in the damaged tissues, (2) secondary hyperalgesia i.e. pain sensitivity that occurs in surrounding undamaged tissues. It can also be experienced as a more diffuse, body-wide form. Hyperalgesia can be induced by an acute or chronic inflammatory condition. Key to the development of such hyperalgesia is the action of platelet aggregating factor (PAF) resulting from such an inflammatory condition or from an allergic response and which occurs via immune cells interacting with the peripheral nervous system and releasing cytokines and chemokines which lead to pain. Inflammatory conditions can induce the stimulation of pain fibres in a pattern consistent with a form of amplification in the spinal cord called long term potentiation, such amplification in the spinal cord provides a pathway producing hyperalgesia.

"Allodynia" is pain resulting from stimuli which are not normally painful, an exaggerated response to otherwise non-noxious stimuli and can be either static or dynamic allodynia, i.e. occurring spontaneously without movement or with movement. Allodynia may also be perceived in other areas than the one stimulated; hence it can also be dysesthetic. It is common to inflammatory conditions particularly joint inflammation.

"Somatic pain" is taken to mean pain originating in the cutaneous or deep tissues, when it occurs in the musculo-skeletal tissues, it is called "deep somatic pain". "Visceral pain" is taken to mean pain caused by activation of pain receptors resulting from infiltration, compression, extension, or stretching of the thoracic, abdominal, or pelvic viscera.

"Pain" as used herein refers to pain of any etiology, including acute and chronic pain, and any pain with an inflammatory component. Examples of pain include post-surgical pain, post-operative pain (including dental pain), migraine, headache and trigeminal neuralgia, pain associated with burn, wound or kidney stone, pain associated with trauma (including traumatic head injury), neuropathic pain, back pain such as chronic lower back pain, pain associated with musculo-skeletal disorders such as rheumatoid arthritis, pain associated with osteoarthritis, ankylosing spondylitis, sero-negative (non-rheumatoid) arthropathies, non-articular rheumatism and peri-articular disorders, and pain associated with cancer (including "break-through pain", and pain associated with terminal cancer and pain due to bone metastases), peripheral neuropathy and post-herpetic neuralgia, pain associated with interstitial cystitis and/or painful bladder syndrome and/or bladder pain syndrome, pain associated with chronic prostatitis and/or chronic pelvic pain syndrome, pain associated with endometriosis and/or uterine fibroids. Examples of pain with an inflammatory component (in addition to some of those described above) include rheumatic pain, pain associated with mucositis, and dysmenorrhea.

"Post-surgical pain" (interchangeably termed "post-incisional" or "post-traumatic pain") refers to pain arising or resulting from an external trauma such as a cut, puncture, incision, tear, or wound into tissue of an individual (including that that arises from all surgical procedures, whether invasive or non-invasive). As used herein, post-surgical pain does not include pain that occurs (arises or originates) without an external physical trauma. In some embodiments, post-surgical pain is internal or external (including peripheral) pain, and the wound, cut, trauma, tear or incision may occur accidentally (as with a traumatic wound) or deliberately (as with a surgical incision). As used herein, "pain" includes nociception and the sensation of pain, and pain can be assessed objectively and subjectively, using pain scores and other methods well-known in the art. Post-surgical pain, as used herein, includes allodynia (i.e., increased response to a normally non-noxious stimulus) and hyperalgesia (i.e., increased response to a normally noxious or unpleasant stimulus), which can in turn, be thermal or mechanical (tactile) in nature. In some embodiments, the pain is characterized by thermal sensitivity, mechanical sensitivity and/or resting pain. In some embodiments, the post-surgical pain comprises mechanically-induced pain or resting pain. In other embodiments, the post-surgical pain comprises resting pain.

The pain can be primary or secondary pain, as is well-known in the art.

Pain associated with interstitial cystitis and/or painful bladder syndrome and/or bladder pain syndrome may comprise lower abdominal (pelvic) pain; bladder pain; suprapubic pain; vaginal pain; pain in the penis, testicles, scrotum and perineum; urethral pain; dyspareneuria; pain, pressure or discomfort that may increase as the bladder fills.

Pain associated with chronic prostatitis and/or chronic pelvic pain syndrome may comprise lower abdominal (pelvic) pain; lower stomach pain; bladder pain; suprapubic pain; pain in the penis, testicles, scrotum and perineum; urethral pain; dyspareunia; pain, pressure or discomfort that may increase as the bladder fills; dysuria; and ejaculatory pain.

Lower urinary tract symptoms (LUTs) may comprise three groups of urinary symptoms, which may be defined as storage (irritative), voiding (obstructive) and post-micturition symptoms. Storage symptoms comprise urgency, frequency, nocturia, urgency incontinence and stress incontinence, which can be associated with overactive bladder (OAB) and benign prostatic hyperplasia (BPH). Voiding symptoms comprise hesitancy, poor flow, intermittency, straining and dysuria. Post-micturism symptoms comprise terminal dribbling, post-void dribbling and a sense of incomplete emptying.

Pain and/or other symptoms associated with endometriosis and/or uterine fibroids may comprise dysmenorrhoea; chronic non-menstrual, pelvic pain; dyspareunia; dyschexia; menorrhagia; lower abdominal or back pain; infertility and subfertility; dysuria; bloating and pain on micturition; nausea, vomiting and/or diarrohea. Symptoms may also comprise symptoms related to endometriotic lesions or fibroids located outside the peritoneal cavity including for example thoracic endometriosis syndrome manifest as haemoptysis, pneumothorax or haemothorax, and pulmonary leiomyosis manifest as dyspnoea and a pulmonary mass.

The following examples are provided to illustrate, but not to limit, the invention. The Examples in WO2004/058184 are referred to illustrate the antibodies for use in the present invention. The entire content of WO2004/058184 is hereby incorporated by reference.

EXAMPLES

Example 1 Antibody Production and Purification

For expression of full antibodies, heavy and light chain variable regions were cloned in two mammalian expression vectors (Eb.911.E3 or Eb.pur.911.3E for light chain and Db.911.3E for heavy chain; described herein) and transfected using lipofectemine into HEK 293 cells for transient expression. Antibodies were purified using protein A using standard methods.

The generation, production, purification and characterization of the anti-NGF antibody E3 is described in the Examples of WO2004/058184, the entire content of which is herein incorporated by reference. Vectors incorporating E3 light chain and E3 heavy chain have been deposited with the American Type Culture Collection, 10801 University Boulevard, Manassas, Va., USA (ATCC):

| Material | | ATCC Accession No. | Date of Deposit |
|---|---|---|---|
| Eb.911.3E | E3 light chain | PTA-4893 | Jan. 8, 2003 |
| Eb.pur.911.3E | E3 light chain | PTA-4894 | Jan. 8, 2003 |
| Db.911.3E | E3 heavy chain | PTA-4895 | Jan. 8, 2003 |

Details concerning these deposits can be found in WO2004058184, the content of which is herein incorporated by reference in its entirety.

Three mammalian expression vectors were designed and constructed for use in the expression of antibody E3 in mammalian cells.

Vector Db.911.3E is an expression vector comprising the heavy chain variable region of the E3 antibody and the human IgG2a constant region, and is suitable for transient or stable expression of the heavy chain. Db.911.3E consists of nucleotide sequences corresponding to the following regions: the murine cytomegalovirus promoter region (nucleotides 1-612); a synthetic intron (nucleotides 619-1507); the DHFR coding region (nucleotides 707-1267); human growth hormone signal peptide (nucleotides 1525-1602); antibody 3E heavy chain variable region (nucleotides 1603-1965); human heavy chain IgG2a constant region containing the following mutations: A330P331 to S330S331 (amino acid numbering with reference to the wildtype IgG2a sequence; see Eur. J. Immunol. (1999) 29:2613-2624); SV40 late polyadenylation signal (nucleotides 2974-3217); SV40 enhancer region (nucleotides 3218-3463); phage f1 region (nucleotides 3551-4006) and beta lactamase (AmpR) coding region (nucleotides 4443-5300). Db.911.3E was deposited at the ATCC on Jan. 8, 2003, and was assigned ATCC Accession No. PTA-4895.

Vector Eb.911.3E is an expression vector comprising the light chain variable region of the E3 antibody and the human kappa chain constant region, and is suitable for transient expression of the light chain. Eb.911.3E consists of nucleotide sequences corresponding to the following regions: the murine cytomegalovirus promoter region (nucleotides 1-612); human EF-1 intron (nucleotides 619-1142); human growth hormone signal peptide (nucleotides 1173-1150); antibody E3 light chain variable region (nucleotides 1251-1571); human kappa chain constant region (nucleotides 1572-1892); SV40 late polyadenylation signal (nucleotides 1910-2153); SV40 enhancer region (nucleotides 2154-2399); phage f1 region (nucleotides 2487-2942) and beta lactamase (AmpR) coding region (nucleotides 3379-4236). Eb.911.3E was deposited at the ATCC on Jan. 8, 2003, and was assigned ATCC Accession No. PTA-4893.

Vector Eb.pur.911.3E is an expression vector comprising the light chain variable region of the E3 antibody and the human kappa constant region, and is suitable for stable expression of the light chain. Eb.pur.911.3E consists of nucleotide sequences corresponding to the following regions: the murine cytomegalovirus promoter region (nucleotides 1-612); human EF-1 intron (nucleotides 619-1758); pac gene (puromycinR) coding region (nucleotides 739-1235); human hsp70 5'UTR region (nucleotides 1771-1973); human growth hormone signal peptide (nucleotides 1985-2062); antibody E3 light chain variable region (nucleotides 2063-2383); human kappa chain constant region (nucleotides 2384-2704); SV40 late polyadenylation signal (nucleotides 2722-2965); SV40 enhancer region (nucleotides 2966-3211); phage f1 region (nucleotides 3299-3654) and beta lactamase (AmpR) coding region (nucleotides 4191-5048). Eb.pur.911.E3 was deposited at the ATCC on Jan. 8, 2003, and was assigned ATCC Accession No. PTA-4894.

Transient cell expression was performed as follows: CHO and HEK293T cells in 150 mm dishes were transiently co-transfected with 25 ug of each plasmid (i.e., one plasmid containing the heavy chain and one plasmid containing the light chain). DNA was mixed with 100 ul lipofectamine 2000 (Invitrogen) according to the manufacturer's instructions. The DNA-lipid complexes were allowed to contact the cells in DMEM/F12 medium without serum or antibiotics for 5 hours. Following this incubation, the media was changed for expression to Opti-MEM (Invitrogen) without any additives for two days. Cell supernatants containing antibody were harvested sequentially up to four times with subsequent media replacement. Supernatants were purified by affinity chromatography using MapSelect Protein A resin (Amersham biosciences 17-5199-02). Antibody was bound to the protein A resin in 0.3M glycine, 0.6M NaCl buffer at pH 8, then eluted with 0.1M citrate buffer at pH 3. Fractions containing antibody were immediately neutralized with 1M Tris buffer at pH 8.0, Antibody fractions were then dialyzed and concentrated in PBS. Antibodies were selected, and assayed as follows:

Biacore Assay

Affinities of anti-NGF Fabs and monoclonal antibodies were determined using the BIAcore3000™ surface plasmon resonance (SPR) system (BIAcore, INC, Piscaway N.J.). CM5 chips were activated with N-ethyl-N'-(3-dimethylaminopropyl)-carbodiimide hydrochloride (EDC) and N-hydroxysuccinimide (NHS) according to the supplier's instructions. Human NGF was diluted into 10 mM sodium acetate pH 4.0 and injected over the activated chip at a concentration of 0.005 mg/mL. Using variable flow time across the individual chip channels, two ranges of antigen density were achieved: 100-200 response units (RU) for detailed kinetic studies and 500-600 RU for screening assays. The chip was blocked with ethanolamine. Regeneration studies showed that a mixture of Pierce elution buffer (Product No. 21004, Pierce Biotechnology, Rockford, Ill.) and 4 M NaCl (2:1) effectively removed the bound Fab while keeping the activity of hNGF on the chip for over 200 injections. HBS-EP buffer (0.01M HEPES, pH 7.4, 0.15 NaCl, 3 mM EDTA, 0.005% Surfactant P29) was used as running buffer for all the BIAcore assays.

Screening Assay

A screening BIAcore assay was optimized to determine the affinity of Fab clones from libraries. Supernatants of small culture lysates were injected at 50 μl/min for 2 min. Dissociation times of 10 to 15 minutes were used for determination of a single exponential dissociation rate ($k_{off}$) using BIAevaluation software. Samples that showed $k_{off}$ rates in the same range as the template used to create the library (clone 8L2-6D5, $k_{off}$ 1×10$^{-3}$ s$^{-1}$) were injected for confirmation and dissociation times of up to 45 min were allowed to obtain better $k_{off}$ values. Clones showing improved (slower) $k_{off}$ values were expressed at large scale and full kinetic parameters, $k_{on}$ and $k_{off}$, were determined on purified protein. The assay was capable of detecting differences in affinity that were approximately 2-fold or larger.

Affinity Determination Assay

Serial dilutions (0.1-10× estimated $K_D$) of purified Fab samples were injected for 1 min at 100 μL/min and dissociation times of up to 2 h were allowed. The concentrations of the Fab proteins were determined by ELISA and/or SDS-PAGE electrophoresis using as a standard a Fab of known concentration (as determined by amino acid analysis). Kinetic association rates ($k_{on}$) and dissociation rates ($k_{off}$) were obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values were calculated as $k_{off}/k_{on}$.

Example 2 Analysis of Buffers and pH

A study was conducted to evaluate the effect of four different buffers on antibody aggregation and fragmentation.

Specifically, four liquid formulations comprising anti-NGF antibody E3 and buffered with acetate, succinate, histidine or Citrate were prepared. The formulations then were stored at 5, 25 and 40° C. and antibody aggregation, fragmentation and oxidation measurements were taken at 0, 4, 9 and 13 weeks.

The manufacturing process can be summarized as follows: The buffer is prepared, pH adjusted, and sterile filtered (see Table 2.1 and 2.2 for details). The antibody is concentrated then buffer exchanged. The antibody is analyzed with UV and then diluted with respective buffer to 20 mg/mL. The 20 mg/mL solution is then sterile filtered. Finally, the sterile solution is filled, stoppered and capped with an overseal.

Aggregation Analysis:

The antibody formulations of Table 2.2 were stored at a temperature of 5, 25 and 40° C. for 0, 4, 9 and 13 weeks.

Each formulation was analyzed for aggregation using size exclusion chromatography (SEC). The size exclusion chromatography was carried out using a TSK gel G3000SWXL-G2000SWXL column, mobile phase 0.2 M sodium phosphate buffer at pH 7.0, a flow rate of 1 ml/min, and UV detection at 214 nm.

Aggregation levels were calculated by integrating the areas under the chromatogram peaks for each formulation and reporting the integrated areas under the high molecular weight species peaks as a percentage of total peak area. As can be seen in Table 2.3, the histidine-buffered formulations particularly at pH 6, showed the lowest levels of aggregation, followed by the acetate, succinate, then citrate buffered formulations, in that order.

Fragmentation Analysis:

The antibody formulations of Table 2.2 were stored at a temperature of 5, 25 and 40° C. for 0, 4, 9 and 13 weeks.

Each formulation also was analyzed for fragmentation using reduced capillary gel electrophoresis (rCGE). Proteins unfold (denature) and become 'rod-like' in structure following the cleavage of it's disulphide bonds in red-CGE. The 'reduced' protein separates into its heavy and light chains allowing for their quantization along with fragmented species. Reduced-CGE is considered a reliable method for quantifying percent fragments (% impurities). The percentage of fragmentation was measured at the relevant times for each of the formulations. The fragmentation levels were calculated as a percentage of total band volume. As can be seen in Table 2.4, the histidine-buffered formulations particularly at pH 6, showed the lowest levels of fragmentation.

Oxidation Analysis:

Oxidation levels of methionine residues at amino acid positions X and Y in anti-NGF antibody E3 were measured by a Lysine-C mapping method after storage for at 5, 25 and 40° C. for 0, 4, 9 and 13 weeks. Samples of each formulation tested were then digested with Lyc-C enzyme in tris buffer at pH 8.0 under standard conditions and analyzed by reversed-phase high performance liquid chromatography. Separation was accomplished using a Grace Vydae Protein C4 analytical column with 0.1% TFA in water and 0.085% TFA in Acetonitrile gradient elution. Percent oxidation of methionine amino acids in Anti-NGFantibody E3 was recorded.

The results in Table 2.5 indicate that the percent oxidation of the citrate formulation is greatest.

TABLE 2.1

Buffer Preparation Table: Summary of recorded amounts of buffer components from manufacturing records for compounding 250 mL of buffer.

| Formulation Lot Number | pH | Acetate (mg/mL) | Acetic Acid (mg/mL) | Histidine (mg/mL) | Histidine HCl (mg/mL) | Citrate (mg/mL) | Citric Acid (mg/mL) | Succinate (mg/mL) | Succinic Acid (mg/mL) |
|---|---|---|---|---|---|---|---|---|---|
| Acetate pH 5.0 | 5.0 | 435.58 | 104.14 | — | — | — | — | — | — |
| Acetate pH 5.5 | 5.5 | 577.75 | 34.59 | — | — | — | — | — | — |
| Acetate pH 6.0 | 6.0 | 644.28 | 15.07 | — | — | — | — | — | — |
| Acetate pH 6.5 | 6.5 | 668.51 | 10.32 | — | — | — | — | — | — |
| Histidine pH 5.0 | 5.0 | — | — | 70.45 | 839.27 | — | — | — | — |
| Histidine pH 5.5 | 5.5 | — | — | 186.9 | 751.9 | — | — | — | — |
| Histidine pH 6.0 | 6.0 | — | — | 387.5 | 454.1 | — | — | — | — |
| Histidine pH 6.5 | 6.5 | — | — | 588.75 | 220.87 | — | — | — | — |
| Citrate pH 5.0 | 5.0 | — | — | — | — | 233.63 | 107.18 | — | — |
| Citrate pH 5.5 | 5.5 | — | — | — | — | 279.09 | 79.01 | — | — |
| Citrate pH 6.0 | 6.0 | — | — | — | — | 321.25 | 42.51 | — | — |
| Citrate pH 6.5 | 6.5 | — | — | — | — | 348.77 | 20.52 | — | — |
| Succinate pH 5.0 | 5.0 | — | — | — | — | — | — | 585.18 | 176.86 |
| Succinate pH 5.5 | 5.5 | — | — | — | — | — | — | 679.4 | 80.83 |
| Succinate pH 6.0 | 6.0 | — | — | — | — | — | — | 756.23 | 34.73 |
| Succinate pH 6.5 | 6.5 | — | — | — | — | — | — | 791.83 | 11.60 |

TABLE 2.2

Formulation Matrix Table:

| Formulation Lot Number | pH | mAb Con (mg/mL) | Acetate (mg/mL) | Acetic Acid (mg/mL) | Histidine (mg/mL) | Histidine HCl (mg/mL) | Citrate (mg/mL) | Citric Acid (mg/mL) | Succinate (mg/mL) | Succinic Acid (mg/mL) |
|---|---|---|---|---|---|---|---|---|---|---|
| Acetate pH 5.0 | 5.0 | 20 | 1.7423 | 0.4323 | — | — | — | — | — | — |
| Acetate pH 5.5 | 5.5 | 20 | 2.3110 | 0.1813 | — | — | — | — | — | — |
| Acetate pH 6.0 | 6.0 | 20 | 2.5771 | 0.0639 | — | — | — | — | — | — |
| Acetate pH 6.5 | 6.5 | 20 | 2.6744 | 0.0210 | — | — | — | — | — | — |
| Histidine pH 5.0 | 5.0 | 20 | — | — | 0.2818 | 3.8182 | — | — | — | — |
| Histidine pH 5.5 | 5.5 | 20 | — | — | 0.7448 | 3.1909 | — | — | — | — |
| Histidine pH 6.0 | 6.0 | 20 | — | — | 1.5500 | 2.1000 | — | — | — | — |
| Histidine pH 6.5 | 6.5 | 20 | — | — | 2.3552 | 1.0091 | — | — | — | — |
| Citrate pH 5.0 | 5.0 | 5 | — | — | — | — | 0.9345 | 0.3821 | — | — |
| Citrate pH 5.5 | 5.5 | 5 | — | — | — | — | 1.1164 | 0.2530 | — | — |
| Citrate pH 6.0 | 6.0 | 5 | — | — | — | — | 1.2850 | 0.1325 | — | — |
| Citrate pH 6.5 | 6.5 | 5 | — | — | — | — | 1.3951 | 0.0538 | — | — |
| Succinate pH 5.0 | 5.0 | 20 | — | — | — | — | — | — | 2.3407 | 0.6561 |
| Succinate pH 5.5 | 5.5 | 20 | — | — | — | — | — | — | 2.7183 | 0.3809 |
| Succinate pH 6.0 | 6.0 | 20 | — | — | — | — | — | — | 3.0249 | 0.1575 |
| Succinate pH 6.5 | 6.5 | 20 | — | — | — | — | — | — | 3.1673 | 0.0537 |

TABLE 2.3

Summary of % Aggregation (via SEC) Data from 20 mg/mL anti-NGF antibody: pH and Buffer Screening Study

| | Condition | | | | | | | | |
|---|---|---|---|---|---|---|---|---|---|
| | 5° C. | | 25° C. | | | 40° C. | | | |
| | | | Weeks | | | | | | |
| Lot # | 0 | 13 | 0 | 9 | 13 | 0 | 4 | 9 | 13 |
| Acetate pH 5.0 | 1.6 | 1.8 | 1.6 | 2.2 | 2.5 | 1.6 | 3.2 | 5.1 | 8.1 |
| Acetate pH 5.5 | 1.8 | 2.1 | 1.8 | 2.7 | 3.0 | 1.8 | 3.4 | 4.9 | 7.1 |
| Acetate pH 6.0 | 2.0 | 2.4 | 2.0 | 3.2 | 3.3 | 2.0 | 4.3 | 5.5 | 7.0 |
| Acetate pH 6.5 | 2.0 | 2.5 | 2.0 | 3.5 | 3.9 | 2.0 | 4.4 | 5.8 | 7.0 |
| Histidine pH 5.0 | 1.6 | 1.8 | 1.6 | 2.0 | 2.3 | 1.6 | 2.7 | 3.9 | 7.0 |
| Histidine pH 5.5 | 1.6 | 1.8 | 1.6 | 2.2 | 2.4 | 1.6 | 2.7 | 3.4 | 5.1 |
| Histidine pH 6.0 | 1.8 | 2.1 | 1.8 | 2.5 | 2.7 | 1.8 | 3.0 | 3.5 | 4.8 |
| Histidine pH 6.5 | 1.9 | 2.2 | 1.9 | 2.8 | 3.1 | 1.9 | 3.4 | 4.2 | 5.6 |
| Citrate pH 5.0 | 1.6 | 1.9 | 1.6 | 2.4 | 2.8 | 1.6 | 4.6 | 8.5 | 15.0 |
| Citrate pH 5.5 | 1.8 | 2.2 | 1.8 | 3.0 | 3.3 | 1.8 | 4.9 | 8.7 | 12.2 |
| Citrate pH 6.0 | 2.0 | 2.5 | 2.0 | 3.3 | 3.7 | 2.0 | 4.4 | 6.5 | 8.4 |
| Citrate pH 6.5 | 2.1 | 2.8 | 2.1 | 3.7 | 4.2 | 2.1 | 4.8 | 6.5 | 8.4 |
| Succinate pH 5.0 | 1.6 | 1.9 | 1.6 | 2.3 | 2.7 | 1.6 | 3.5 | 6.1 | 11.2 |
| Succinate pH 5.5 | 2.0 | 2.2 | 2.0 | 2.8 | 3.2 | 2.0 | 3.9 | 5.7 | 8.4 |
| Succinate pH 6.0 | 1.8 | 2.5 | 1.8 | 3.1 | 3.6 | 1.8 | 4.3 | 5.8 | 7.8 |
| Succinate pH 6.5 | 2.2 | 2.8 | 2.2 | 3.7 | 4.1 | 2.2 | 4.8 | 5.9 | 7.5 |

TABLE 2.4

Summary of % Fragmentation (via reduced CGE) Data from 20 mg/mL anti-NGF antibody: pH and Buffer Screening Study

| | Condition | | | | | | | | |
|---|---|---|---|---|---|---|---|---|---|
| | 5 C. | | 25 C. | | | 40 C. | | | |
| | | | Weeks | | | | | | |
| Lot # | 0 | 13 | 0 | 9 | 13 | 0 | 4 | 9 | 13 |
| Acetate pH 5.0 | 1.1 | 1.1 | 1.1 | 1.4 | 1.0 | 1.1 | 4.2 | 7.0 | 10.3 |
| Acetate pH 5.5 | 1.1 | 1.0 | 1.1 | 1.0 | 1.7 | 1.1 | 4.4 | 5.2 | 9.4 |
| Acetate pH 6.0 | 1.1 | 1.1 | 1.1 | 1.3 | 1.1 | 3.6 | 5.9 | 7.2 | |
| Acetate pH 6.5 | 1.1 | 1.2 | 1.1 | 1.0 | 2.2 | 1.1 | 4.1 | 6.4 | 8.1 |
| Histidine pH 5.0 | 1.1 | 1.0 | 1.1 | 1.0 | 1.8 | 1.1 | 5.8 | 7.5 | 11.2 |
| Histidine pH 5.5 | 1.1 | 1.1 | 1.1 | 0.9 | 1.5 | 1.1 | 4.3 | 6.4 | 7.9 |
| Histidine pH 6.0 | 1.1 | 1.0 | 1.1 | 1.6 | 1.5 | 1.1 | 3.1 | 3.8 | 6.1 |
| Histidine pH 6.5 | 1.0 | 1.2 | 1.0 | 1.6 | 2.2 | 1.0 | 3.7 | 6.1 | 9.7 |
| Citrate pH 5.0 | 1.0 | 1.0 | 1.0 | 1.0 | 2.1 | 1.0 | 5.4 | 9.1 | 14.5 |
| Citrate pH 5.5 | 1.0 | 1.1 | 1.0 | 1.1 | 1.4 | 1.0 | 4.6 | 7.6 | 11.5 |
| Citrate pH 6.0 | 1.1 | 1.6 | 1.1 | 2.0 | 1.6 | 1.1 | 3.7 | 6.9 | 10.6 |
| Citrate pH 6.5 | 1.5 | 1.0 | 1.5 | 1.3 | 9.1 | 1.5 | 3.4 | 8.2 | 10.9 |
| Succinate pH 5.0 | 1.2 | 1.0 | 1.2 | 2.1 | 7.9 | 1.2 | 5.4 | 8.8 | 13.1 |
| Succinate pH 5.5 | 1.2 | 1.5 | 1.2 | 0.9 | 0.9 | 1.2 | 3.1 | 5.8 | 9.0 |
| Succinate pH 6.0 | 1.2 | 1.0 | 1.2 | 1.3 | 6.8 | 1.2 | 3 | 5.0 | 8.0 |
| Succinate pH 6.5 | 1.2 | 1.1 | 1.2 | 1.5 | 11.8 | 1.2 | 3.5 | 7.2 | 8.0 |

TABLE 2.5

Summary of % Oxidation Data from 20 mg/mL anti-NGF antibody: pH and Buffer Screening Study

| | Condition | | | | | | | | |
|---|---|---|---|---|---|---|---|---|---|
| | 5 C. | | 25 C. | | | 40 C. | | | |
| | | | Weeks | | | | | | |
| Lot # | 0 | 9 | 13 | 0 | 9 | 13 | 0 | 4 | 9 | 13 |
| Acetate pH 5.0 | 2.8 | 2.1 | | 2.8 | 2.3 | | 2.8 | | 3.3 | 4.1 |
| Acetate pH 5.5 | 2.8 | 2.1 | | 2.8 | 2.3 | | 2.8 | | 3.3 | 4.1 |
| Acetate pH 6.0 | 2.3 | 2.0 | | 2.3 | 2.2 | | 2.3 | | 3.1 | 3.4 |
| Acetate pH 6.5 | 2.3 | 2.1 | | 2.3 | 2.5 | | 2.3 | | 3.5 | 4.1 |
| Histidine pH 5.0 | 2.2 | 2.0 | | 2.2 | 2.5 | | 2.2 | | 4.1 | 6.4 |
| Histidine pH 5.5 | 2.6 | 1.8 | | 2.6 | 2.3 | | 2.6 | | 3.9 | 5.7 |
| Histidine pH 6.0 | 2.0 | 1.9 | | 2.0 | 2.3 | | 2.0 | | 3.9 | 6.1 |
| Histidine pH 6.5 | 2.4 | 2.1 | | 2.4 | 2.5 | | 2.4 | | 4.7 | 7.1 |
| Citrate pH 5.0 | 2.1 | 2.1 | | 2.1 | 2.8 | | 2.1 | | 7.2 | 9.7 |
| Citrate pH 5.5 | 2.8 | 2.1 | | 2.8 | 2.9 | | 2.8 | | 8.0 | 10.1 |
| Citrate pH 6.0 | 2.4 | 1.8 | | 2.4 | 2.7 | | 2.4 | | 6.6 | 7.9 |
| Citrate pH 6.5 | 2.4 | 1.8 | | 2.4 | 2.6 | | 2.4 | | 6.3 | 8.1 |
| Succinate pH 5.0 | 3.9 | 1.8 | | 3.9 | 2.2 | | 3.9 | | 4.0 | 5.5 |
| Succinate pH 5.5 | 2.7 | 1.9 | | 2.7 | 2.3 | | 2.7 | | 4.1 | 4.6 |
| Succinate pH 6.0 | 2.1 | 2.1 | | 2.1 | 2.1 | | 2.1 | | 3.8 | 3.4 |
| Succinate pH 6.5 | 2.7 | 2.1 | | 2.7 | 2.1 | | 2.7 | | 3.5 | 3.1 |

Example 3 Analysis of Tonicity Agents, Trehalose Vs Sucrose Vs Sorbitol

A study was conducted to compare the effect of tonicity agents in particular trehalose, sucrose and sorbitol on stability of anti-NGF antibody E3 formulations.

Specifically, three liquid formulations comprising anti-NGF antibody E3 and trehalose, sucrose or sorbitol were prepared as listed in Table 3.1. The formulations then were stored at 5, 25 and 40° C. and antibody aggregation, fragmentation and oxidation measurements were taken at 2, 4, 8, 13 and 26 weeks.

The manufacturing process for formulations in Table 3.1 can be summarized as follows: The buffer is prepared, pH adjusted, and sterile filtered (see Table 3.1 for details). Stock excipients solutions are prepared and sterile filtered. The antibody is concentrated then buffer exchanged. The concentrated antibody is analyzed with UV and then diluted with respective buffer to 50 mg/mL and respective excipients combined to the required concentration. The 50 mg/mL solution is then sterile filtered. Finally, the sterile solution is filled, stoppered and overseated. All formulations have a pH of 6.0 and an anti-NGF antibody E3 concentration of 50 mg/ml.

Aggregation Analysis:

The antibody formulations of Table 3.1 were stored at a temperature of 5, 25 and 40° C. for 2, 4, 8, 13 and 26 weeks.

Each formulation was analyzed for aggregation using the method described in Example 2. Aggregation levels were calculated and are shown in FIG. 1.

Fragmentation Analysis:

The antibody formulations of Table 3.1 were stored at a temperature of 5, 25 and 40° C. for 2, 4, 8, 13 and 26 weeks.

Figure 2:
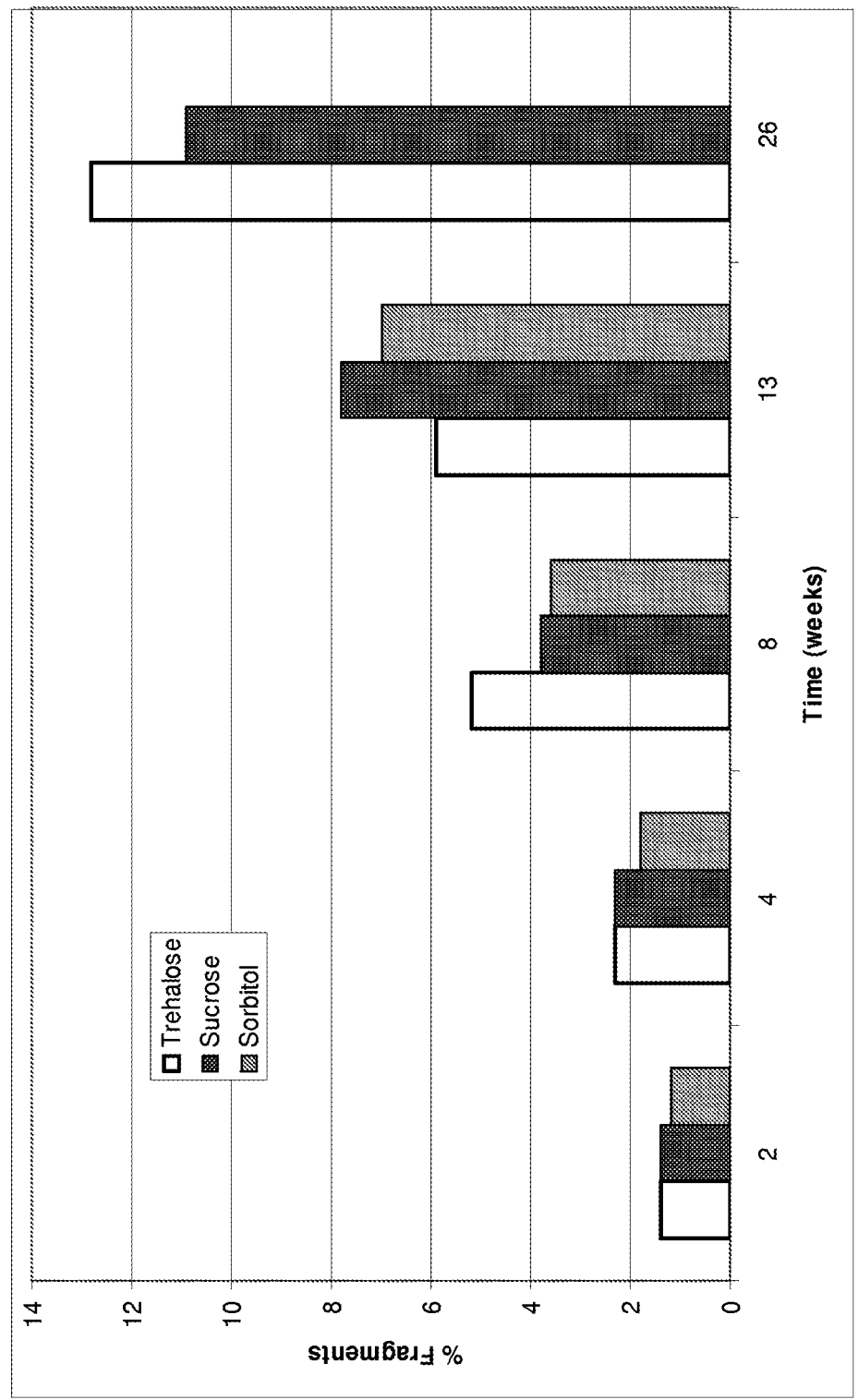
FIG. 2. Summary of % Fragments (via reduced CGE) Data from 50 mg/mL anti-NGF antibody: Tonicity Agent Screening Study at 40° C.

Each formulation also was analyzed for fragmentation using the methodology of Example 2. As can be seen in FIG. 2, the trehalose formulation, showed the lowest levels of fragmentation at 13 weeks storage.

TABLE 3.1

Formulation Matrix

| Formulation Lot Number | pH | mAbConc (mg/mL) | Histidine (mM) | Trehalose (mg/mL) | Sucrose (mg/mL) | Sorbitol (mg/mL) |
|---|---|---|---|---|---|---|
| 114069-001-A# | 6.0 | 50 | 10 | 84 | — | — |
| 114069-001-B# | 6.0 | 50 | 10 | — | 80 | — |
| 114069-001-C# | 6.0 | 50 | 10 | — | — | 40 |

Example 4 Tonicity Agent Screening Study: Trehalose vs. Sucrose

A study was conducted to compare the effect of tonicity agents in particular trehalose and sucrose on stability and activity of anti-NGF antibody E3 formulations. The hydrolysis of sucrose to fructose and glucose in a dilute acid solution is well known. Glucose molecules are also known to bind at random with the lysine residues of a protein's amino acid sequence. This is known as glycation. Therefore a protein formulation, buffered to an acidic pH, containing sucrose, could experience sucrose hydrolysis and then glycation. The glycated protein could undergo degradation processes more readily than an unglycated protein. Hence, the presence of sucrose in a liquid protein formulation could have an adverse impact on the protein's quality over its shelf-life. In contrast to this, trehalose is not known to undergo such a hydrolysis-based degradation and can be a preferential tonicity modifying agent in protein formulations.

Specifically, six liquid formulations comprising anti-NGF antibody E3 with sucrose and two liquid formulations comprising anti-NGF antibody E3 and trehalose were prepared, see Table 4.1. The formulations then were stored at 5, 25 and 40° C. and antibody aggregation, and glycation measurements were taken at 2, 4, 8, 13 and 26 weeks.

The manufacturing process for formulations in Table 4.1 can be summarized as follows: The buffer is prepared, pH adjusted, and sterile filtered (see Table 4.1 for details). Stock excipients solutions are prepared and sterile filtered. The antibody is concentrated then buffer exchanged. The concentrated antibody is analyzed with UV and then diluted with respective buffer to 10 mg/ml or 50 mg/ml and respective excipients combined to the required concentration. The 10 mg/ml or 50 mg/ml solution is then sterile filtered. Finally, the sterile solution is filled, stoppered and oversealed.

Aggregation Analysis:

The antibody formulations of Table 4.1 were stored at a temperature of 5, 25, 40 and 50° C. for 2, 4, 8, 13 and 26 weeks.

Each formulation was analyzed for aggregation using size exclusion chromatography (SEC) as described in Example 2. Calculated aggregation levels are compared in Table 4.2 and show that the trehalose demonstrates as low if not lower levels of aggregation compared to sucrose for the same antibody concentrations investigated.

Glycation Analysis:

Glycation levels of lysine residues in anti-NGF antibody E3 were measured by a mass spectrometry mapping method after storage of the formulations at 25, 40 and 50° C. for 0, 2, 4, 8 and 13 weeks for formulation samples comprising either sucrose or trehalose tonicity agent according to Table 4.1 (10 mg/ml antibody, 10 mM Histidine pH6.0). Glycation was found to be proportional to the rate of hydrolysis of the tonicity agent. There was no demonstrated hydrolysis of trehalose, hence trehalose is a preferred tonicity agent over sucrose for the antibody formulation as glycation of the formulation antibody is avoided, sucrose demonstrated between 1% and 2% hydrolysis in formulations stored at 25° C. for 104 weeks.

TABLE 4.3

Summary of Glycation of the anti-NGF antibody (reported as % heavy chain + 162 Daltons) Data from 10 mg/mL anti-NGF antibody: Comaprison of sucrose vs. trehalose

| | Condition | | | | | | | | |
|---|---|---|---|---|---|---|---|---|---|
| | 25° C. | | | 40° C. | | | 50° C. | | |
| | | | | weeks | | | | | |
| Lot# | 0 | 4 | 12 | 0 | 4 | 12 | 0 | 4 | 9 | 12 |
| 112633-174 | 0 | — | — | 0 | — | 4 | 0 | 3 | 19 | 23 |
| 112633-175 | 0 | — | — | 0 | — | 4 | 0 | 4 | 22 | 29 |
| 112633-176 | 0 | — | — | 0 | — | 3 | 0 | 4 | 13 | 17 |
| 112633-177 | 0 | — | — | 0 | — | 3 | 0 | 4 | 14 | 18 |
| 112633-178 | 0 | — | — | 0 | — | 4 | 0 | 7 | 29 | 49 |
| 112633-179 | 0 | — | — | 0 | — | 4 | 0 | 7 | 30 | 52 |
| 112633-180 | 0 | — | — | 0 | — | — | 0 | — | — | — |
| 112633-181 | 0 | — | — | 0 | — | — | 0 | 1 | — | — |
| 112633-182 | 19 | 67 | — | 19 | 92 | 60 | 19 | | | 100 |

Example 5 Analysis of Surfactant Agents and Polymer Stabilizers

A study was conducted to compare the effect of surfactants and polymer stabilizers, in particular PS20, PS80, PEG3350, PEG3350+PS20 on stability of anti-NGF antibody E3 formulations.

Specifically, four liquid formulations comprising anti-NGF antibody E3 and PS20, PS80, PEG3350, PEG3350+

TABLE 4.1

Formulation Matrix Table for Example 4

| Formulation Lot Number | pH | mAbConc (mg/mL) | Histidine (mg/mL) | Histidine HCl (mg/mL) | Sucrose (mg/mL) | Trehalose (mg/mL) | Glucose (mg/mL) | Fructrose (mg/mL) | Methionine (mg/mL) | EDTA (mg/mL) | PS20 (mg/mL) |
|---|---|---|---|---|---|---|---|---|---|---|---|
| 112633-174 | 6.0 | 10 | 0.8206 | 0.9879 | 94 | — | — | — | — | — | 0.1 |
| 112633-175 | 6.0 | 10 | 0.8206 | 0.9879 | 94 | — | — | — | — | 0.05 | 0.1 |
| 112633-176 | 6.0 | 10 | 0.8206 | 0.9879 | 94 | — | — | — | 0.1 | 0.05 | 0.1 |
| 112633-177 | 6.0 | 10 | 0.8206 | 0.9879 | 94 | — | — | — | 0.1 | — | 0.1 |
| 112633-178 | 5.7 | 10 | 0.5586 | 1.3418 | 94 | — | — | — | — | — | 0.1 |
| 112633-179 | 5.7 | 10 | 0.5586 | 1.3418 | 94 | — | — | — | — | 0.05 | 0.1 |
| 112633-180 | 6.0 | 10 | 0.8206 | 0.9879 | — | 84 | — | — | — | 0.05 | 0.1 |
| 112633-181 | 5.7 | 10 | 0.5586 | 1.3418 | — | 84 | — | — | — | 0.05 | 0.1 |
| 112633-182 | 6.0 | 10 | 0.8206 | 1.3418 | — | — | 49.5 | 49.5 | — | 0.05 | 0.1 |

TABLE 4.2

Summary of % Aggregation (via SEC) Data from 10 mg/mL anti-NGF antibody: Comparison of sucrose vs. trehalose

| | Condition | | | | | | | | |
|---|---|---|---|---|---|---|---|---|---|
| | 25° C. | | | 40° C. | | | 50° C. | | |
| | | | | weeks | | | | | |
| Lot# | 0 | 4 | 12 | 0 | 4 | 12 | 0 | 4 | 12 |
| 112633-174 | 0.5 | 0.5 | 0.8 | 0.5 | 1.0 | 1.9 | 0.5 | 4.3 | 20.4 |
| 112633-175 | 0.5 | 0.6 | 0.6 | 0.5 | 0.7 | 1.4 | 0.5 | 3.2 | 19.2 |
| 112633-176 | 0.5 | 0.6 | 0.7 | 0.5 | 0.7 | 1.2 | 0.5 | 2.9 | 13.5 |
| 112633-177 | 0.5 | 0.6 | 0.6 | 0.5 | 0.8 | 1.2 | 0.5 | 2.8 | 13.2 |
| 112633-178 | 0.5 | 0.5 | 0.6 | 0.5 | 1.0 | 1.8 | 0.5 | 4.6 | 24.8 |
| 112633-179 | 0.5 | 0.5 | 0.6 | 0.5 | 0.7 | 1.4 | 0.5 | 3.6 | 20.0 |
| 112633-180 | 0.5 | 0.6 | 0.7 | 0.5 | 0.8 | 1.6 | 0.5 | 3.1 | 11.4 |
| 112633-181 | 0.5 | 0.5 | 0.6 | 0.5 | 0.7 | 1.7 | 0.5 | 3.7 | 12.5 |
| 112633-182 | 0.5 | 0.6 | 0.9 | 0.5 | 1.7 | 12.1 | 0.5 | | |

PS20 were prepared as listed in Table 5.1. The formulations then were stored at 5, 25 and 40° C. and antibody aggregation, fragmentation and oxidation measurements were taken at 2, 4, 8, 13 and 26 weeks.

All formulations had a pH of 6.0 and an anti-NGF antibody E3 concentration of 50 mg/m I. The manufacturing process for formulations in Table 5.1 can be summarized as follows: The buffer is prepared, pH adjusted, and sterile filtered (see Table 5.1 for details). Stock excipients solutions are prepared and sterile filtered. The antibody is concentrated then buffer exchanged. The concentrated antibody is analyzed with UV and then diluted with respective buffer to 50 mg/ml and respective excipients combined to the required concentration. The 50 mg/ml solution is then sterile filtered. Finally, the sterile solution is filled, stoppered and oversealed. Tables 5.2 and 5.3 report the results.

Aggregation Analysis:

The antibody formulations of Table 5.1 were stored at a temperature of 5, 25 and 40° C. for 2, 4, 8, 13 and 26 weeks.

Each formulation was analyzed for aggregation using size exclusion chromatography (SEC) as described in Example 2. Calculated aggregation levels are compared in Table 5.2 and show that the PS20 at a concentration of 0.2 mg/ml demonstrates equivalent levels of aggregation compared to PS80 of 0.2 mg/ml and PEG3350 1 mg/ml investigated. PS20 at a concentration of 0.1 mg/ml also demonstrates equivalent results (data from 40° C.).

Fragmentation Analysis:

The antibody formulations of Table 5.1 were stored at a temperature of 5, 25 and 40° C. for 2, 4, 8, 13 and 26 weeks.

Each formulation was analyzed for fragmentation using the methodology of Example 2. Data collected from the 40° C. samples is shown in Table 5.3, and show that the PS20 at a concentration of 0.2 mg/ml demonstrates equivalent levels of fragmentation compared to PS80 of 0.2 mg/ml and PEG3350 1 mg/ml investigated. PS20 at a concentration of 0.1 mg/ml was also shown to demonstrate equivalent results.

TABLE 5.1

Formulation Matrix for Surfactant Agent Screening Study

| Formulation Lot Number | pH | mABConc (mg/mL) | Histidine (mM) | PS20 (mg/mL) | PS80 (mg/mL) | PEG 3350 (mg/mL) | PS20 + PEG 3350 |
|---|---|---|---|---|---|---|---|
| 114069-001-D# | 6.0 | 50 | 10 | 0.2 | — | — | — |
| 114069-001-E# | 6.0 | 50 | 10 | — | 0.2 | — | — |
| 114069-001-F# | 6.0 | 50 | 10 | — | — | 10 | — |
| 114069-001-G# | 6.0 | 50 | 10 | — | — | — | 0.2 + 1 |

TABLE 5.2

Summary of % Aggregation (via SEC) Data from 50 mg/mL anti-NGF antibody: Surfactant Agent Screening Study

| | | | 25 C. Weeks | | | | 40 C. Weeks | | | |
|---|---|---|---|---|---|---|---|---|---|---|
| | | T0 | 4 | 8 | 13 | 26 | 2 | 4 | 8 | 13 | 26 |
| 114069-001-D2 | PS20 | 1 | 1.4 | 1.5 | 1.8 | 2.4 | 1.8 | 2.2 | 2.8 | 4.2 | 8.2 |
| 114069-001-E2 | PS80 | 0.9 | 1.3 | 1.5 | 1.8 | n/a | 1.8 | 2.2 | 3.1 | 4.2 | n/a |
| 114069-001-F2 | PEG3350 | 1 | 1.4 | 1.5 | 1.9 | n/a | 1.8 | 2.2 | 2.8 | 3.9 | n/a |
| 114069-001-G2 | PS20 + PEG3350 | 0.9 | 1.3 | 1.5 | 1.9 | n/a | 1.8 | 2.1 | 3 | 4.3 | n/a |

TABLE 5.3

Summary of % Fragments (via reduced CGE) Data from 50 mg/mL anti-NGF antibody: Surfactant Screening Study

| | | | 25 C. Weeks | | | | 40 C. Weeks | | | |
|---|---|---|---|---|---|---|---|---|---|---|
| | | T0 | 4 | 8 | 13 | 26 | 2 | 4 | 8 | 13 | 26 |
| 114069-001-D2 | PS20 | 0.9 | 0.8 | 1.3 | 2.3 | 3.1 | 1.3 | 2.6 | 5.5 | 7.1 | 13.6 |
| 114069-001-E2 | PS80 | 0.9 | 0.7 | 0.9 | 1.7 | n/a | 1.4 | 1.7 | 6.4 | 6.5 | n/a |
| 114069-001-F2 | PEG3350 | 0.9 | 0.8 | 1.6 | 2.3 | n/a | 1.6 | 1.8 | 4.5 | 7 | n/a |
| 114069-001-G2 | PS20 + PEG3350 | 0.8 | 0.7 | 1 | 2.3 | n/a | 1.3 | 1.2 | 4.9 | 7.9 | n/a |

Example 6 Analysis of Anti-Oxidant Agents

A study was conducted to compare the effect of antioxidant agents in particular methionine on stability of anti-NGF antibody E3 formulations.

Specifically, nine liquid formulations comprising anti-NGF antibody E3 with and without methionine were prepared. All formulations had a pH of 6.0 and an anti-NGF antibody E3 concentration of 10 or 50 mg/ml, 84 mg/ml trehalose or sucrose and 0.1 mg/ml PS20, 10 mM histidine, plus or minus 0.05 mg/ml EDTA.

The manufacturing process for formulations can be summarized as follows: The buffer is prepared, pH adjusted, and sterile filtered. Stock excipients solutions are prepared and sterile filtered. The antibody is concentrated then buffer exchanged. The concentrated antibody is analyzed with UV and then diluted with respective buffer to 10 or 50 mg/ml and respective excipients combined to the required concentration. The 10 mg/ml or 50 mg/ml solution is then sterile filtered. Finally, the sterile solution is filled, stoppered and oversealed.

The formulations then were stored at 5, 25 and 40° C. and antibody aggregation, fragmentation and oxidation measurements were taken at 2, 4, 8, 13, 26 and 52 weeks.

Aggregation Analysis:

The antibody formulations of were stored at a temperature of 5, 25 and 40° C. for 0, 8, 13, 26 and 52 weeks.

Each formulation was analyzed for aggregation using size exclusion chromatography (SEC) as described in Example 2. Calculated aggregation levels were compared and found not to be significantly different for samples stored at 5 or 25° C. for 26 weeks with or without methionine, the presence of methionine has no discernable effect on aggregation.

Fragmentation Analysis:

The antibody formulations were stored at a temperature of 5, 25 and 40° C. for 0, 8, 13 and 26 weeks, fragmentation measures were taken at 26 weeks.

Each formulation was analyzed for fragmentation using the methodology of Example 2. Calculated fragmentation levels were compared and found not to be significantly different for samples stored at 5 or 25° C. for 26 weeks with or without methionine, the presence of methionine has no discernable effect on fragmentation.

Oxidation Analysis:

Oxidation levels of methionine residues at amino acid positions X and Y in anti-NGF antibody E3 were measured by a Lysine-C mapping method after storage for at 5, 25 and 40° C. for 0, 13, 26 and 52 weeks. Percent oxidation of methionine amino acids in Anti-NGF antibody E3 was recorded as described in Example 2.

The results in Table 6.1 indicate that the percent oxidation of the antibody is reduced by the presence of methionine under longer periods of storage.

TABLE 6.1

Summary of % Oxidation Data from 10 and 50 mg/mL anti-NGF antibody: Antioxidant Agent Screening Study

|  | 0 | 25° C. Weeks | | | 40° C. | | |
|---|---|---|---|---|---|---|---|
|  | 0 | 13 | 26 | 52 | 13 | 26 | 52 |
| 10 mM Histidine + Suc + PS20 + 10 mg/mL mAb |  | 3.50 | 3.40 | 4.70 | 7.80 | 21.00 | 51.60 |
| 10 mM Histidine + Suc + PS20 + EDTA + Met + 10 mg/mL mAb |  | 4.70 | 3.20 | 0.00 | 7.00 | 10.90 | 0.00 |
| 10 mM Histidine + Suc + PS20 + 50 mg/mL mAb | 1.77 | 3.90 | 3.80 | 5.50 | 8.40 | 15.50 | 39.20 |
| 10 mM Histidine + Suc + PS20 + EDTA + Met + 50 mg/mL mAb | 1.72 | 2.70 | 3.40 | 3.10 | 5.10 | 10.10 | 30.60 |
| 10 mM Histidine + Tre + PS20 + 50 mg/mL mAb | 1.79 | 3.40 | 3.80 | 5.80 | 6.80 | 15.00 | 30.00 |
| 10 mM Histidine + Tre + PS20 + EDTA + 50 mg/mL mAb | 1.65 | 3.30 | 4.00 | 5.90 | 6.60 | 11.20 | 20.20 |
| 10 mM Histidine + Tre + PS20 + Met + 50 mg/mL mAb | 1.72 | 2.70 | 2.80 | 2.60 | 3.90 | 6.50 | 14.40 |
| 10 mM Histidine + Tre + PS20 + EDTA + Met + 50 mg/mL mAb | 1.70 | 2.70 | 3.30 | 3.10 | 4.60 | 7.00 | 14.00 |
| 10 mM Histidine + Tre + PS20 + EDTA + Met + 10 mg/mL mAb | 0.00 | 4.10 | 3.30 | 3.30 | 6.20 | 6.80 | 12.60 |

Example 7 Freeze Thaw Stability Study with and without Trehalose

Antibody formulations were prepared comprising 50 mg/ml anti-NGF antibody E3, mM histidine buffer pH 6.0, and 84 mg/ml trehalose, identical samples were prepared lacking trehalose. The samples were subjected to up to 4 cycles of freezing and thawing and aggregation was determined for the samples. Freeze thaw cycles are 72 hrs freezing at −70° C. and 48 hrs thawing at 5° C.

Each formulation was analyzed for aggregation using size exclusion chromatography (SEC) as described in Example 2. Calculated aggregation levels are compared in Table 7.1 and show that the samples comprising trehalose offer complete protection from freeze thaw effects on aggregation of the antibody. Samples with trehalose show no appreciable increase in level of aggregation over time.

TABLE 7.1

Summary of % Aggregation (via SEC) Data from 50 mg/mL anti-NGF antibody:

| Freeze/Thaw Cycle | % HMMS of Control Sample (no Trehalose) | % HMMS of Trehalose Sample |
|---|---|---|
| 0 | 0.60 | 0.60 |
| 1 | 0.75 | 0.60 |
| 2 | 0.90 | 0.60 |
| 3 | 1.00 | 0.60 |
| 4 | 1.30 | 0.60 |

Example 8 Multiple Freeze Thaw Stability of Anti-NGF Antibody E3 Formulation with Trehalose Antibody formulations (112746-124 and 112746-125) were prepared comprising 22 mg/ml anti-NGF antibody E3, 10 mM histidine buffer pH 6.0, and 84 mg/ml trehalose, 0.05 mg/mL disodium EDTA and 0.1 mg/mL polysorbate 20. The samples were subjected to up to 15 cycles of freezing and thawing and aggregation was determined for the samples.

Figure 3:
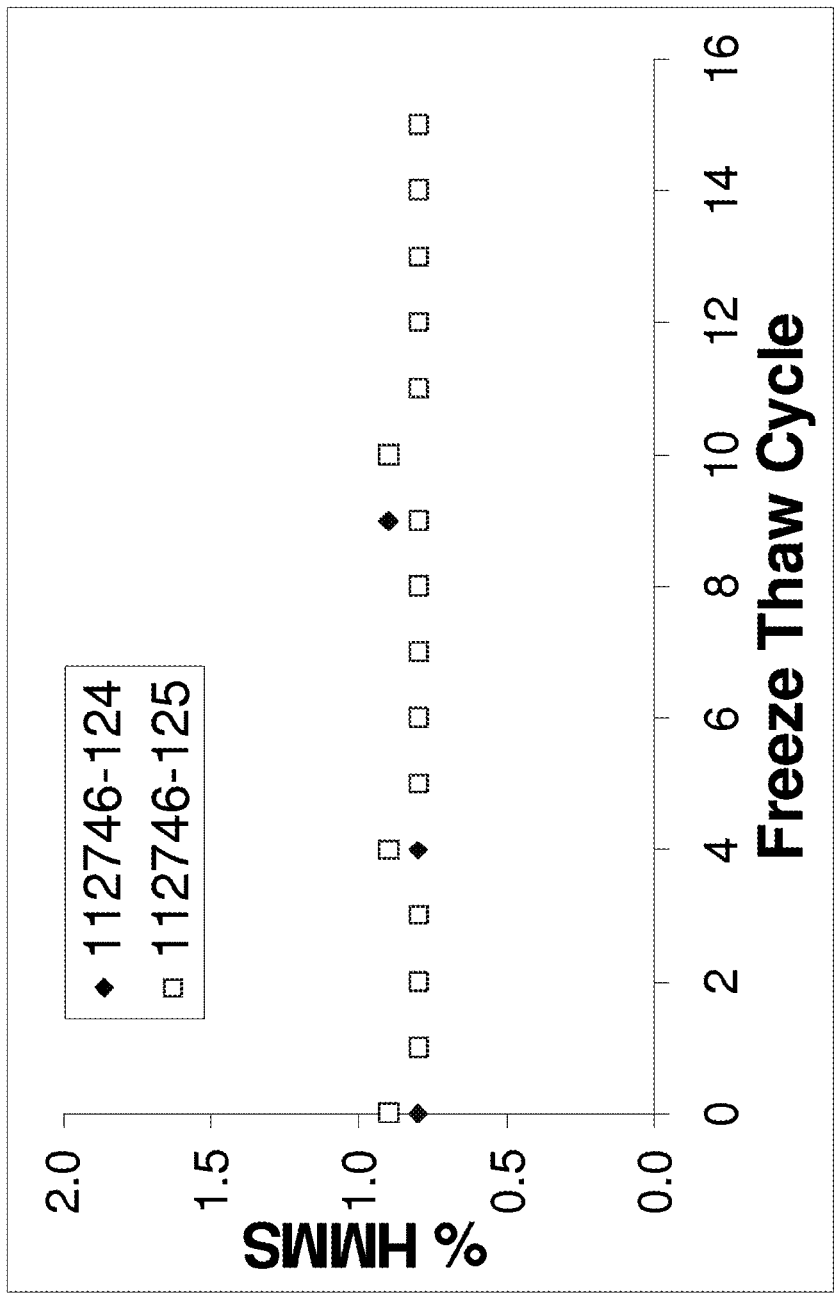
FIG. 3 Summary of % Aggregation (via SEC) Data from 22 mg/mL anti-NGF antibody subjected to 15 Freeze-Thaw Cycles.

Each formulation was analyzed for aggregation using size exclusion chromatography (SEC) as described in Example 2. Calculated aggregation levels are compared in FIG. 3 and show that all the samples comprising trehalose offer complete protection from freeze thaw effects on aggregation of the antibody. Samples with trehalose show no appreciable increase in level of aggregation over time.

Example 9 Long-Term Stability Study at 10 and 50 mg/ml Anti-NGF Antibody E3: Effect of Trehalose as a Stabilizer Antibody formulations were prepared comprising 10 mg/ml anti-NGF antibody E3, 10 mM histidine buffer pH 6.0, and 84 mg/ml trehalose, identical samples were prepared lacking trehalose. Details of the samples studied are given in Table 9.1. The samples were stored at a temperature of 5, 25 and 40° C. for 2, 4, 8, 13, 26 and 52 weeks and aggregation was determined for the samples. Each formulation was analyzed for aggregation using size exclusion chromatography (SEC) as described in Example 2. Data collected showed that the samples comprising trehalose offers high levels of protection from the effects on aggregation of the antibody on storage at accelerated condition of 40° C.

TABLE 9.1

Formulation Matrix for Long-Term Stability Study at 10 and 50 mg/mL anti-NGF antibody E3: Effect of Trehalose as a stabilizer

| Formulation Lot Number | pH | PF-04383119 (mg/mL) | Histidine mM | Sucrose (mg/mL) | Trehalose (mg/mL) | PS20 (mg/mL) | Methionine (mg/mL) | EDTA (mg/mL) |
|---|---|---|---|---|---|---|---|---|
| 112746-27-1 | 6.0 | 10 | 10 | 94 | — | 0.1 | — | — |
| 112746-27-2 | 6.0 | 10 | 10 | 94 | — | 0.1 | 0.1 | 0.05 |
| 112746-27-3 | 6.0 | 50 | 10 | 94 | — | 0.1 | — | — |

TABLE 9.1-continued

Formulation Matrix for Long-Term Stability Study at 10 and 50 mg/mL anti-NGF antibody E3: Effect of Trehalose as a stabilizer

| Formulation Lot Number | pH | PF-04383119 (mg/mL) | Histidine mM | Sucrose (mg/mL) | Trehalose (mg/mL) | PS20 (mg/mL) | Methionine (mg/mL) | EDTA (mg/mL) |
|---|---|---|---|---|---|---|---|---|
| 112746-27-4 | 6.0 | 50 | 10 | 94 | — | 0.1 | 0.1 | 0.05 |
| 112746-27-5 | 6.0 | 50 | 10 | — | 84 | 0.1 | — | — |
| 112746-27-6 | 6.0 | 50 | 10 | — | 84 | 0.1 | — | 0.05 |
| 112746-27-7 | 6.0 | 50 | 10 | — | 84 | 0.1 | 0.1 | — |
| 112746-27-8 | 6.0 | 50 | 10 | — | 84 | 0.1 | 0.1 | 0.05 |
| 112746-27-9 | 6.0 | 10 | 10 | — | 84 | 0.1 | 0.1 | 0.05 |

TABLE 9.2

% Aggregation Data (per SEC) at 40° C. for Long-Term Stability Study at 10 and 50 mg/mL anti-NGF antibody E3: Effect of Trehalose as a stabilizer

| Composition | Sample ID | Time (weeks) | | | | | | |
|---|---|---|---|---|---|---|---|---|
| | | 0 | 2 | 4 | 8 | 13 | 26 | 52 |
| 10 mM Histidine + Suc + PS20 + 10 mg/mL mAB | 112746-27-1 | 0.60 | 0.70 | 0.90 | 1.2 | 1.7 | 4.80 | 22.10 |
| 10 mM Histidine + Suc + PS20 + EDTA + Met + 10 mg/mL mAB | 112746-27-2 | 0.60 | 0.70 | 0.90 | 1.2 | 1.5 | 3.40 | NA |
| 10 mM Histidine + Suc + PS20 + 50 mg/mL mAB | 112746-27-3 | 0.60 | 1.60 | 2.00 | 2.8 | 3.7 | 7.50 | 20.70 |
| 10 mM Histidine + Suc + PS20 + EDTA + Met + 50 mg/mL mAB | 112746-27-4 | 0.60 | 1.50 | 1.80 | 2.4 | 3.2 | 6.00 | 22.40 |
| 10 mM Histidine + Tre + PS20 + 50 mg/mL mAB | 112746-27-5 | 0.60 | 1.70 | 1.90 | 2.9 | 3.8 | 7.60 | 16.20 |
| 10 mM Histidine + Tre + PS20 + EDTA + 50 mg/mL mAB | 112746-27-6 | 0.60 | 1.70 | 2.00 | 2.6 | 3.3 | 5.40 | 13.20 |
| 10 mM Histidine + Tre + PS20 + Met + 50 mg/mL mAB | 112746-27-7 | 0.60 | 1.60 | 1.80 | 2.5 | 3.2 | 5.40 | 12.60 |
| 10 mM Histidine + Tre + PS20 + EDTA + Met + 50 mg/mL mAB | 112746-27-8 | 0.60 | 1.60 | 1.80 | 2.5 | 3.1 | 4.80 | 11.60 |
| 10 mM Histidine + Tre + PS20 + EDTA + Met + 10 mg/mL mAB | 112746-27-9 | 0.60 | 0.90 | 1.00 | 1.4 | 1.8 | 3.10 | 7.00 |

Example 10 Long-Term Stability Study of Anti-NGF Antibody E3 Formulation Containing Trehalose, EDTA, Polysorbate 20 in Histidine Buffer at pH 6.0 at 2.5, 5, 10, 20 and 50 mg/mL Antibody formulations were prepared comprising 2.5, or 5 or 10 or 20 or 50 mg/mL anti-NGF antibody E3, 10 mM histidine buffer pH 6.0, and 84 mg/ml trehalose, 0.05 mg/mL EDTA and 0.1 mg/mL polysorbate 20. The samples were stored at a temperature of between 5 and 8° C. for up to 24 months and beyond and aggregation, fragmentation, oxidation was determined for the samples.

Figure 4:
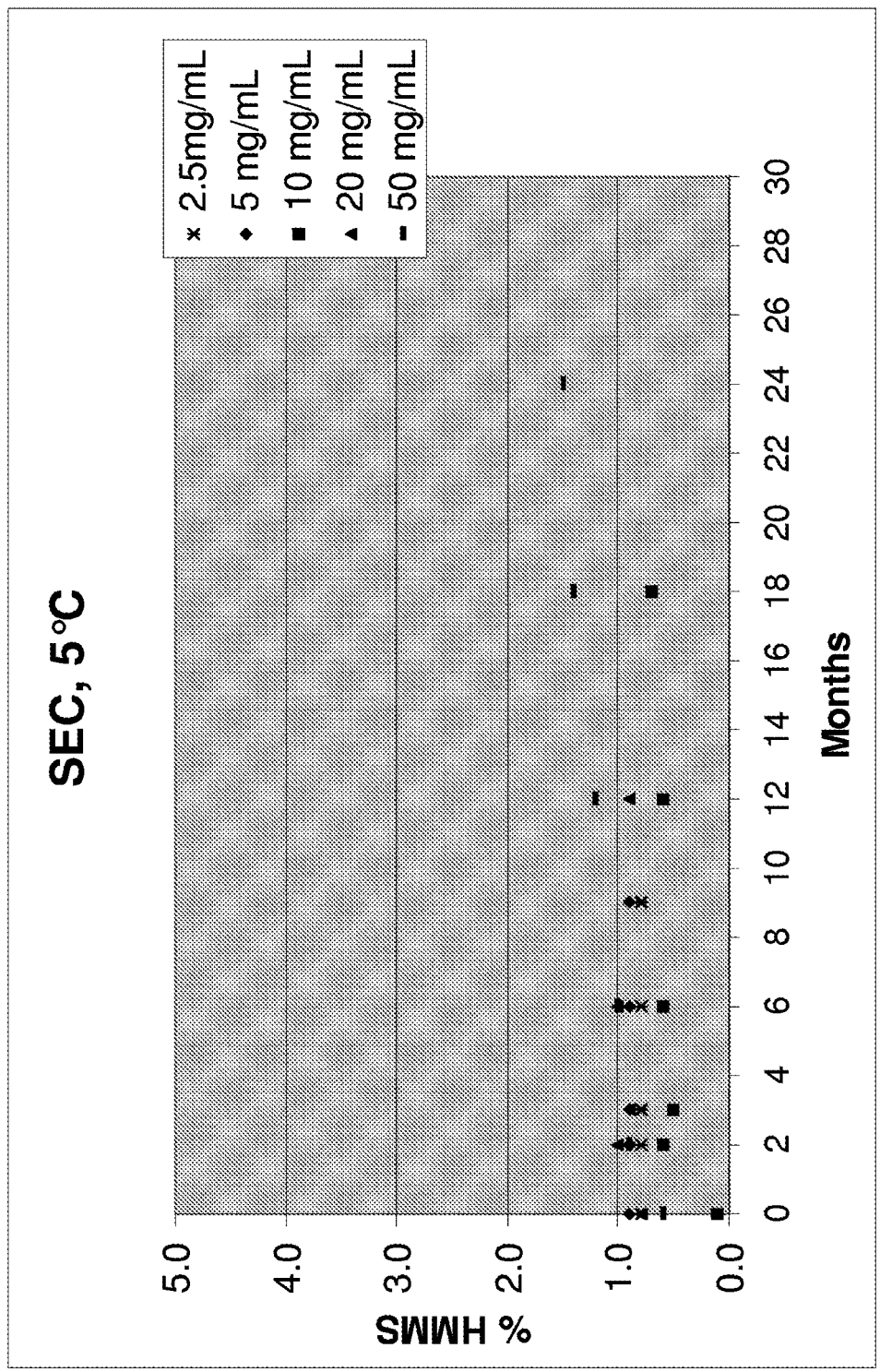
FIG. 4 % Aggregation Data (per SEC) at 5° C. for Long-Term Stability Study of anti-NGF antibody E3 formulation containing trehalose, EDTA, polysorbate 20 in histidine buffer at pH 6.0 at 2.5, 5, 10, 20 and 50 mg/mL FIG. 5 % Fragmentation Data (per reduced CGE) at 5° C. for Long-Term Stability Study of anti-NGF antibody E3 formulation containing trehalose, EDTA, polysorbate 20 in histidine buffer at pH 6.0 at 2.5, 5, 10, 20 and 50 mg/mL FIG. 6 % Oxidation Data at 5° C. for Long-Term Stability Study of anti-NGF antibody E3 formulation containing trehalose, EDTA, polysorbate 20 in histidine buffer at pH 6.0 at 2.5, 5, 10, 20 and 50 mg/mL
Figure 5:
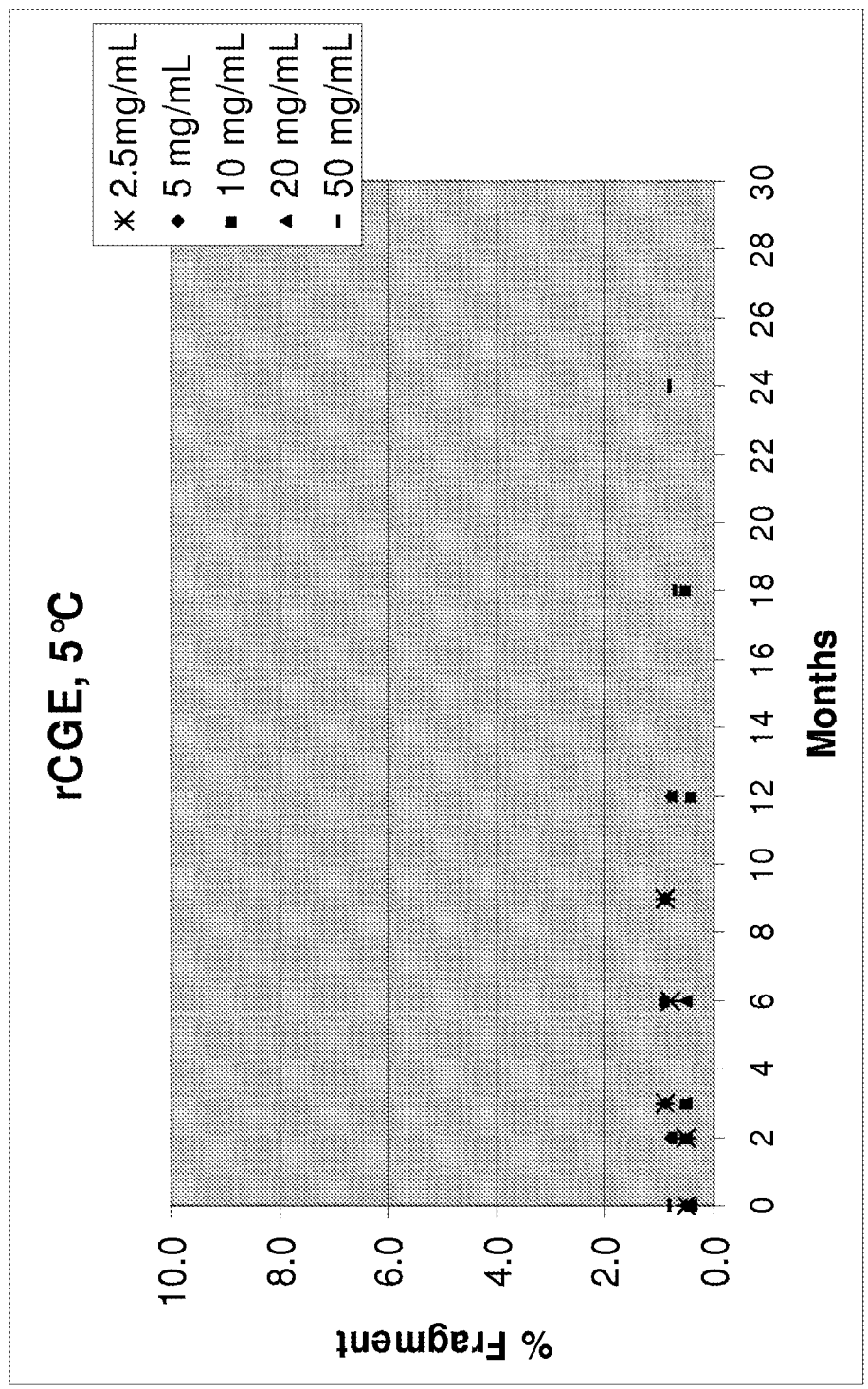
Figure 6:
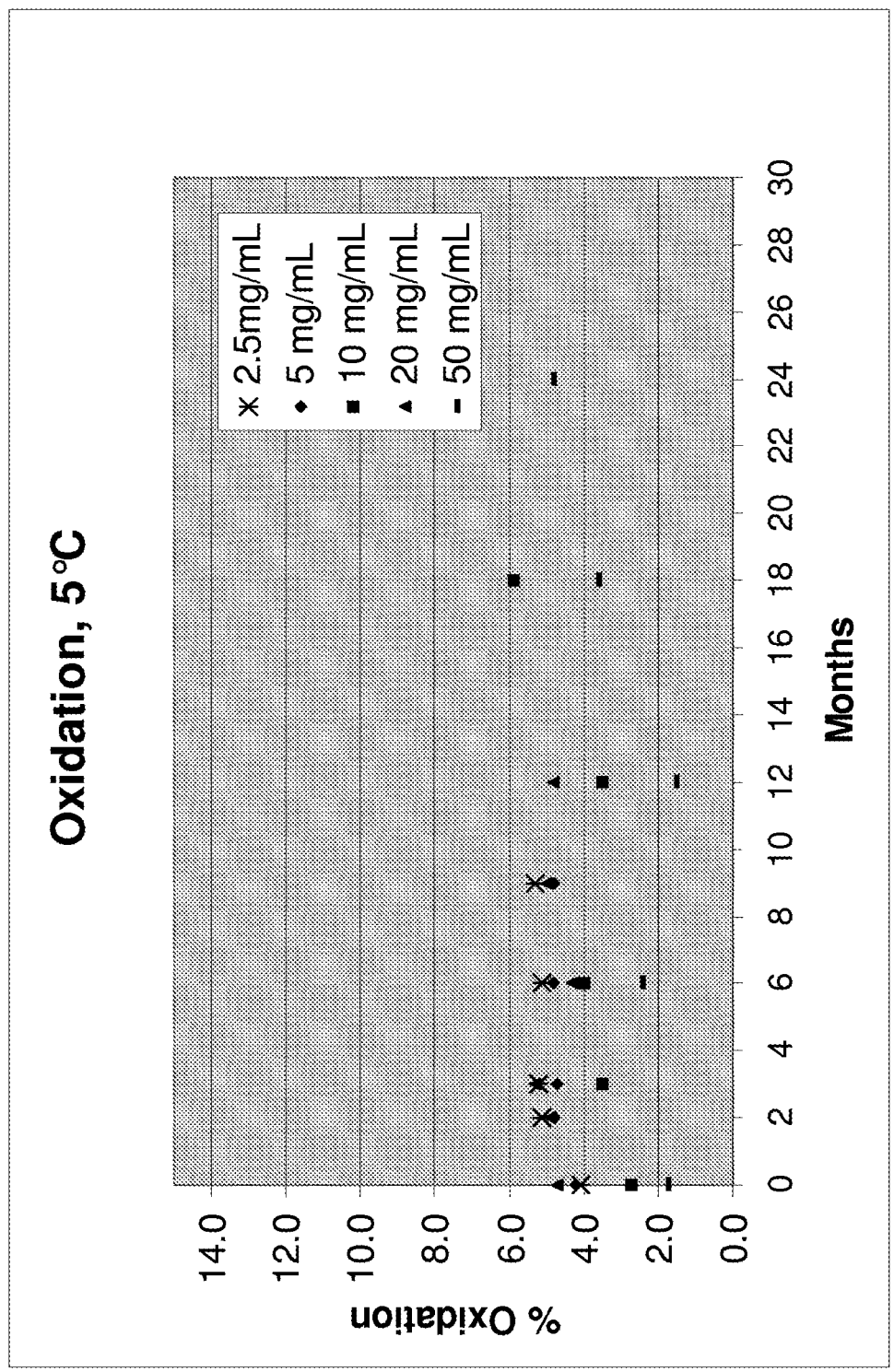

Data collected and presented in FIGS. 4, 5, and 6 indicate that the said formulation of anti-NFG antibody E3 at 2.5, 5, 10, 20 or 50 mg/mL mAb concentration is stable for up to 52 weeks.

An example of a liquid antibody composition according to the present invention is as follows:

any of about 2.5 mg/ml, 5 mg/ml, 10 mg/ml, 20 mg/ml, 22 mg/ml or about 50 mg/ml of an antibody comprising a variable heavy chain sequence of SEQ ID NO. 1 and a variable light chain sequence of SEQ ID NO. 2, about 10 mM histidine buffer, about 84 mg/ml trehalose dihydrate, about 0.01 weight/volume Polysorbate 20, about 0.005% disodium EDTA, wherein said composition is of a pH 6.0+/−0.2. The liquid antibody composition is preferably of a total volume of around 1 ml.

Antibody Sequences

```
Heavy chain variable region E3 (Kabat CDRs are
underlined; Chothia CDRs are BOLD AND ITALICIZED)
                                       (SEQ ID NO: 1)
QVQLQESGPGLVKPSETLSLTCTVS GFSLIGYDLNWIRQPPGKGLEWIG

IIWGDGTTDYNSAVKSRVTISKDTSKNQFSLKLSSVTAADTAVYYCA

RGGYWYATSYYFDYWGQGTLVTVS

Light chain variable region E3 (Kabat CDRs are
underlined; Chothia CDRs are BOLD AND ITALICIZED)
                                       (SEQ ID NO: 2)
DIQMTQSPSSLSASVGDRVTITC RASQSISNNLNWYQQKPGKAPKLLIY

YTSRFHSGVPSRFSGSGSGTDFTFTISSLQPEDIATYYC QQEHTLPYTF

GQGTKLEIKRT

E3 heavy chain extended CDRs
CDRH1: GFSLIGYDLN               (SEQ ID NO: 3)

CDRH2: IIWGDGTTDYNSAVKS         (SEQ ID NO: 4)

CDRH3: GGYWYATSYYFDY            (SEQ ID NO: 5)
```

```
E3 light chain extended CDRs
CDRL1: RASQSISNNLN                (SEQ ID NO: 6)

CDRL2: YTSRFHS                    (SEQ ID NO: 7)

CDRL3: QQEHTLPYT                  (SEQ ID NO: 8)

Mouse monoclonal antibody 911 extended CDRs
911 heavy chain extended CDRs
CDRH1 : GFSLIGYDIN                (SEQ ID NO: 9)

CDRH2 : MIWGDTTDYNSALKS           (SEQ ID NO: 10)

CDRH3: GGYYYGTSYYFDY              (SEQ ID NO: 11)

911 light chain extended CDRs
CDRL1: RASQDISNHLN                (SEQ ID NO: 12)

CDRL2: YISRFHS                    (SEQ ID NO: 13)

CDRL3: QQSKTLPYT                  (SEQ ID NO: 14)

E3 heavy chain amino acid sequence (full)
                                  (SEQ ID NO: 16)
QVQLQESGPGLVKPSETLSLTCTVSGFSLIGYDLNWIRQPPGKGLEWIG

IIWGDGTTDYNSAVKSRVTISKDTSKNQFSLKLSSVTAADTAVYYCARG

GYWYATSYYFDYWGQGTLVTVSSASTKGPSVFPLAPCSRSTSESTAALG

CLVKDYFPEPVTVSWNSGALTSGVHTFPAVLQSSGLYSLSSVVTVPSSN

FGTQTYTCNVDHKPSNTKVDKTVERKCCVECPPCPAPPVAGPSVFLFPP

KPKDTLMISRTPEVTCVVVDVSHEDPEVQFNWYVDGVEVHNAKTKPREE

QFNSTFRVVSVLTVVHQDWLNGKEYKCKVSNKGLPSSIEKTISKTKGQP

REPQVYTLPPSREEMTKNQVSLTCLVKGFYPSDIAVEWESNGQPENNYK

TTPPMLDSDGSFFLYSKLTVDKSRWQQGNVFSCSVMHEALHNHYTQKSL

SLSPGK 3E light chain amino acid sequence (full antibody)
                                  (SEQ ID NO: 17)
DIQMTQSPSSLSASVGDRVTITCRASQSISNNLNWYQQKPGKAPKLLIY

YTSRFHSGVPSRFSGSGSGTDFTFTISSLQPEDIATYYCQQEHTLPYTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Other additional CDR sequences referred to
RASQSISNNLN                       (SEQ ID NO: 18)

YTSRFHS                           (SEQ ID NO: 19)

GFSLIGYDLN                        (SEQ ID NO: 30)

IIWGDGTTDYNSAV                    (SEQ ID NO: 31)

QQEHTLPYT                         (SEQ ID NO: 55)

GGYWYATSYYFDY                     (SEQ ID NO: 56)

QQESTLPYT                         (SEQ ID NO: 57)

GGYWYSTSYYFDY                     (SEQ ID NO: 58)

QQEKTLPYT                         (SEQ ID NO: 59)

GGYYYATSYYFDY                     (SEQ ID NO: 60)

QQERTLPYT                         (SEQ ID NO: 61)

GGYWYATSYYFDY                     (SEQ ID NO: 62)

QQERTLPYT                         (SEQ ID NO: 63)

GGYYYATSYYFDY                     (SEQ ID NO: 64)

3E heavy chain nucleotide sequence (full antibody)
                                  (SEQ ID NO: 65)
CAGGTGCAGCTGCAGGAGTCTGGCCCAGGACTGGTGAAGCCTTCCGAGA

CCCTGTCCCTCACCTGCACTGTCTCTGGGTTCTCACTTATCGGCTATGA

TCTTAACTGGATCCGACAGCCTCCAGGGAAGGGACTGGAGTGGATTGGG

ATTATCTGGGGTGATGGAACCACAGACTATAATTCAGCTGTCAAATCCC

GCGTCACCATCTCAAAAGACACCTCCAAGAACCAGTTCTCCCTGAAGCT

GAGCTCTGTGACCGCCGCGGACACGGCCGTGTATTACTGTGCGAGAGGA

GGTTATTGGTACGCCACTAGCTACTACTTTGACTACTGGGGCCAGGGCA

CCCTGGTCACCGTCTCCTCAGCCTCCACCAAGGGCCCATCTGTCTTCCC

ACTGGCCCCATGCTCCCGCAGCACCTCCGAGAGCACAGCCGCCCTGGGC

TGCCTGGTCAAGGACTACTTCCCAGAACCTGTGACCGTGTCCTGGAACT

CTGGCGCTCTGACCAGCGGCGTGCACACCTTCCCAGCTGTCCTGCAGTC

CTCAGGTCTCTACTCCCTCAGCAGCGTGGTGACCGTGCCATCCAGCAAC

TTCGGCACCCAGACCTACACCTGCAACGTAGATCACAAGCCAAGCAACA

CCAAGGTCGACAAGACCGTGGAGAGAAAGTGTTGTGTGGAGTGTCCACC

TTGTCCAGCCCCTCCAGTGGCCGGACCATCCGTGTTCCTGTTCCCTCCA

AAGCCAAAGGACACCCTGATGATCTCCAGAACCCCAGAGGTGACCTGTG

TGGTGGTGGACGTGTCCCACGAGGACCCAGAGGTGCAGTTCAACTGGTA

TGTGGACGGAGTGGAGGTGCACAACGCCAAGACCAAGCCAAGAGAGGAG

CAGTTCAACTCCACCTTCAGAGTGGTGAGCGTGCTGACCGTGGTGCACC

AGGACTGGCTGAACGGAAAGGAGTATAAGTGTAAGGTGTCCAACAAGGG

ACTGCCATCCAGCATCGAGAAGACCATCTCCAAGACCAAGGGACAGCCA

AGAGAGCCACAGGTGTATACCCTGCCACCATCCAGAGAGGAGATGACCA

AGAACCAGGTGTCCCTGACCTGTCTGGTGAAGGGATTCTATCCATCCGA

CATCGCCGTGGAGTGGGAGTCCAACGGACAGCCAGAGAACAACTATAAG

ACCACCCCTCCAATGCTGGACTCCGACGGATCCTTCTTCCTGTATTCCA

AGCTGACCGTGGACAAGTCCAGATGGCAGCAGGGAAACGTGTTCTCTTG

TTCCGTGATGCACGAGGCCCTGCACAACCACTATACCCAGAAGAGCCTG

TCCCTGTCTCCAGGAAAGTAA 3E heavy chain variable domain nucleotide sequence
                                  (SEQ ID NO: 66)
CAGGTGCAGCTGCAGGAGTCTGGCCCAGGACTGGTGAAGCCTTCCGAGA

CCCTGTCCCTCACCTGCACTGTCTCTGGGTTCTCACTTATCGGCTATGA

TCTTAACTGGATCCGACAGCCTCCAGGGAAGGGACTGGAGTGGATTGGG

ATTATCTGGGGTGATGGAACCACAGACTATAATTCAGCTGTCAAATCCC

GCGTCACCATCTCAAAAGACACCTCCAAGAACCAGTTCTCCCTGAAGCT

GAGCTCTGTGACCGCCGCGGACACGGCCGTGTATTACTGTGCGAGAGGA

GGTTATTGGTACGCCACTAGCTACTACTTTGACTACTGGGGCCAGGGCA

CCCTGGTCACCGTCTCCTCA 3E light chain nucleotide sequence (full antibody)
```

-continued
(SEQ ID NO: 67)
GATATCCAGATGACACAGTCCCCATCCTCCCTGTCTGCCTCTGTGGGTG

ACCGCGTCACCATCACCTGCCGCGCATCTCAGTCCATTAGCAATAATCT

GAACTGGTATCAGCAGAAGCCAGGCAAAGCCCCAAAACTCCTGATCTAC

TACACCTCACGCTTCCACTCAGGTGTCCCATCACGCTTCAGTGGCAGTG

GCTCTGGTACAGATTTCACCTTCACCATTAGCAGCCTGCAACCAGAAGA

TATTGCCACTTATTACTGCCAACAGGAGCATACCCTTCCATATACCTTC

GGTCAAGGCACCAAGCTGGAGATCAAACGCACTGTGGCTGCACCATCTG

TCTTCATCTTTCCTCCATCTGATGAGCAGTTGAAATCCGGAACTGCCTC

TGTTGTGTGCCTGCTGAATAACTTCTATCCACGCGAGGCCAAAGTACAG

TGGAAGGTGGATAACGCCCTCCAATCCGGTAACTCCCAGGAGAGTGTCA

CAGAGCAGGACAGCAAGGACAGCACCTACAGCCTCAGCAGCACCCTGAC

CCTGAGCAAAGCAGACTACGAGAAACACMAAGTCTACGCCTGCGAAGTC

ACCCATCAGGGCCTGAGTTCTCCAGTCACAAAGAGCTTCAACCGCGGTG

AGTGCTAA 3E light chain variable domain nucleotide sequence
(SEQ ID NO: 68)
GATATCCAGATGACACAGTCCCCATCCTCCCTGTCTGCCTCTGTGGGTG

ACCGCGTCACCATCACCTGCCGCGCATCTCAGTCCATTAGCAATAATCT

GAACTGGTATCAGCAGAAGCCAGGCAAAGCCCCAAAACTCCTGATCTAC

TACACCTCACGCTTCCACTCAGGTGTCCCATCACGCTTCAGTGGCAGTG

GCTCTGGTACAGATTTCACCTTCACCATTAGCAGCCTGCAACCAGAAGA

TATTGCCACTTATTACTGCCAACAGGAGCATACCCTTCCATATACCTTC

GGTCAAGGCACCAAGCTGGAGATCAAACGC

The above sequences and other sequences described herein are provided in the attached sequence listing.

It is understood that the examples and embodiments described herein are for illustrative purposes only and that various modifications or changes in light thereof will be suggested to persons skilled in the art and are to be included within the spirit and purview of this application.

The invention claimed is:

1. A liquid composition comprising;
about 2.5 mg/ml to about 20 mg/ml of an anti-NGF antibody,
about 80 mg/ml to 85 mg/ml trehalose dihydrate,
about 9.0 mM to 10.0 mM histidine buffer,
about 0.05 mg/ml to 0.1 mg/ml disodium EDTA, and
about 0.01 mg/ml to 0.15 mg/ml polysorbate 20 (PS20),
wherein the pH of said composition is from 5.8 to 6.8,
wherein the antibody comprises a heavy chain variable region amino acid sequence shown in SEQ ID NO: 1, and a light chain variable region amino acid sequence shown in SEQ ID NO: 2.

2. The liquid composition according to claim 1 which further comprises an antioxidant agent and/or a preservative agent.

3. The liquid composition according to claim 1 which does not comprise an antioxidant agent, a preservative agent or both.

4. The liquid composition according to claim 1 comprising;
2.5 mg/ml to about 20 mg/ml of said anti-NGF antibody,
9.0 mM to 10.0 mM histidine buffer,
80 mg/ml to 85 mg/ml trehalose dihydrate,
0.01 mg/ml to 0.15 mg/ml PS20, and
0.05 mg/ml to 0.1 mg/ml disodium EDTA,
wherein said composition is of a pH from 5.8 to 6.8,
wherein the antibody comprises a heavy chain variable region amino acid sequence shown in SEQ ID NO: 1, and a light chain variable region amino acid sequence shown in SEQ ID NO: 2.

5. The liquid composition according to claim 3 consisting of;
about 2.5 mg/ml to about 20 mg/ml of said anti-NGF antibody,
about 9.0 mM to 10.0 mM histidine buffer,
about 80 mg/ml to 85 mg/ml trehalose dihydrate,
about 0.01 mg/ml to 0.15 mg/ml PS20, and
about 0.05 mg/ml to 0.1 mg/ml disodium EDTA,
wherein said composition is of a pH from 5.8 to 6.8.

6. The liquid composition according to claim 1 comprising;
about 2.5 mg/ml, 5 mg/ml, 10 mg/ml, or 20 mg/ml, of said anti-NGF antibody,
about 10 mM histidine buffer,
about 84 mg/ml trehalose dihydrate,
about 0.1 mg/ml PS20, and
about 0.05 mg/ml disodium EDTA,
wherein said composition is of a pH 6.0+/−0.2.

7. The liquid composition according to claim 1 comprising;
about 2.5 mg/ml, 5 mg/ml, 10 mg/ml, or 20 mg/ml of said anti-NGF antibody,
about 10 mM histidine buffer,
about 84 mg/ml trehalose dihydrate,
about 0.1 mg/ml PS20, and
about 0.05 mg/ml disodium EDTA,
wherein said composition is of a pH from 5.8 to 6.5.

8. The liquid composition according to claim 1 wherein the composition is not lyophilized.

9. The liquid composition according to claim 1 wherein the composition can be stored for a period of at least about 26 weeks at a temperature of about 40° C. and wherein there is less than about 10% increase in aggregation of the antibody of the composition.

10. The liquid composition according to claim 1 wherein the composition can be stored for a period of at least about 26 weeks at a temperature of about 40° C. and wherein there is less than about 10% increase in oxidation of the antibody of the composition.

11. The liquid composition according to claim 1 wherein the composition can be stored for a period of at least about 26 weeks at a temperature of about 40° C. and wherein there is less than about 10% decrease in activity of the antibody of the composition.

12. The liquid composition according to claim 1 wherein the composition can stored for a period of at least about 26 weeks at a temperature of between 2 to 8° C. and wherein there is less than about 10% increase in aggregation of the antibody of the composition.

13. A pharmaceutical composition for treating pain in a mammal comprising an effective amount of the liquid composition of claim 1.

* * * * *

SEQUENCE LISTING

<160> NUMBER OF SEQ ID NOS: 77

<210> SEQ ID NO 1
<211> LENGTH: 120
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
                20                  25                  30

Asp Leu Asn Trp Ile Arg Gln Pro Pro Gly Lys Gly Leu Glu Trp Ile
            35                  40                  45

Gly Ile Ile Trp Gly Asp Gly Thr Thr Asp Tyr Asn Ser Ala Val Lys
        50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
                100                 105                 110

Gln Gly Thr Leu Val Thr Val Ser
            115                 120

<210> SEQ ID NO 2
<211> LENGTH: 109
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Asn Asn
             20                  25                  30

Leu Asn Trp Tyr Gln Gln Lys Pro Gly Lys Ala Pro Lys Leu Leu Ile
         35                  40                  45

Tyr Tyr Thr Ser Arg Phe His Ser Gly Val Pro Ser Arg Phe Ser Gly
     50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                 85                  90                  95

Thr Phe Gly Gln Gly Thr Lys Leu Glu Ile Lys Arg Thr
            100                 105
```

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

```
Gly Phe Ser Leu Ile Gly Tyr Asp Leu Asn
1               5                   10
```

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

```
Ile Ile Trp Gly Asp Gly Thr Thr Asp Tyr Asn Ser Ala Val Lys Ser
1               5                   10                  15
```

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

```
Gly Gly Tyr Trp Tyr Ala Thr Ser Tyr Tyr Phe Asp Tyr
1               5                   10
```

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

```
Arg Ala Ser Gln Ser Ile Ser Asn Asn Leu Asn
1               5                   10
```

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Tyr Thr Ser Arg Phe His Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Gln Gln Glu His Thr Leu Pro Tyr Thr
1               5

<210> SEQ ID NO 9
<211> LENGTH: 10
<212> TYPE: PRT
<213> ORGANISM: Mus musculus

<400> SEQUENCE: 9

Gly Phe Ser Leu Ile Gly Tyr Asp Ile Asn
1               5                   10

<210> SEQ ID NO 10
<211> LENGTH: 16
<212> TYPE: PRT
<213> ORGANISM: Mus musculus

<400> SEQUENCE: 10

Met Ile Trp Gly Asp Gly Thr Thr Asp Tyr Asn Ser Ala Leu Lys Ser
1               5                   10                  15

<210> SEQ ID NO 11
<211> LENGTH: 13
<212> TYPE: PRT
<213> ORGANISM: Mus musculus

<400> SEQUENCE: 11

Gly Gly Tyr Tyr Tyr Gly Thr Ser Tyr Tyr Phe Asp Tyr
1               5                   10

<210> SEQ ID NO 12
<211> LENGTH: 11
<212> TYPE: PRT
<213> ORGANISM: Mus musculus

<400> SEQUENCE: 12

Arg Ala Ser Gln Asp Ile Ser Asn His Leu Asn
1               5                   10

<210> SEQ ID NO 13
<211> LENGTH: 7
<212> TYPE: PRT
<213> ORGANISM: Mus musculus

<400> SEQUENCE: 13

Tyr Ile Ser Arg Phe His Ser
1               5

<210> SEQ ID NO 14
<211> LENGTH: 9
<212> TYPE: PRT
<213> ORGANISM: Mus musculus

<400> SEQUENCE: 14

Gln Gln Ser Lys Thr Leu Pro Tyr Thr
1               5

<210> SEQ ID NO 15
<211> LENGTH: 15
<212> TYPE: PRT
<213> ORGANISM: Artificial Sequence
<220> FEATURE:
<223> OTHER INFORMATION: Synthetic Construct

<400> SEQUENCE: 15

Gly Gly Gly Gly Ser Gly Gly Gly Ser Gly Gly Gly Ser
1               5                   10                  15

<210> SEQ ID NO 16
<211> LENGTH: 447
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
                20                  25                  30

Asp Leu Asn Trp Ile Arg Gln Pro Pro Gly Lys Gly Leu Glu Trp Ile
            35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys

```
            275                 280                 285
Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 17
<211> LENGTH: 214
<212> TYPE: PRT
<213> ORGANISM: Artificial Sequence
<220> FEATURE:
<223> OTHER INFORMATION: Synthetic Construct

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

Phe Asn Arg Gly Glu Cys
    210

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Arg Ala Ser Gln Ser Ile Ser Asn Asn Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Tyr Thr Ser Arg Phe His Ser
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Arg Ala Ser Gln Tyr Ile Ser Asn His Leu Asn
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Tyr Thr Ser Arg Phe His Ser
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Arg Ala Ser Gln Ser Ile Ser Asn Gln Leu Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Tyr Val Ser Arg Phe His Ser
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Arg Ala Phe Gln Ala Ile Ser Asn Gln Leu Asn
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Tyr Ile Ser Arg Phe His Thr
1               5

<210> SEQ ID NO 26
<211> LENGTH: 11
<212> TYPE: PRT
<213> ORGANISM: Artificial Sequence
<220> FEATURE:
<223> OTHER INFORMATION: Synthetic Construct

<400> SEQUENCE: 26

Arg Ala Phe Gln Ser Ile Ser Asn Gln Leu Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Tyr Ala Ser Arg Phe His Ser
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Gly Phe Ser Leu Ile Gly Tyr Asp Ser Asn
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic Construct

<400> SEQUENCE: 29

Ile Ile Trp Gly Asp Gly Thr Thr Asp Tyr Asn Ser Ala Leu
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Gly Phe Ser Leu Ile Gly Tyr Asp Leu Asn
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

Ile Ile Trp Gly Asp Gly Thr Thr Asp Tyr Asn Ser Ala Val
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Gly Phe Ser Leu Ile Gly Tyr Asp Val Thr
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Gly Ile Trp Gly Asp Gly Thr Thr Asp Tyr Asn Ser Ala Val
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Gly Phe Ser Leu Ile Gly Tyr Asp Val Thr
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic Construct

<400> SEQUENCE: 35

Gly Ile Trp Gly Asp Gly Thr Thr Asp Tyr Asn Ser Ser Val

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Gly Phe Ser Leu Ile Gly Tyr Asp Ala Thr
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic Construct

<400> SEQUENCE: 37

Gly Ile Trp Gly Asp Gly Thr Thr Asp Tyr Asn Ser Ala Val
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Gly Phe Ser Leu Ile Gly Tyr Asp Val Ser
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic Construct

<400> SEQUENCE: 39

Ile Ile Trp Gly Asp Gly Thr Thr Asp Tyr Asn Ser Ser Val
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic Construct

<400> SEQUENCE: 40

Gly Phe Ser Leu Ile Gly Tyr Asp Ile Ser
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic Construct

<400> SEQUENCE: 41

Gln Ile Trp Gly Asp Gly Thr Thr Asp Tyr Asn Ser Ser Val
1               5                   10

```
<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Phe Ser Leu Ile Gly Tyr Asp Ala Ser
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthetic Construct

<400> SEQUENCE: 43

Gly Ile Trp Gly Asp Gly Thr Thr Asp Tyr Asn Ser Ser Val
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Gly Phe Ser Leu Ile Gly Tyr Asp Ser Thr
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Synthetic Construct

<400> SEQUENCE: 45

Ser Ile Trp Gly Asp Gly Thr Thr Asp Tyr Asn Ser Ala Leu
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic Construct

<400> SEQUENCE: 46

Gly Gly Tyr Trp Tyr Gly Thr Ser Tyr Tyr Phe Asp Tyr
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic Construct

<400> SEQUENCE: 47

Gly Gly Tyr Tyr Tyr Gly Thr Ala Tyr Tyr Phe Asp Tyr
1               5                   10
```

<210> SEQ ID NO 48
<211> LENGTH: 13
<212> TYPE: PRT
<213> ORGANISM: Artificial Sequence
<220> FEATURE:
<223> OTHER INFORMATION: Synthetic Construct

<400> SEQUENCE: 48

Gly Gly Tyr Tyr Tyr Gly Thr Thr Tyr Tyr Phe Asp Tyr
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic Construct

<400> SEQUENCE: 49

Gly Gly Tyr Tyr Tyr Ala Thr Ser Tyr Tyr Phe Asp Tyr
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct

<400> SEQUENCE: 50

Gln Gln Glu Lys Thr Leu Pro Tyr Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Construct

<400> SEQUENCE: 51

Gln Gln Glu Ala Thr Leu Pro Tyr Thr
1               5

<210> SEQ ID NO 52
<211> LENGTH: 13
<212> TYPE: PRT
<213> ORGANISM: Artificial Sequence
<220> FEATURE:
<223> OTHER INFORMATION: Synthetic Construct

<400> SEQUENCE: 52

Gly Gly Tyr Trp Tyr Ala Thr Ser Tyr Tyr Phe Asp Tyr
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Synthetic Construct

<400> SEQUENCE: 53

Gln Gln Glu Arg Thr Leu Pro Tyr Thr
1               5

```
<210> SEQ ID NO 54
<211> LENGTH: 13
<212> TYPE: PRT
<213> ORGANISM: Artificial Sequence
<220> FEATURE:
<223> OTHER INFORMATION: Synthetic Construct

<400> SEQUENCE: 54

Gly Gly Tyr Trp Tyr Ala Thr Ser Tyr Tyr Phe Asp Tyr
 1               5                  10

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Gln Gln Glu His Thr Leu Pro Tyr Thr
 1               5

<210> SEQ ID NO 56
<211> LENGTH: 13
<212> TYPE: PRT
<213> ORGANISM: Artificial Sequence
<220> FEATURE:
<223> OTHER INFORMATION: Synthetic Construct

<400> SEQUENCE: 56

Gly Gly Tyr Trp Tyr Ala Thr Ser Tyr Tyr Phe Asp Tyr
 1               5                  10

<210> SEQ ID NO 57
<211> LENGTH: 9
<212> TYPE: PRT
<213> ORGANISM: Artificial Sequence
<220> FEATURE:
<223> OTHER INFORMATION: Synthetic Construct

<400> SEQUENCE: 57

Gln Gln Glu Ser Thr Leu Pro Tyr Thr
 1               5

<210> SEQ ID NO 58
<211> LENGTH: 13
<212> TYPE: PRT
<213> ORGANISM: Artificial Sequence
<220> FEATURE:
<223> OTHER INFORMATION: Synthetic Construct

<400> SEQUENCE: 58

Gly Gly Tyr Trp Tyr Ser Thr Ser Tyr Tyr Phe Asp Tyr
 1               5                  10

<210> SEQ ID NO 59
<211> LENGTH: 9
<212> TYPE: PRT
<213> ORGANISM: Artificial Sequence
<220> FEATURE:
<223> OTHER INFORMATION: Synthetic Construct

<400> SEQUENCE: 59

Gln Gln Glu Lys Thr Leu Pro Tyr Thr
 1               5

<210> SEQ ID NO 60
```

<211> LENGTH: 13
<212> TYPE: PRT
<213> ORGANISM: Artificial Sequence
<220> FEATURE:
<223> OTHER INFORMATION: Synthetic Construct

<400> SEQUENCE: 60

Gly Gly Tyr Tyr Tyr Ala Thr Ser Tyr Tyr Phe Asp Tyr
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Gln Gln Glu Arg Thr Leu Pro Tyr Thr
1               5

<210> SEQ ID NO 62
<211> LENGTH: 13
<212> TYPE: PRT
<213> ORGANISM: Artificial Sequence
<220> FEATURE:
<223> OTHER INFORMATION: Synthetic Construct

<400> SEQUENCE: 62

Gly Gly Tyr Trp Tyr Ala Thr Ser Tyr Tyr Phe Asp Tyr
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Gln Gln Glu Arg Thr Leu Pro Tyr Thr
1               5

<210> SEQ ID NO 64
<211> LENGTH: 13
<212> TYPE: PRT
<213> ORGANISM: Artificial Sequence
<220> FEATURE:
<223> OTHER INFORMATION: Synthetic Construct

<400> SEQUENCE: 64

Gly Gly Tyr Tyr Tyr Ala Thr Ser Tyr Tyr Phe Asp Tyr
1               5                   10

<210> SEQ ID NO 65
<211> LENGTH: 1344
<212> TYPE: DNA
<213> ORGANISM: Artificial Sequence
<220> FEATURE:
<223> OTHER INFORMATION: Synthetic Construct

<400> SEQUENCE: 65
caggtgcagc tgcaggagtc tggcccagga ctggtgaagc cttccgagac cctgtccctc        60
acctgcactg tctctgggtt ctcacttatc ggctatgatc ttaactggat ccgacagcct       120
ccagggaagg gactggagtg gattgggatt atctggggtg atggaaccac agactataat       180

```
tcagctgtca aatcccgcgt caccatctca aaagacacct ccaagaacca gttctccctg    240
aagctgagct ctgtgaccgc cgcggacacg gccgtgtatt actgtgcgag aggaggttat    300
tggtacgcca ctagctacta ctttgactac tggggccagg gcaccctggt caccgtctcc    360
tcagcctcca ccaagggccc atctgtcttc ccactggccc catgctcccg cagcacctcc    420
gagagcacag ccgccctggg ctgcctggtc aaggactact cccagaaccc tgtgaccgtg    480
tcctggaact ctggcgctct gaccagcggc gtgcacacct cccagctgt cctgcagtcc    540 tcaggtctct actccctcag cagcgtggtg accgtgccat ccagcaactt cggcacccag    600
acctacacct gcaacgtaga tcacaagcca agcaacacca aggtcgacaa gaccgtggag    660
agaaagtgtt gtgtggagtg tccaccttgt ccagcccctc cagtggccgg accatccgtg    720
ttcctgttcc ctccaaagcc aaaggacacc ctgatgatct ccagaacccc agaggtgacc    780
tgtgtggtgg tggacgtgtc ccacgaggac ccagaggtgc agttcaactg gtatgtggac    840
ggagtggagg tgcacaacgc caagaccaag ccaagagagg agcagttcaa ctccaccttc    900
agagtggtga gcgtgctgac cgtggtgcac caggactggc tgaacggaaa ggagtataag    960
tgtaaggtgt ccaacaaggg actgccatcc agcatcgaga agaccatctc caagaccaag   1020
ggacagccaa gagagccaca ggtgtatacc ctgccaccat ccagagagga gatgaccaag   1080
aaccaggtgt ccctgacctg tctggtgaag ggattctatc catccgacat cgccgtggag   1140
tgggagtcca acggacagcc agagaacaac tataagacca cccctccaat gctggactcc   1200
gacggatcct tcttcctgta ttccaagctg accgtggaca gtccagatg cagcaggga    1260 aacgtgttct cttgttccgt gatgcacgag gccctgcaca accactatac ccagaagagc   1320
ctgtccctgt ctccaggaaa gtaa                                          1344
```

<210> SEQ ID NO 66
<211> LENGTH: 363
<212> TYPE: DNA
<213> ORGANISM: Artificial Sequence
<220> FEATURE:
<223> OTHER INFORMATION: Synthetic Construct

<400> SEQUENCE: 66

```
caggtgcagc tgcaggagtc tgcccagga ctggtgaagc cttccgagac cctgtccctc      60
acctgcactg tctctgggtt ctcacttatc ggctatgatc ttaactggat ccgacagcct    120
ccagggaagg gactggagtg gattgggatt atctggggtg atggaaccac agactataat    180
tcagctgtca aatcccgcgt caccatctca aaagacacct ccaagaacca gttctccctg    240
aagctgagct ctgtgaccgc cgcggacacg gccgtgtatt actgtgcgag aggaggttat    300
tggtacgcca ctagctacta ctttgactac tggggccagg gcaccctggt caccgtctcc    360
tca                                                                  363
```

<210> SEQ ID NO 67
<211> LENGTH: 645
<212> TYPE: DNA
<213> ORGANISM: Artificial Sequence
<220> FEATURE:
<223> OTHER INFORMATION: Synthetic Construct

<400> SEQUENCE: 67

```
gatatccaga tgacacagtc cccatcctcc ctgtctgcct ctgtgggtga ccgcgtcacc     60
atcacctgcc gcgcatctca gtccattagc aataatctga ctggtatca gcagaagcca    120 ggcaaagccc caaaactcct gatctactac acctcacgct tccactcagg tgtcccatca    180
```

```
cgcttcagtg gcagtggctc tggtacagat ttcaccttca ccattagcag cctgcaacca    240
gaagatattg ccacttatta ctgccaacag gagcataccc ttccatatac cttcggtcaa    300
ggcaccaagc tggagatcaa acgcactgtg gctgcaccat ctgtcttcat ctttcctcca    360
tctgatgagc agttgaaatc cggaactgcc tctgttgtgt gcctgctgaa taacttctat    420
ccacgcgagg ccaaagtaca gtggaaggtg gataacgccc tccaatccgg taactcccag    480
gagagtgtca cagagcagga cagcaaggac agcacctaca gcctcagcag caccctgacc    540
ctgagcaaag cagactacga gaaacacmaa gtctacgcct gcgaagtcac ccatcagggc    600
ctgagttctc cagtcacaaa gagcttcaac cgcggtgagt gctaa    645
```

<210> SEQ ID NO 68
<211> LENGTH: 324
<212> TYPE: DNA
<213> ORGANISM: Artificial Sequence
<220> FEATURE:
<223> OTHER INFORMATION: Synthetic Construct

<400> SEQUENCE: 68

```
gatatccaga tgacacagtc cccatcctcc ctgtctgcct ctgtgggtga ccgcgtcacc     60
atcacctgcc gcgcatctca gtccattagc aataatctga actggtatca gcagaagcca    120
ggcaaagccc caaaactcct gatctactac acctcacgct ccactcaggt gtcccatca    180 cgcttcagtg gcagtggctc tggtacagat ttcaccttca ccattagcag cctgcaacca    240
gaagatattg ccacttatta ctgccaacag gagcataccc ttccatatac cttcggtcaa    300
ggcaccaagc tggagatcaa acgc    324
```

<210> SEQ ID NO 69
<211> LENGTH: 98
<212> TYPE: PRT
<213> ORGANISM: Homo sapiens

<400> SEQUENCE: 69

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly
```

<210> SEQ ID NO 70
<211> LENGTH: 120
<212> TYPE: PRT
<213> ORGANISM: Artificial Sequence
<220> FEATURE:
<223> OTHER INFORMATION: Synthetic Construct

<400> SEQUENCE: 70

```
Gln Val Gln Leu Gln Glu Ser Gly Pro Gly Leu Val Lys Pro Ser Glu
 1               5                  10                  15
```

```
Thr Leu Ser Leu Thr Cys Thr Val Ser Gly Phe Ser Leu Ile Gly Tyr
            20                  25                  30

Asp Ile Asn Trp Ile Arg Gln Pro Gly Lys Gly Leu Glu Trp Ile
        35                  40                  45

Gly Met Ile Trp Gly Asp Gly Thr Thr Asp Tyr Asn Ser Ala Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Gly Gly Tyr Tyr Tyr Gly Thr Ser Tyr Tyr Phe Asp Tyr Trp Gly
                100                 105                 110

Gln Gly Thr Leu Val Thr Val Ser
            115                 120

<210> SEQ ID NO 71
<211> LENGTH: 120
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Gln Glu Ser Gly Pro Gly Leu Val Lys Pro Ser Glu
 1               5                   10                  15

Thr Leu Ser Leu Thr Cys Thr Val Ser Gly Phe Ser Leu Ile Gly Tyr
            20                  25                  30

Asp Ile Asn Trp Ile Arg Gln Pro Gly Lys Gly Leu Glu Trp Ile
        35                  40                  45

Gly Met Ile Trp Gly Asp Gly Thr Thr Asp Tyr Asn Ser Ala Leu Lys
 50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Gly Gly Tyr Tyr Tyr Gly Thr Ser Tyr Tyr Phe Asp Tyr Trp Gly
                100                 105                 110

Gln Gly Thr Leu Val Thr Val Ser
            115                 120

<210> SEQ ID NO 72
<211> LENGTH: 120
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu Gln Glu Ser Gly Pro Gly Leu Val Lys Pro Ser Glu
 1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Gly Lys Gly Leu Glu Trp Ile
        35                  40                  45

Gly Ile Ile Trp Gly Asp Gly Thr Thr Asp Tyr Asn Ser Ala Val Lys
 50                  55                  60

Ser Arg Val Thr Ile Ser Lys Asp Thr Ser Lys Asn Gln Phe Ser Leu
```

```
                65                  70                  75                  80
Lys Leu Ser Ser Val Thr Ala Ala Asp Thr Ala Val Tyr Tyr Cys Ala
                    85                  90                  95

Arg Gly Gly Tyr Tyr Tyr Gly Thr Ser Tyr Tyr Phe Asp Tyr Trp Gly
                100                 105                 110

Gln Gly Thr Leu Val Thr Val Ser
        115                 120

<210> SEQ ID NO 73
<211> LENGTH: 95
<212> TYPE: PRT
<213> ORGANISM: Homo sapiens

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 74
<211> LENGTH: 109
<212> TYPE: PRT
<213> ORGANISM: Artificial Sequence
<220> FEATURE:
<223> OTHER INFORMATION: Synthetic Construct

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn His
                20                  25                  30

Leu Asn Trp Tyr Gln Gln Lys Pro Gly Lys Ala Pro Lys Leu Leu Ile
            35                  40                  45

Tyr Tyr Ile Ser Arg Phe His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Lys Thr Leu Pro Tyr
                85                  90                  95

Thr Phe Gly Gln Gly Thr Lys Leu Glu Ile Lys Arg Thr
            100                 105

<210> SEQ ID NO 75
<211> LENGTH: 109
<212> TYPE: PRT
<213> ORGANISM: Artificial Sequence
<220> FEATURE:
<223> OTHER INFORMATION: Synthetic Construct

<400> SEQUENCE: 75

Asp Ile Gln Met Thr Gln Ser Pro Ser Ser Leu Ser Ala Ser Val Gly
```

```
              1               5              10              15
          Asp Arg Val Thr Ile Thr Cys Arg Ala Ser Gln Ser Ile Ser Asn Asn
                           20                  25                  30

Leu Asn Trp Tyr Gln Gln Lys Pro Gly Lys Ala Pro Lys Leu Leu Ile
                           35                  40                  45

Tyr Tyr Thr Ser Arg Phe His Ser Gly Val Pro Ser Arg Phe Ser Gly
                           50                  55                  60

Ser Gly Ser Gly Thr Asp Phe Thr Phe Thr Ile Ser Ser Leu Gln Pro
           65                  70                  75                  80

Glu Asp Ile Ala Thr Tyr Tyr Cys Gln Gln Ser Lys Thr Leu Pro Tyr
                           85                  90                  95

Thr Phe Gly Gln Gly Thr Lys Leu Glu Ile Lys Arg Thr
                          100                 105
```

<210> SEQ ID NO 76
<211> LENGTH: 1429
<212> TYPE: DNA
<213> ORGANISM: Artificial Sequence
<220> FEATURE:
<223> OTHER INFORMATION: Synthetic construct

<400> SEQUENCE: 76

```
atggccaccg actccagaac ctcctggctg ctgacagtgt ccctgctgtg tctgctgtgg      60
ccacaggagg ccagcgctca ggtgcagctg caggagtctg gcccaggact ggtgaagcct     120
tccgagaccc tgtccctcac ctgcactgtc tctgggttct cacttatcgg ctatgatctt     180
aactggatcc gacagcctcc agggaaggga ctggagtgga ttgggattat ctggggtgat     240
ggaaccacag actataattc agctgtcaaa tcccgcgtca ccatctcaaa agacacctcc     300
aagaaccagt tctccctgaa gctgagctct gtgaccgccg cggacacggc cgtgtattac     360
tgtgcgagag aggttattg gtacgccact agctactact ttgactactg gggccagggc     420
accctggtca ccgtctcctc agcctccacc aagggcccat ctgtcttccc actggcccca     480
tgctcccgca gcacctccga gagcacagcc gccctgggct gcctggtcaa ggactacttc     540
ccagaacctg tgaccgtgtc ctggaactct ggcgctctga ccagcggcgt gcacaccttc     600
ccagctgtcc tgcagtcctc aggtctctac tccctcagca gcgtggtgac cgtgccatcc     660
agcaacttcg gcacccagac ctacacctgc aacgtagatc acaagccaag caacaccaag     720
gtcgacaaga ccgtggagag aaagtgttgt gtggagtgtc caccttgtcc agcccctcca     780
gtggccggac catccgtgtt cctgttccct ccaaagccaa aggacaccct gatgatctcc     840
agaaccccag aggtgacctg tgtggtggtg gacgtgtccc acgaggaccc agaggtgcag     900
ttcaactggt atgtggacgg agtggaggtg cacaacgcca agaccaagcc aagagaggag     960
cagttcaact ccaccttcag agtggtgagc gtgctgaccg tggtgcacca ggactggctg    1020
aacggaaagg agtataagtg taaggtgtcc aacaagggac tgccatccag catcgagaag    1080
accatctcca gaccaagggg acagccaaga gagccacagg tgtatacccc tgccaccatc    1140
agagaggaga tgaccaagaa ccaggtgtcc ctgacctgtc tggtgaaggg attctatcca    1200
tccgacatcg ccgtggagtg ggagtccaac ggacagccag agaacaacta taagaccacc    1260
cctccaatgc tggactccga cggatccttc ttcctgtatt ccaagctgac cgtggacaag    1320
tccagatggc agcagggaaa cgtgttctct tgttccgtga tgcacgaggc cctgcacaac    1380
cactataccc agaagagcct gtccctgtct ccaggaaagt aattctaga                1429
```

```
<210> SEQ ID NO 77
<211> LENGTH: 729
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 646
<223> OTHER INFORMATION: m = A or C

<400> SEQUENCE: 77
atggccaccg actccagaac ctcctggctg ctgacagtgt ccctgctgtg tctgctgtgg      60
ccacaggagg ccagcgctga tatccagatg acacagtccc catcctccct gtctgcctct     120
gtgggtgacc gcgtcaccat cacctgccgc gcatctcagt ccattagcaa taatctgaac     180
tggtatcagc agaagccagg caaagcccca aaactcctga tctactacac ctcacgcttc     240
cactcaggtg tcccatcacg cttcagtggc agtggctctg gtacagattt caccttcacc     300
attagcagcc tgcaaccaga agatattgcc acttattact gccaacagga gcatacccct     360
ccatatacct tcggtcaagg caccaagctg gagatcaaac gcactgtggc tgcaccatct     420
gtcttcatct tcctccatc tgatgagcag ttgaaatccg gaactgcctc tgttgtgtgc     480
ctgctgaata acttctatcc acgcgaggcc aaagtacagt ggaaggtgga taacgccctc     540
caatccggta actcccagga gagtgtcaca gagcaggaca gcaaggacag cacctacagc     600
ctcagcagca ccctgaccct gagcaaagca gactacgaga aacacmaagt ctacgcctgc     660
gaagtcaccc atcagggcct gagttctcca gtcacaaaga gcttcaaccg cggtgagtgc     720
taattctag                                                             729
```